US012758174B2

(12) United States Patent
Straka et al.

(10) Patent No.: US 12,758,174 B2
(45) Date of Patent: Oct. 13, 2026

(54) ANALYSIS OF INTRACRANIAL BLOOD VESSELS

(71) Applicant: iSchemaView, Inc., Menlo Park, CA (US)

(72) Inventors: Matúš Straka, Winterthur (CH); Shalini Ambika Amukotuwa, Carlton (AU); Roland Bammer, Carlton (AU)

(73) Assignee: iSchemaView, Inc., Menlo Park, CA (US)

( * ) Notice: Subject to any disclaimer, the term of this patent is extended or adjusted under 35 U.S.C. 154(b) by 0 days.

(21) Appl. No.: 18/959,502

(22) Filed: Nov. 25, 2024

(65) Prior Publication Data

US 2025/0160778 A1 May 22, 2025

Related U.S. Application Data

(62) Division of application No. 16/865,253, filed on May 1, 2020, now Pat. No. 12,150,801.

(Continued)

(51) Int. Cl.

*A61B 6/00* (2024.01)
*A61B 5/00* (2006.01)

(Continued)

(52) U.S. Cl.

CPC ............ *A61B 6/504* (2013.01); *A61B 5/7246* (2013.01); *A61B 5/7264* (2013.01);

(Continued)

(58) Field of Classification Search

CPC .................. A61B 6/504; G06T 7/0012; G06T 207/30101

See application file for complete search history.

(56) References Cited

U.S. PATENT DOCUMENTS 10,614,572 B2 4/2020 Mansi et al.
11,191,505 B2 12/2021 Straka et al.

(Continued)

FOREIGN PATENT DOCUMENTS

CN 102781332 A 11/2012
EP 3425589 A1 1/2019

(Continued)

OTHER PUBLICATIONS

"Development of a Quantitative Intracranial Vascular Features Extraction Tool on 3D MRA Using Semiautomated Open-Curve Active Contour Vessel Tracing" by L. Chen et al. Magnetic Resonance in Medicine. 79:3229-3238, 2018 (Year: 2018).*

(Continued)

*Primary Examiner* — Jason M Ip

(74) *Attorney, Agent, or Firm* — Schwegman Lundberg & Woessner, P.A.

(57) ABSTRACT

Abnormalities of blood vessels associated with brains of individuals can be detected by analyzing images that include the brains of the individuals. Blood vessels included in the images can be identified and densities of blood vessels across hemispheres can be determined. Differences between densities of blood vessels in different hemispheres of the brains of the individuals can be used to determine a probability of an abnormality with respect to one or more blood vessels associated with the brains of the individuals. User interfaces can be generated indicating possible abnormalities associated with the brains of the individuals.

20 Claims, 23 Drawing Sheets

Related U.S. Application Data

(60) Provisional application No. 62/843,227, filed on May 3, 2019.

(51) Int. Cl.

| | |
|---|---|
| ***A61B 6/03*** | (2006.01) |
| ***A61B 6/46*** | (2024.01) |
| ***A61B 6/50*** | (2024.01) |
| ***G06T 7/00*** | (2017.01) |
| ***G16H 30/20*** | (2018.01) |
| ***G16H 30/40*** | (2018.01) |
| ***G16H 50/20*** | (2018.01) |
| ***G16H 50/30*** | (2018.01) |
| ***G16H 50/50*** | (2018.01) |
| ***G16H 50/70*** | (2018.01) |

(52) U.S. Cl.

CPC ............ *A61B 5/7275* (2013.01); *A61B 6/032* (2013.01); *A61B 6/463* (2013.01); *A61B 6/501* (2013.01); *A61B 6/5217* (2013.01); *G06T 7/0012* (2013.01); *G16H 30/20* (2018.01); *G16H 30/40* (2018.01); *G16H 50/20* (2018.01); *G16H 50/30* (2018.01); *G16H 50/50* (2018.01); *G16H 50/70* (2018.01); *G06T 2200/24* (2013.01); *G06T 2207/30016* (2013.01); *G06T 2207/30101* (2013.01)

(56) References Cited

U.S. PATENT DOCUMENTS

| | | | |
|---|---|---|---|
| 2005/0283070 A1 | 12/2005 | Imielinska et al. | |
| 2007/0019846 A1 | 1/2007 | Bullitt et al. | |
| 2009/0328239 A1 | 12/2009 | Brauner et al. | |
| 2010/0021035 A1 | 1/2010 | Gupta et al. | |
| 2010/0296709 A1* | 11/2010 | Ostrovsky-Berman ...................... | G06T 7/162 382/128 |
| 2013/0094731 A1 | 4/2013 | Yokota et al. | |
| 2016/0125595 A1 | 5/2016 | Silbert et al. | |
| 2016/0287100 A1 | 10/2016 | Tong et al. | |
| 2018/0025255 A1 | 1/2018 | Poole et al. | |
| 2020/0359981 A1 | 11/2020 | Straka et al. | |
| 2021/0059623 A1 | 3/2021 | Straka et al. | |

FOREIGN PATENT DOCUMENTS

| | | |
|---|---|---|
| JP | 2008073332 A | 4/2008 |
| JP | 2008104886 A | 5/2008 |
| JP | 2009011828 A | 1/2009 |
| JP | 2009050726 A | 3/2009 |
| JP | 4302180 B2 | 5/2009 |
| JP | 2012125407 A | 7/2012 |
| JP | 2013017781 A | 1/2013 |
| JP | 5890055 B1 | 2/2016 |
| JP | 2017018234 A | 1/2017 |
| JP | 2018011958 A | 1/2018 |
| JP | 2022531514 A | 7/2022 |
| WO | WO-2012081492 A1 | 6/2012 |
| WO | WO-2020227176 A1 | 11/2020 |

OTHER PUBLICATIONS

"A Novel Method for Vessel Segmentation and Automatic Diagnosis of Vascular Stenosis" by C. Sui et al. Proc. IEEE Int. Conf. Robot. Biomim. 2019 (Year: 2019).*

"U.S. Appl. No. 16/865,253, Non Final Office Action mailed Jan. 23, 2024", 12 pgs.

"U.S. Appl. No. 16/865,253, Notice of Allowance mailed Jul. 16, 2024", 7 pgs.

"U.S. Appl. No. 16/865,253, Preliminary Amendment Filed Apr. 6, 2021", 14 pgs.

"U.S. Appl. No. 16/865,253, Response filed Jun. 24, 2024 to Non Final Office Action mailed Jan. 23, 2024", 15 pgs.

"U.S. Appl. No. 16/865,253, Response filed Oct. 23, 2023 to Restriction Requirement mailed Aug. 22, 2023", 11 pgs.

"U.S. Appl. No. 16/865,253, Restriction Requirement mailed Aug. 22, 2023", 7 pgs.

"U.S. Appl. No. 17/083,089, 312 Amendment filed Nov. 2, 2021", 12 pgs.

"U.S. Appl. No. 17/083,089, Non Final Office Action mailed May 3, 2021", 10 pgs.

"U.S. Appl. No. 17/083,089, Notice of Allowability mailed Nov. 10, 2021", 4 pgs.

"U.S. Appl. No. 17/083,089, Notice of Allowance mailed Aug. 20, 2021", 7 pgs.

"U.S. Appl. No. 17/083,089, Response filed Apr. 6, 2021 to Restriction Requirement mailed Feb. 8, 2021", 13 pgs.

"U.S. Appl. No. 17/083,089, Response filed Aug. 3, 2021 to Non-Final Office Action mailed May 3, 2021", 16 pgs.

"U.S. Appl. No. 17/083,089, Restriction Requirement mailed Feb. 8, 2021", 5 pgs.

"European Application Serial No. 20802410.9, Extended European Search Report mailed Jun. 7, 2022", 11 pgs.

"European Application Serial No. 20802410.9, Response filed Dec. 19, 2022 to Extended European Search Report mailed Jun. 7, 2022", 17 pgs.

"International Application Serial No. PCT/US2020/031230, International Preliminary Report on Patentability mailed Nov. 18, 2021", 9 pgs.

"International Application Serial No. PCT/US2020/031230, International Search Report mailed Sep. 18, 2020", 4 pgs.

"International Application Serial No. PCT/US2020/031230, Invitation to Pay Additional Fees mailed Jul. 21, 2020", 2 pgs.

"International Application Serial No. PCT/US2020/031230, Written Opinion mailed Sep. 18, 2020", 7 pgs.

"Japanese Application Serial No. 2022-512706, Notification of Reasons for Refusal mailed Feb. 20, 2024", w/ English translation, 13 pgs.

Amukotuwa, Shalini A., et al., "Automated Detection of Intracranial Large Vessel Occlusions on Computed Tomography Angiography—A Single Center Experience", Stroke, 50(10), (Oct. 2019), 2790-2798.

Frangi, Alejandro F., et al., "Multiscale Vessel Enhancement Filtering", Medical Image Computing and Computer-Assisted Intervention—MICCAI '98; Lecture Notes in Computer Science, vol. 1496, (1998), 130-137.

Klein, Stefan, "elastix: A Toolbox for Intensity-Based Medical Image Registration", IEEE Transactions on Medical Imaging, vol. 29, No. 1, (Jan. 2010), 196-205.

Manniesing, R, et al., "Level set based cerebral vasculature segmentation and diameter quantification in CT angiography", Medical Image Analysis. 10, (2006), 200-214.

Meijs, M, et al., "Artery and vein segmentation of the cerebral vasculature in 4D CT using a 3D fully convolutional neural network", SPIE Medical Imaging, (2018).

Mullins, M E, "The Hyperdense Cerebral Artery Sign on Head CT Scan", Seminars in Ultra CT MRI, (2005), 394-403.

"European Application Serial No. 20802410.9 Response filed Feb. 11, 2025 to Communication Pursuant to Article 94 3 EPC malled Oct. 16, 2024", 22 pages.

"European Application Serial No. 20802410.9, Communication Pursuant to Article 94 3 EPC mailed Oct. 16, 2024", 10 pgs.

"Japanese Application Serial No. 2022-512706, Response filed Aug. 19, 2024 to Notification of Reasons for Refusal mailed Feb. 20, 2024", with English claims, 20 pages.

* cited by examiner

ANALYSIS OF INTRACRANIAL BLOOD VESSELS

PRIORITY CLAIM AND INCORPORATION BY REFERENCE

This application is a divisional of U.S. application Ser. No. 16/865,253, filed May 1, 2020, which claims priority to U.S. Provisional Patent Application Ser. No. 62/843,227, filed on May 3, 2019, and entitled "DETECTION OF INTRACRANIAL LARGE VESSEL OCCLUSIONS", which are incorporated by reference herein in their entirety.

BACKGROUND

Intracranial blood vessels supply nutrients and oxygen to the brain comprising the cerebrum, cerebellum and brainstem. Some arteries supply blood to anterior portions of the brain, while other arteries supply blood to posterior portions of the brain. The main blood vessels include the internal carotid arteries (ICA), the basilar artery (BA) and the vertebral arteries (VA) and are dispersed in both hemispheres of the brain. Blood vessels that supply blood to anterior portions of the brain can include ICAs, the anterior cerebral arteries (ACA), and the middle cerebral arteries (MCA). In addition, blood vessels that supply blood to posterior portions of the brain include the BA, posterior cerebral arteries (PCA), posterior inferior cerebellar arteries (PICA), anterior inferior cerebellar arteries (AICA) and superior cerebellar arteries (SCA).

Disruption of the flow of blood to any part of the brain can have serious effects. The flow of blood to the brain can be interrupted by the narrowing and/or blockage of blood vessels supplying blood to the brain. The disruption of the flow of blood to parts of the brain can impair the function of the brain and result in numbness, weakness, or paralysis to parts of the body. Strokes can occur when blood supply to a portion of the brain is interrupted. Early detection and treatment of a stroke can minimize the damage to the portion(s) of the brain where blood supply was disrupted and minimize the aftereffects of the stroke. Treatment can be done medically, for example, via thrombolysis, or mechanically via an intravascular catheter that allows endovascular clot retrieval (ECR). Clinical studies have shown that in patients with clots in the ICA or MCA in whom blood flow could be restored via ECR have significantly better outcomes than patients who were managed only medically.

BRIEF DESCRIPTION OF DRAWINGS

The present disclosure is illustrated by way of example and not limitation in the figures of the accompanying drawings, in which like references indicate similar elements.

DETAILED DESCRIPTION

Figure 1:
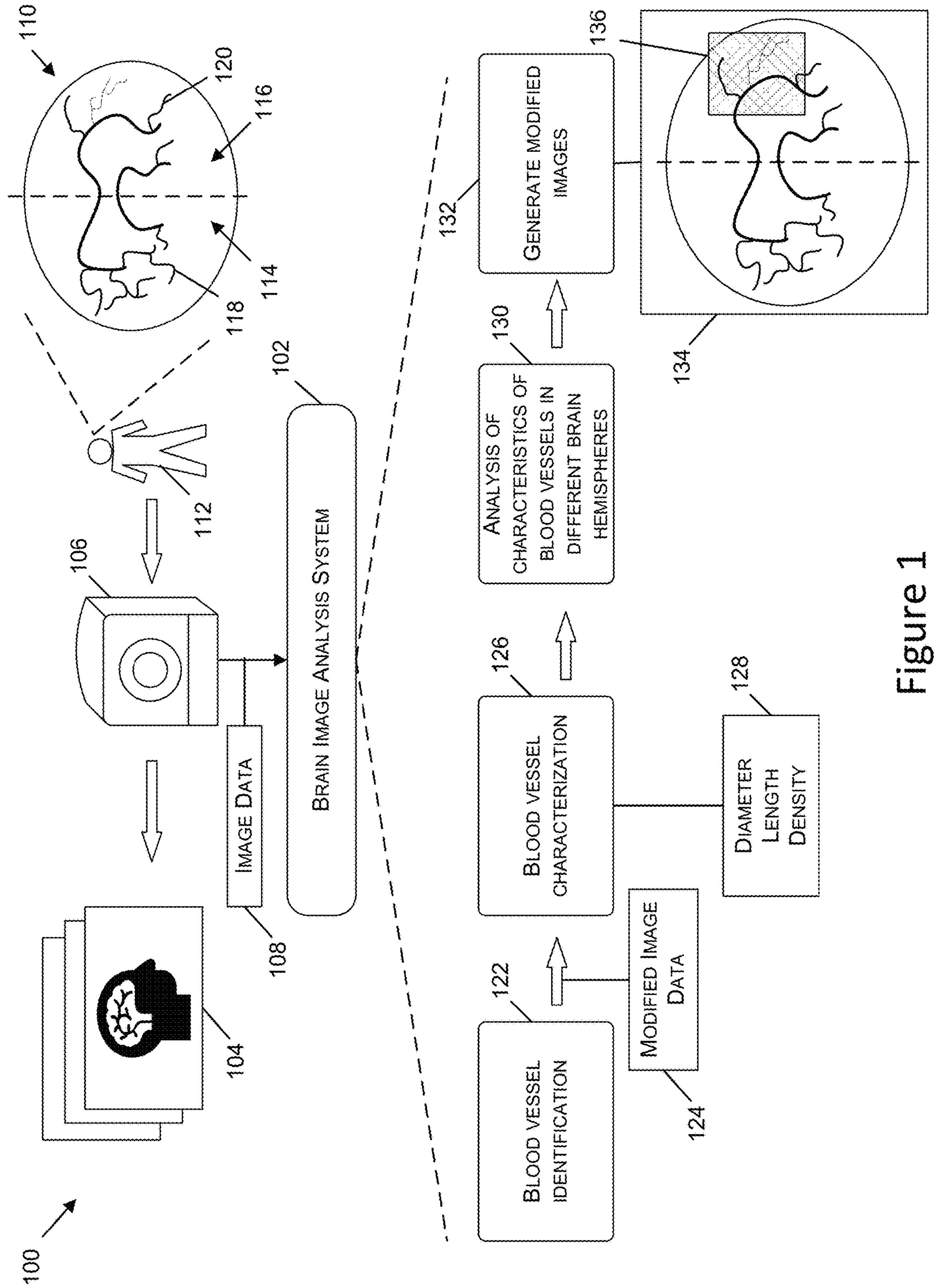
FIG. 1 is a diagram illustrating an example framework to analyze blood vessels of the brain, in accordance with one or more example implementations.

Strokes can be treated through the removal of a blood clot that is disrupting the flow of blood through an artery. Endovascular thrombectomy can be one method used to restore blood flow by removing blood clots in arteries of the brain. Large vessel occlusions (LVO) cause approximately one third of acute ischemic strokes, yet they are responsible for 90% of mortality related to this condition and severe neurological disability in survivors. Endovascular thrombectomy has been shown to decrease disability and improve functional outcomes over standard medical management in patients with an anterior circulation large vessel occlusion. It is therefore the treatment of choice for occlusion of the intracranial internal carotid artery (ICA) or the M1 segment of the middle cerebral artery (M1-MCA), and can be performed safely in carefully selected patients up to 24 hours following stroke onset. In situations where removal of a blood clot is not performed within a window of time for an individual suffering from an LVO, death of brain tissue can occur due to a lack of blood supply, which in turn can lead to severe morbidity and mortality. Thus, prompt diagnosis of LVOs can facilitate beneficial treatment of individuals suffering from this condition.

The systems and techniques described herein are directed to the analysis of blood vessels of the brain using x-ray computed tomography angiographic (CTA) images of contrasted blood vessels in the brain to detect abnormalities of the blood vessels of the brain. One or more additional implementations can implement magnetic resonance angiography (MRA), such as contrast-enhanced MRA, time-of-flight (TOF) MRA, phase-contrast (PC) MRA, or arterial-spin label-based MRA. As used herein "blood vessel" can refer to an entire length of a blood vessel or to a portion of a blood vessel, such as a segment of a blood vessel. In example implementations, the techniques and systems described herein can be used to detect occlusions and severe stenoses of large blood vessels of the brain that result in a stroke. In various examples, images can be generated that indicate abnormalities in the blood vessels of the brain and that can be used to identify individuals that may be in need of prompt treatment for a stroke. In this way, the treatment of individuals can be prioritized based on conditions indicated by the images.

In illustrative implementations, images of a brain of an individual can be obtained. In various examples, the images can include computed tomography angiography (CTA) images of the brain of the patient. The images can be processed and analyzed to identify various anatomical features of the patient's brain. For example, the images can be analyzed to identify bones included in the images. In addition, the images can be analyzed to identify blood vessels included in the images. In various implementations, one or more templates corresponding to features of a human brain, such as but not limited to anatomic regions, can be used to identify the respective features of the brain included in the images.

The blood vessels of the brain can have different diameters and the blood vessels can be characterized according to their diameters. To illustrate, blood vessels of the brain can be classified as having relatively large luminal diameters (e.g., from about 4 mm to about 8 mm) or has having relatively small luminal diameters (e.g., from about 1 mm to less than about 4 mm). In various implementations, the analysis performed to detect abnormalities in the blood vessels of the brain can be based on the diameters of the blood vessels being analyzed.

In example implementations, the data of the CTA images can be represented as voxels and these voxels can be associated with Hounsfield Unit (HU) density values. For visualization purposes, the density associated with a given voxel can be indicated by a grey scale value of the voxel in the image. For example, features with relatively higher densities can have higher grey scale values and appear whiter in the images than features with relatively lower densities that have lower grey scale values and appear darker in the images.

Implementations described herein to detect blood vessel abnormalities can determine differences between the densities of blood vessels that are located in each hemisphere of the brain. For example, a density of a segment of the internal carotid artery in a first hemisphere of the brain can be compared with a density corresponding to a segment of the internal carotid artery in a second hemisphere of the brain. The extent of the differences between symmetrically located blood vessels in the different hemispheres of the brain can indicate a probability that there is an abnormality associated with a blood vessel segment. In situations where the differences between the densities of symmetrically located blood vessels in different hemispheres of the brain are greater than a threshold difference, the probability that an abnormality in the blood vessel segment having the lower density values can be greater than a threshold probability. As a result, additional images can be generated that include the blood vessels of the brain of the individual and that highlight the blood vessels that may be associated with an abnormality. These additional images can be provided to one or more clinicians for review to determine treatment for individuals.

In one or more additional implementations, the presence of an LVO can be determined without a comparison between densities of blood vessels in different hemispheres of the brain. For example, an anatomic template indicating large blood vessels of the brain can be aligned with an image of a brain of a patient. In these scenarios, density values in HU are analyzed in the regions of the brain of the patient that correspond to one or more locations of the large blood vessels. In various examples, iodine can be used as a contrast medium that is provided to the blood vessels of the patient. The contrast medium can indicate locations of blood vessels in contrast to other brain tissue. In one or more examples, the HU values for a number of locations of a blood vessel can be compared to one or more threshold HU values. In situations where the HU values at one or more locations within the brain of the patient are less than a threshold value, an LVO may be detected. The inference of the presence of an abnormal blood vessel can be used to automate actions in the care of patients. For example, computer algorithms use the output of implementations described herein as their input to trigger alerts to clinicians at another hospital or prioritize review of this patient's CTA by a radiologist/clinician.

Accordingly, the implementations described herein can identify possible abnormalities in blood vessel segments of the brain in an automated manner. The possible abnormalities can be visually depicted in images that can be provided to clinicians and indicate an urgency with respect to review of the images by the clinicians. In this way, the amount of time between onset of a condition, such as a stroke, and the diagnosis by a clinician based on images of the brain of an individual is minimized. Further, the amount of time between onset of the condition and the individual receiving treatment for the condition can also be minimized. Further, clinicians at a specialized center who might need to take over care of a patient from a hospital that cannot provide ECR, can be alerted of an ECR-candidate patient early than through standard-of-care channels. In this way, the amount of damage to tissue of individuals for which blood flow may be inhibited due to blockage or narrowing of blood vessels in the brain of the individual can be minimized.

FIG. 1 is a diagram illustrating an example framework 100 to analyze blood vessels of the brain, in accordance with one or more example implementations. The framework 100 can include a brain image analysis system 102. The brain image analysis system 102 can analyze images of brains of individuals and identify possible biological conditions relating to the brains of the individuals. In various implementations, the brain image analysis system 102 can analyze images of brains of individuals to identify abnormalities in blood vessels of the brains of the individuals. For example, the brain image analysis system 102 can analyze characteristics of blood vessels located in the brain to determine probabilities that individuals have a biological condition that can adversely affect brain function. To illustrate, the brain image analysis system 102 can analyze characteristics of blood vessels located in the brain to determine probabilities that individuals are suffering from a stroke. In illustrative examples, the brain image analysis system 102 can analyze characteristics of blood vessels located in the brain to identify large vessel occlusions. As used herein in one or more implementations, the term “proximal” can refer to locations that are relatively near a midline of the brain of an individual and the term “distal” can refer to locations of the brain of the individual that are increasingly distant from the midline.

The brain image analysis system 102 can obtain data related to a number of images 104. The images 104 can include features located in the heads of individuals. In example implementations, the images 104 can indicate features that are internally located within the heads of individuals, such as bones, blood vessels, muscle, and the like. For example, the images 104 can include brains of individuals, blood vessels that circulate blood into and out of the brains, and bones located in the heads of the individuals, such as the skull base and the calvarium.

The images 104 can be captured by an imaging device 106. The imaging device 106 can utilize one or more imaging technologies to capture the images 104. In illustrative examples, the imaging device 106 can include an x-ray computed tomography (CT) imaging device. In example implementations, the imaging device 106 can include a computer tomography angiography (CTA) imaging device. In additional illustrative examples, the imaging device 106 can include a computed tomography perfusion (CTP) imaging device. The data generated by the imaging device 106, which can be used by one or more processing devices to produce the images 104 on a display device, can be provided to the brain image analysis system 102 as image data 108. The image data 108 can be formatted according to a specified standard. For example, the image data 108 can be formatted according to a Digital Imaging and Communications in Medicine (DICOM) standard. The image data 108 can be communicated to the brain image analysis system 102 via one or more networks or via one or more portable memory storage devices (e.g., a flash drive). Additionally, the image data 108 can be accessible to the brain image analysis system 102 via a website or via a cloud computing service provider. In various scenarios, the image data 108 can include data generated by one or more imaging techniques. To illustrate, the image data 108 can include data generated using CTA imaging techniques and CTP imaging techniques.

In illustrative implementations, the imaging device 106 can capture one or more images 104 that include a brain 110 of an individual 112. The brain 110 of the individual 112 can include a first hemisphere 114 and a second hemisphere 116. The features of the brain 110 located in the first hemisphere 114 can be arranged substantially symmetrical with respect to the features of the brain 110 located in the second hemisphere 116. For example, a blood vessel 118 located in the first hemisphere 114 can have a counterpart blood vessel 120 located in the second hemisphere 116 at a substantially symmetrical position. In one or more illustrative examples, blood vessels located in the first hemisphere 114 can be referred herein to as contralateral blood vessels and blood vessels located in the second hemisphere 116 can be referred to herein as ipsilateral blood vessels.

The brain image analysis system 102 can perform a number of operations in the analysis of the images 104 to determine probabilities that individuals have various biological conditions based on the features shown in the images 104. For example, at operation 122, the brain image analysis system 102 can perform blood vessel identification. In example implementations, the brain image analysis system 102 can identify features of the images 104 that do not correspond to blood vessels included in the brains of individuals and remove those features to generate modified image data 124. The modified image data 124 can include portions of the data associated with the images 104 that remain after the brain image analysis system 102 has removed some of the data associated with the images 104. The modified image data 124 can be used to generate modified images of the brains of the individuals that do not include one or more features that were included in an original set of images. For example, the brain image analysis system 102 can identify portions of a neck included in an image 104 and remove data corresponding to the portions of the neck. That is, the brain image analysis system 102 can delete data corresponding to portions of the image 104 that are part of a neck of an individual. The brain image analysis system 102 can also identify portions of the image 104 that do not correspond to blood vessels located in the head of the individual and remove those portions from the images 104. To illustrate, the brain image analysis system 102 can identify bone included in the image 104 and delete data associated with the bone from the image 104 to produce the modified image data 124.

In various implementations, the blood vessel analysis system 102 can utilize one or more templates to identify features located in or around brains of individuals. In examples, the blood vessel analysis system 102 can store or otherwise have access to templates that indicate locations of features associated with brains of individuals. In illustrative examples, the blood vessel analysis system 102 can use templates indicating bone structures located within heads of individuals, such as vertebrae, the calvarium, and the skull base. In additional examples, the blood vessel analysis system 102 can use templates indicating locations of blood vessels in and around the brains of individuals. To illustrate, the templates can indicate locations of the internal carotid artery and the middle cerebral artery.

The templates used by the brain image analysis system 102 can be generated using reference images obtained from a number of individuals that include the brains of the individuals and features associated with the brains of the individuals. Composite images can be produced using the reference images that indicate average or median locations of features included in the images. In various implementations, templates can be generated for specified age groups and/or for individuals that have various biological conditions. For example, reference images can be obtained that include brains of individuals between the ages of 55 and 70. In these situations, one or more templates can be produced from the reference images that indicate locations of features associated with brains of individuals within the 55-70 age group. Additional templates can be produced for individuals between the ages of 40 and 54 that may have features associated with the brain that have different locations than the individuals within the 55-70 age group. In further examples, one or more templates can be produced from reference images that include brains of individuals that have suffered a stroke or individuals with normal variants of brain vasculature such as but not limited to fetal PCAs, hypoplastic or aplastic A1 segments of the ACA or aplastic or hypoplastic vertebral arteries.

In example implementations, templates can be used by the brain image analysis system 102 to determine locations of features associated with the brains of individuals using a registration process. The registration process can align an image 104 with a template to spatially align the image 104 with the template. In example implementations, the brain image analysis system 102 can perform one or more coordinate transformations to align an image 104 with a template. In illustrative examples, the brain image analysis system 102 can determine a feature included in an image 104 that has a threshold amount of alignment with a corresponding feature included in the one or more templates and indicate that the feature included in the image 104 corresponds to the feature of the template. In a specific illustrative example, the brain image analysis system 102 can determine that a feature of an image 104 corresponds to the internal carotid artery of a template. The brain image analysis system 102 can then label the feature of the image 104 as an internal carotid artery. In some examples, the brain image analysis system 102 can generate metadata indicating that the feature included in the image 104 is an internal carotid artery.

In various examples, one or more first templates can be used to identify the ICA located in at least one of the first hemisphere 114 or the second hemisphere 116. Additionally, one or more second templates can be used to identify the M1-MCA located in at least one of the first hemisphere 114 or the second hemisphere 116. Further, one or more third template can be used to identify the M2-MCA and further distal MCA branches located in at least one of the first hemisphere 114 or the second hemisphere 116. In one or more additional examples, blood vessels located in the first hemisphere 114 and the second hemisphere 116 can be determined using one or more machine learning techniques. For example, blood vessels located in the first hemisphere 114 and the second hemisphere 116 can be identified using one or more deep convolutional neural networks.

At operation 126, the brain image analysis system 102 can perform operations related to blood vessel characterization. That is, the brain image analysis system 102 can analyze at least one of the modified image data 124 or the image data 108 and identify blood vessels included in the images 104. The blood vessels included in the image data 108 can be identified using one or more filtering algorithms that identify tubular objects in images. In illustrative examples, the brain image analysis system 102 can identify tubular objects in the images 104 based on analyzing brightness values associated with data points in the image data 108.

The brain image analysis system 102 can also determine a set of characteristics 128 of the blood vessels. For example, the brain image analysis system 102 can determine diameters of blood vessels located in brains of individuals. In additional examples, the brain image analysis system 102 can determine lengths of blood vessels included in brains of individuals. Further, the brain image analysis system 102 can determine densities of blood vessels included in brains of individuals. In various implementations, the densities of blood vessels can be determined using the intensities of the blood vessels in the images 104. To illustrate, the amount of X-rays absorbed by a material can indicate a density of the material and the amount of X-rays absorbed by the material can correspond to the intensity of the material in the images 104. The intensity of features included in the images 104 can also correspond to a measure of opacity of the features.

The brain image analysis system 102 can group blood vessels included in the images 104 according to one or more characteristics of the blood vessels. For example, blood vessels included in the images 104 can be grouped according to the diameters of the blood vessels. Additionally, blood vessels included in the images 104 can be grouped according to the lengths of the blood vessels. In further examples, the blood vessels included in the images 104 can be grouped according to densities of the blood vessels. In illustrative implementations, the brain image analysis system 102 can produce a first group blood vessels having a first range of diameters and a second group of blood vessels having a second range of diameters. In various examples, the brain image analysis system 102 can produce a first group of blood vessels having diameters from at least about 0.2 mm to no greater than about 4 mm and a second group of blood vessels having diameters from at least about 4 mm to no greater than about 10 mm.

The brain image analysis system 102 can, at operation 130, perform an analysis of characteristics of blood vessels in different hemispheres of the brains of individuals. The brain image analysis system 102 can determine the densities of blood vessels having specified diameters and being located in given regions of the brain. For example, the brain image analysis system 102 can determine densities of blood vessels and segments of blood vessels having relatively larger diameters that are located in a first region of the brain. In illustrative scenarios, the brain image analysis system 102 can determine diameters of the supraclinoid ICA. The first region may also include the proximal M1 segment of the middle cerebral artery The brain image analysis system 102 can also determine densities of blood vessels and segments of blood vessels having relatively smaller diameters, such as no greater than about 3.5 mm, that are located in regions of the brain outside of the first region, such as at least a second region of the brain and a third region of the brain. To illustrate, the brain image analysis system 102 can determine diameters of blood vessels located in a second region of the brain that includes the middle to distal portions of the M1 segment of the middle cerebral artery. Additionally, the blood vessels or segments of blood vessels located in a third region of the brain being analyzed by the brain image analysis system 102 can include the M2 and M3 segments of the middle cerebral artery. The M2 segment(s) (e.g., superior, inferior, division) of the middle cerebral artery can also be referred to as the insular segment(s).

After determining densities of blood vessels located in different portions of the brain, identified by the anatomic template or other pre-specified features, the brain image analysis system 102 can compare the densities located in the respective regions across the different hemispheres of the brain or if the location of a vessel has been found via an anatomical template, its absolute HU value. In example implementations, the brain image analysis system 102 can compare HU densities in blood vessels located within the region laid out by the anatomical template of a first hemisphere of the brain of a patient with densities of blood vessels located within a corresponding region of a second hemisphere of the brain of the patient. In one or more illustrative examples, the comparison between blood vessel densities between hemispheres in the brain can include a first region comprising the intracranial artery, a second region comprising the M1 segment of the middle cerebral artery, and a third region comprising the M2 segment of the middle cerebral artery and further distal branches of the middle cerebral artery.

By comparing the densities of blood vessels located in different parts of the brains of an individual across hemispheres, differences between the densities of blood vessels between the hemispheres can be determined. The differences between the densities of blood vessels in different hemispheres can indicate abnormalities associated with the blood vessels. In example implementations, abnormalities of blood vessels located in the brain can correspond to a biological condition. In illustrative implementations, the brain image analysis system 102 can determine differences between densities of blood vessels located in a region of a first hemisphere of the brain of an individual and densities of blood vessels located in a counterpart region of a second hemisphere of the brain of the individual. In situations where the differences in blood vessel differences in counterpart regions of different hemispheres of the brain of an individual are at least a threshold amount, the brain image analysis system 102 can determine that there is at least a threshold probability of an abnormality with respect to the blood vessels in a region of the brain of the individual. The brain image analysis system 102 can determine that an abnormality is present with respect to blood vessels located in a region of the brain of an individual in situations where a region located in a first hemisphere of the brain of the individual has a blood vessel density that is less than a threshold amount with respect to the density of blood vessels located in a counterpart region of a second hemisphere of the brain of the individual. That is, the probability of an abnormality with respect to a blood vessel in the brain of an individual can increase as the density of blood vessels is reduced from one hemisphere with respect to the other hemisphere.

In some implementations, the brain image analysis system 102 can determine differences in blood vessel densities in multiple regions across hemispheres of brains of individuals, while in other situations, the brain image analysis system 102 can determine differences in blood vessel densities in a single region across hemispheres of brains of individuals. In various implementations, the number of regions for which the brain image analysis system 102 performs comparisons across hemispheres of brains can be based on amounts of differences between densities of blood vessels located in counterpart regions of the brains of individuals and/or based on the regions in which at least threshold amounts of differences between blood vessel densities are present.

The brain image analysis system 102 can, at 132, generate modified images of the brains of individuals. The modified images can be generated based at least in part on the modified image data 124. In various implementations, the modified images can indicate blood vessels of the brains of individuals. The modified images can also indicate differences in blood vessel densities in different parts of the brains of the individuals. In illustrative implementations, the brain image analysis system 102 can generate images that indicate regions of the brains of individuals that can be associated with various probabilities of the presence of abnormal blood vessels. The brain image analysis system 102 can also generate images that indicate regions of the brains of individuals that indicate that individuals have a biological condition. In the illustrative examples, the brain image analysis system 102 can generate a modified image 134 that includes blood vessels of the brain 110 of the individual 112. The modified image 134 also includes a user interface element 136 that indicates a region of the brain 110 of the individual 112 that includes blood vessels that the brain image analysis system 102 has determined to have at least a threshold probability of being abnormal and/or a region of the brain 110 of the individual 112 that includes blood vessels with characteristics that correspond to the presence of a biological condition with respect to the individual 112. The user interface element 136 can be an overlay that is displayed with respect to the brain 110 of the individual 112. In one or more illustrative examples, the modified images produced by the brain image analysis system 102 can, in various scenarios, include maximum intensity projections (MIP).

Figure 2:
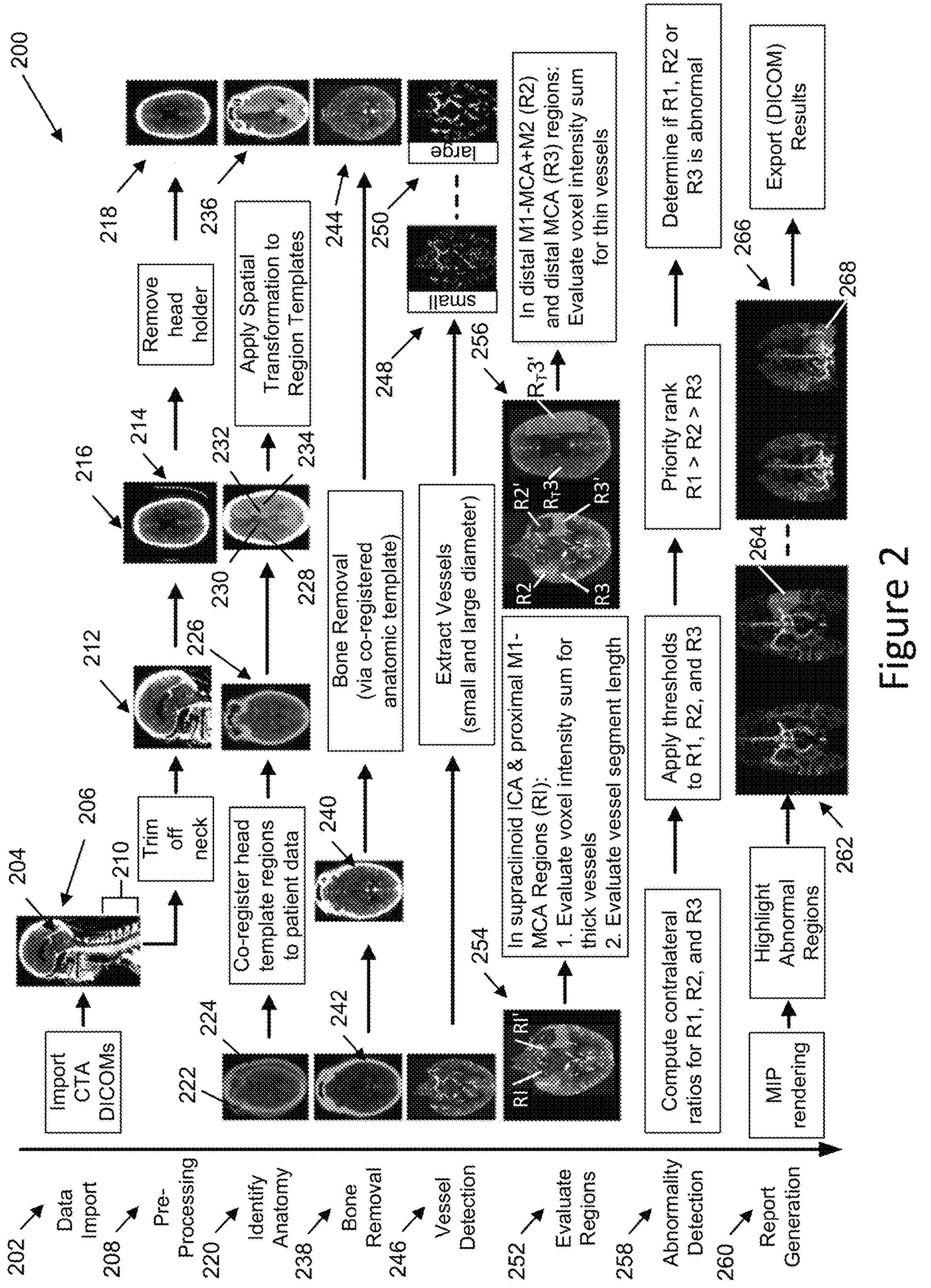
FIG. 2 is a pictorial diagram illustrating an example process to analyze blood vessels of the brain and generate one or more images of the blood vessels based on the analysis, in accordance with one or more example implementations.

FIG. 2 is a pictorial diagram illustrating an example process 200 to analyze blood vessels of the brain and generate one or more images of the blood vessels based on the analysis, in accordance with one or more example implementations. In the illustrative example of FIG. 2 a number of operations are indicated that can be performed with respect to an image, captured by an imaging device, of an individual that includes the brain of the individual and FIG. 2 indicates a number of example images indicating the results of the operations being performed on the image.

In particular, FIG. 2 includes a pictorial description of automatic large vessel occlusion (LVO) detection algorithm. After (1) importing raw, thin-slice CT angiographic (CTA) images in Digital Imaging and Communications in Medicine (DICOM) format, (2) only slices above CI are used for further processing, and the CT head holder is removed. A (3) CT head template is then co-registered to the patient's CTA and subsequently the CTA analysis regions (which were previously defined on the CT template) are spatially transformed onto the patient's CTA scan. Next, all bone is removed (4). Tubular filters are applied (5) to extract vessels. Then, (6) the density (in Hounsfield units) sum of all voxels constituting the large vessels and the density sum of all voxels constituting distal vessels are computed and (7) hemispheric comparisons are made. (8) Areas, where the vessel density sum drops below prespecified threshold, are highlight as color overlays on maximum intensity projections. ICA indicates internal carotid artery; and MCA, middle cerebral artery. This process is described in more detail below.

At operation 202, the process 200 includes a data import operation. The data import operation can include obtaining image data corresponding to one or more images that include a brain 204 of an individual. The image data can be formatted according to the DICOM standard. In addition, the image data can be obtained from an imaging device that generates data using computed tomography angiography (CTA) imaging technologies. In the illustrative example of FIG. 2, the image data can be used to produce an image 206 that includes the brain 204 of an individual in addition to other body parts of the individual, such as a skull, teeth, jaw, vertebrae, and so forth. In example implementations, the data representing the images can be represented as voxels. Individual voxels can have a location in three-dimensional space and the individual voxels can encode information that corresponds to the respective locations of the voxels. In illustrative examples, the voxels included in the image data can encode an intensity of the X-rays detected with respect to the respective locations corresponding to the individual voxels. The hallmark of a CTA examination is the administration of an exogenous contrast material that is x-ray attenuating, such as iodine, into the blood stream of the patient. The iodine in blood vessels will attenuate x-rays and increases the natural conspicuity of a blood vessel, thus making it easier for one to tell it apart from normal tissue.

The process 200 can also include, at operation 208, pre-processing operations with respect to the image data that has been imported. For example, a portion 210 of the images 206 that is below the head of the patient and includes the patient's neck can be trimmed from the image data. In various implementations, the portions of the image data that do not correspond to the head of the individual can be identified and deleted or moved out of one or more data volumes that include the image data. An image 212 can be produced after the data corresponding to the portion 210 has been removed. Additionally, data corresponding to a head holder 214 shown in an image 216 can also be removed during preprocessing and the remaining data can be used to produce an image 218 that does not include the head holder 214. The head holder 214 can be a part of the imaging device and can be used to hold the head of the patient during the imaging process used to capture the image data. Preprocessing images can also include applying one or more motion correction and/or one or more head tilt correction techniques to the initial images obtained using one or more imaging technologies.

In addition, at operation 220, the process 200 can include identifying portions of the anatomy of the individual from at least a portion of the image data. One or more templates can be used to identify various anatomical portions of the individual. In the illustrative example of FIG. 2, a first template 222 and a second template 224 that correspond to head portions of a human can be aligned with the portions of the head of the patient included in the image data using one or more image registration techniques. An image 226 can be produced after aligning the first template 222 and the second template 224 with the image data of the patient. A third template 228, a fourth template 230, a fifth template 232, and a sixth template 234 can also be used to identify regions of the brain 204 of the individual. That is, the third template 228 can correspond to a region of the brain 204 of the individual, the fourth template 230 can correspond to an additional region of the brain 204 of the individual, the fifth template 232 can correspond to another region of the brain 204 of the individual, and the sixth template 234 can correspond to a further region of the brain 204 of the individual. One or more spatial transformations can be performed using the templates 228, 230, 232, 234 with respect to the image data of the individual. An image 236 can be produced after the templates 228, 230, 232, 234 are aligned with the image data of the individual, where the image 236 indicates the regions of a human brain with respect to the brain 204 of the individual.

At operation 238, the process 200 can include a bone removal process where portions of the image data that correspond to bone, such as the feature indicated by 240, can be removed from the image data. In example implementations, the bone 240 can be identified using one or more templates 242 that indicate bones located in a human head that have been registered with the image data of the individual. After the data corresponding to the bone 240 has been identified, the data corresponding to the bone 240 can be removed from the image data. An image 244 can be produced that corresponds to the remaining portions of the image data after the portions of the image data corresponding to the bone 240 (and the head holder and neck) have been removed from the original image data.

The process 200 can include, at operation 246, detecting blood vessels located in or near the brain 204 of the individual using the image data. The blood vessels can be detected by applying one or more techniques to identify tubular objects included in the image data. In illustrative examples, the blood vessels can be detected by one or more filtering techniques that identify tubular objects based on an amount of contrast between a given voxel and background voxels. Additionally, one or more templates can be used to determine the locations of blood vessels in the brain. Further, the blood vessels can be grouped according to the diameters of the blood vessels. For example, the blood vessels included in the image data can be divided into a first group having relatively small diameters and a second group having relatively large diameters. In various implementations, without loss of generality, the first group of blood vessels can have diameters from at least about 0.2 mm to no greater than about 3 mm and the second group of blood vessels can have diameters from at least about 3 mm to no greater than about 10 mm. Image 248 includes a group of relatively small blood vessels and image 250 includes a group of relatively larger blood vessels of the brain 204.

Further, at operation 252, the process 200 can include evaluating the blood vessels included in different regions of the brain 204. In addition, different analyses can be performed with respect to the blood vessels in different regions of the brain 204. An image 254 indicates a first region located in a first hemisphere of the brain 204 as R1 and a counterpart first region located in the second hemisphere of the brain 204 as R1'. R1 and R1' can be arbitrarily shaped, include one or more blood vessels, and/or one or more segments of blood vessels. For example, R1 and R1' can include at least one of one or more segments of the internal carotid artery or one or more segments of the middle cerebral artery. In example implementations, R1 and R1' can include intracranial portions of the internal carotid artery and proximal portions of the M1 segment of the middle cerebral artery. In various implementations, evaluating the regions at 252 can include determining intensities of voxels corresponding to blood vessels located in region R1 having relatively large diameters. In addition, the intensities of the voxels that correspond to blood vessels located in region R1 that have relatively large diameters can be aggregated to determine a sum of these intensities. Further, the sum of the intensities of the voxels that correspond to blood vessels located in region R1 that have relatively large diameters can be evaluated with respect to the lengths of the blood vessels located in region R1 that have relatively large diameters.

Evaluating characteristics of blood vessels included in the brain 204 of the individual at 252 can also include analyzing characteristics of blood vessels included in a second region shown as R2 in image 256 and a third region shown as R3 in image 256. Regions R2 and R3 can be arbitrarily shaped and are located in a first hemisphere of the brain 204. Additionally, image 256 also indicates a counterpart second region R2' and a counterpart third region R3' located in a second hemisphere of the brain 204. The image 256 also includes overlays that correspond to regions of one or more templates that can be used to identify and/or group blood vessels in the brain 204. To illustrate, the image 256 indicates a first template region $R_T3$ located in the first hemisphere of the brain 204 and a second template region $R_T3'$ located in the second hemisphere of the brain 204. In example implementations, the second region R2 and the counterpart second region R2' can include distal portions of the M1 segment of the middle cerebral artery and portions of the M2 segment of the middle cerebral artery. Further, the third region R3 and the counterpart third region R3' can include more distal segments of the middle cerebral artery, such as the M3 segment of the middle cerebral artery and, possibly, the M4 segment of the middle cerebral artery. The blood vessels included in regions R2, R3, R2', and R3' can have relatively smaller diameters with respect to the diameters of the blood vessels included in the regions R1 and R1'. In various implementations, evaluating the characteristics of blood vessels at 256 that are included in regions R2, R3, R2', and R3' can include determining the HU intensities of voxels that correspond to the blood vessels located in regions R2, R3, R2', and R3'. In some illustrative examples, a sum of the intensities of the voxels corresponding to the blood vessels located in the respective regions R2, R3, R2', and R3' can be determined. That is, a sum of intensities of the voxels corresponding to the blood vessels located in region R2 can be determined, a sum of intensities of the voxels corresponding to the blood vessels located in region R3 can be determined, a sum of intensities of the voxels corresponding to the blood vessels located in region R2 can be determined, and a sum of intensities of the voxels corresponding to the blood vessels located in region R3' can be determined.

The process 200 can, at operation 258, include performing operations to determine whether or not an abnormality is present in the blood vessels of the brain 204. Determining whether an abnormality is present in blood vessels of a region of the brain 204 can include determining ratios of intensities of blood vessels across hemispheres of the brain 204. For example, a first ratio can be determined that indicates differences between the intensities of the voxels corresponding to blood vessels located in R1 with respect to the intensities of the voxels corresponding to blood vessels located in R1'. In addition, a second ratio can be determined that indicates differences between the intensities of the voxels corresponding to blood vessels located in R2 with respect to the intensities of the voxels corresponding to blood vessels located in R2'. Further, a third ratio can be determined that indicates differences between the intensities of voxels corresponding to blood vessels located in R3 with respect to the intensities of the voxels corresponding to blood vessels located in R3'.

The determination of differences between intensities of voxels corresponding to blood vessels located in different regions across hemispheres of the brain 204 can identify differences in blood vessel densities in the individual regions across the hemispheres of the brain 204. In situations where the differences in densities in blood vessels located in substantially symmetrically located regions in different hemispheres of the brain 204 are greater than one or more threshold differences, then an abnormality can be present. In various implementations, after determining the ratios indicating differences between intensities of voxels in counterpart regions in different hemispheres of the brain 204, the ratios can be compared to thresholds for the individual regions. The thresholds can indicate probabilities of abnormalities being present with respect to blood vessels. In case single locations are used instead of hemispheric ratios, either absolute or relative changes to HU values under normal vessel opacification with typical amounts of iodine contrast material in the blood streams can be assessed. These normal HU values of iodine opacification can be between 200 and 300 HU, taken from literature values or reference values from a large vessel of each patient, such as the aortic arch.

In an illustrative example, a schema of thresholds can be implemented in the detection of abnormalities of blood vessels associated with the brain 204. For example, the schema can include multiple tiers with a first tier indicating a mild reduction in blood vessel density for counterpart regions located in different hemispheres of the brain 204 and digressing to a last tier indicating the greatest difference in blood vessel density between counterpart regions in different hemispheres of the brain 204. In example implementations, a first tier of a schema can correspond to a reduction in blood vessel density between a region located in a first hemisphere of the brain 204 and a counterpart region located in a second hemisphere of the brain 204 from at least about 80% up to about 100%. Additionally, a second tier of a schema can correspond to a reduction in blood vessel density between a region located in a first hemisphere of the brain 204 and a counterpart region located in a second hemisphere of the brain 204 from at least about 75% to no greater than about 80%. A third tier of a schema can correspond to a reduction in blood vessel density between a region located in a first hemisphere of the brain 204 and a counterpart region located in a second hemisphere of the brain 204 from at least about 60% to no greater than about 74%. A fourth tier of a schema can correspond to a reduction in blood vessel density between a region located in a first hemisphere of the brain 204 and a counterpart region located in a second hemisphere of the brain 204 from at least about 45% to no greater than about 59%. Further, a fifth tier of a schema can correspond to a reduction in blood vessel density between a region located in a first hemisphere of the brain and a counterpart region located in a second hemisphere of the brain 204 of no greater than about 45%. Although an illustrative example of a schema is described above, various other values for the number of tiers, threshold levels and ranges can be chosen.

The threshold applied to determine an abnormality in blood vessels can be different for different regions. In an illustrative example, a threshold for detecting an abnormality in one region of the brain 204 can correspond to one tier of a schema, while a threshold for detecting an abnormality in another region of the brain 204 can correspond to another tier of the schema. In an additional illustrative example, a threshold for detecting an abnormality of blood vessels in the R1 or the R1' region of the brain 204 can be from at least about a 60% to no greater than a 75% reduction in blood vessel density between at least one pair of counterpart blood vessels located in regions R1 and R1'. In further illustrative examples, a threshold for detecting an abnormality of blood vessels in the R2 or the R2' region of the brain 204 can be no greater than about a 45% reduction in blood vessel density between at least one pair of counterpart blood vessels located in regions R2 and R2'.

In various implementations, the regions of the brain 204 can be assigned priorities such that comparisons between densities of blood vessels across hemispheres is not performed in some regions until a threshold reduction in blood vessel density across hemispheres in another region is satisfied. To illustrate, differences in blood vessel densities between regions R2 and R2' may not be determined unless a difference in blood vessel densities between regions R1 and R1' is within a threshold range of differences. In addition, differences in blood vessel densities between regions R3 and R3' may not be determined unless a difference in blood vessel densities between regions R2 and R2' is within a threshold range of differences. Based on amounts of reduction in blood vessel densities in one or more of the regions R1, R2, R3, R1', R2', or R3', an abnormality can be detected in the brain 204 of the individual.

In additional implementations, in scenarios where differences between blood vessel densities in the R1 and R1' regions are greater than a first threshold density, the comparative analysis of blood vessel densities between brain hemispheres may stop and an abnormality in a blood vessel located in the R1 or R1' region can be inferred. In situations where the blood vessel densities in the R1 and R1' regions are less than the first threshold density, an analysis of the differences in blood vessel densities between regions R2 and R2' can be performed. In these situations, differences between blood vessel densities in the R2 and R2' regions may be determined. If densities between blood vessels of the R2 and R2' regions are greater than a second threshold density, the comparative analysis of blood vessel densities between brain sequence hemispheres may stop and an abnormality in a blood vessel located in the R2 or R2' regions can be inferred. In various examples, the second threshold density can be different from the first threshold density. In scenarios where the blood vessel densities in the R2 and R2' regions are less than the second threshold density, blood vessel density in the R3 and R3' regions may be analyzed to determine whether or not abnormalities are present in one or more blood vessels located in the R3 or R3' regions of the brain 204. In this way, a progressive analysis can be performed where an initial comparative analysis between relatively symmetric regions located in the respective hemispheres of the brain 204 are analyzed and an comparative analysis of additional regions of the brain 204 are not performed unless an abnormality is not found in a preceding pair of regions.

At operation 260, the process 200 can include generating reports that indicate possible regions in the brain 204 of the individual where an abnormality in the blood vessels may be present. In implementations, data that can be used to produce maximum intensity projection (MIP) images can be generated. The MIP images can include features of the brain 204 of the individual. For example, the MIP images can include blood vessels of the brain 204 of the individual. In various implementations, the data used to generate the MIP images can be a subset of the initial image data obtained at 202. In example implementations, the data used to generate the MIP images can include the initial data imported at 202 with portions of the initial data removed that correspond to features of the body of the individual other than the head, portions of the head that correspond to bone, and features that are located outside of the body of the individual, such as the head holder of the imaging device used to generate the initial image data.

Further, regions of the brain 204 that may include a blood vessel abnormality can be highlighted. In some implementations, one or more overlays can be generated that indicate one or more regions of the brain 204 that may include a blood vessel abnormality. In illustrative examples, a color of the overlay can correspond to at least one of a probability or a severity of an abnormality in a blood vessel of the brain 204 of the individual. In illustrative implementations, a blue color can correspond to a reduction in blood vessel densities between hemispheres for a brain region from at least about 75% to no greater than about 80%. Additionally, a green color can correspond to a reduction in blood vessel densities between hemispheres for a brain region from at least about 60% to no greater than about 75% and a yellow color can correspond to a reduction in blood vessel densities between hemispheres for a brain region from at least about 45% to no greater than about 60%. Further, a red color can correspond to a reduction in blood vessel densities between hemispheres for a brain region of no greater than 45%. In various examples, a reduction in blood vessel densities between hemispheres for a brain region that is greater than 80% may not be indicated by a color in the images. In the illustrative example of FIG. 2, an image 262 includes a highlighted portion 264 indicating a possible blood vessel abnormality in the region corresponding to the highlighted portion 264. The illustrative example of FIG. 2 also includes an image 266 having a highlighted portion 268 indicating a possible blood vessel abnormality in the region corresponding to the highlighted portion 268.

After the data for the MIP images is generated, the data can be exported and used to generate user interfaces that can be displayed to a clinician. The data for the MIP images can be formatted according to the DICOM standard. In example implementations, the review of images by a clinician can be prioritized based on the color coding of the overlays included in the images. For example, an image with a red overlay can be prioritized for review ahead of an image with a green overlay and the image with the green overlay can be prioritized for review ahead of an image with a blue overlay or an image with no overlay. The prioritization of image review based on the results of the process 200 can minimize the amount of time between onset of a biological condition relating to blood vessel abnormalities in brains of individuals and treatment being provided to the individuals. Thus, the adverse effects caused by the abnormalities can also be minimized.

Figure 3:
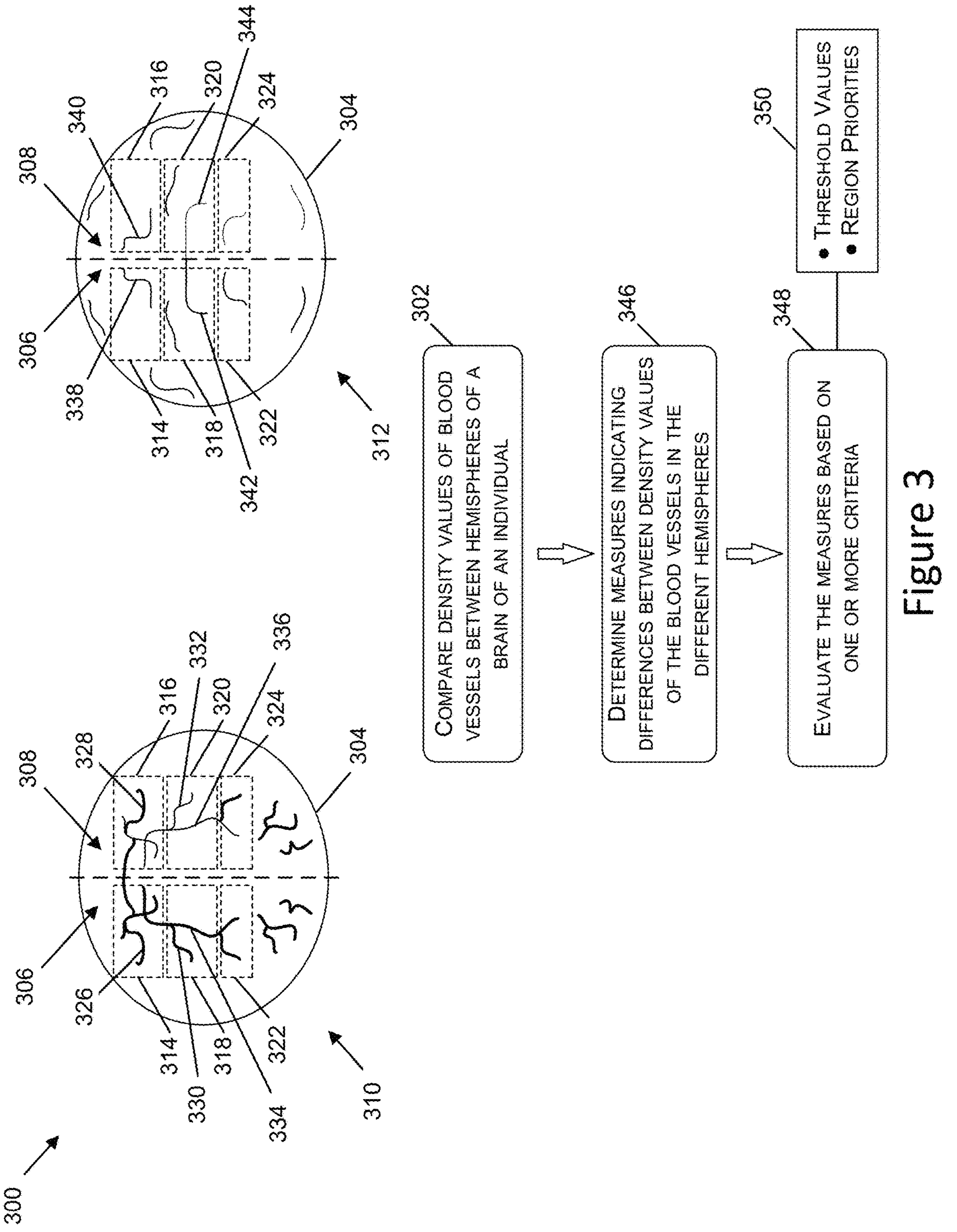
FIG. 3 is a diagram illustrating an example framework to analyze blood vessels located in one hemisphere of the brain in relation to additional blood vessels located in another hemisphere of the brain, in accordance with one or more example implementations.

FIG. 3 is a diagram illustrating an example framework 300 to analyze blood vessels located in one hemisphere of the brain in relation to additional blood vessels located in another hemisphere of the brain, in accordance with one or more example implementations. The framework 300 can include, at operation 302, comparing density values of blood vessels between hemispheres of a brain 304 of an individual. To illustrate, the brain 304 can include a first hemisphere 306 and a second hemisphere 308. The illustrative example of FIG. 3 includes a first depiction 310 that includes blood vessels of the brain 304 having blood vessels with diameters that are included in a first range of values and a second depiction 312 that includes blood vessels of the brain 304 having blood vessels with diameters that are included in a second range of values. In various implementations, at least a portion of the diameters included in the first range of values can be greater than the diameters included in the second range of values. In illustrative examples, the diameters included in the first range of values shown in the depiction 310 can be from at least about 3 mm to no greater than about 8 mm, from at least about 3.5 mm to no greater than about 9 mm, from at least about 4 mm to no greater than about 10 mm, or from at least about 3.2 mm to no greater than about 10.5 mm. Additionally, the diameters included in the second range of values shown in the depiction 312 can be from at least about 0.1 mm to no greater than about 3 mm, from at least about 0.3 mm to no greater than about 3.5 mm, from at least about 0.5 mm to no greater than about 4 mm, or from at least about 0.1 mm to no greater than about 2.8 mm.

The brain 304 can be divided into a number of regions with the regions of the first hemisphere 306 having a counterpart region in the second hemisphere 308. For example, the first hemisphere 306 can include a first region 314 and the second hemisphere 308 can have a first counterpart region 316 that corresponds to and is substantially symmetrically located with respect to the first region 314. In addition, the first hemisphere 306 can include a second region 318 and the second hemisphere 308 can include a second counterpart region 320 that corresponds to and is substantially symmetrically located with respect to the second region 318. Further, the first hemisphere 306 can include a third region 322 and the second hemisphere 308 can include a third counterpart region 324 that corresponds to and is substantially symmetrically locate with respect to the third region 322.

In illustrative examples, the first region 314 can include at least a portion of the intracranial inner carotid artery and a proximal portion of the M1 segment of the middle cerebral artery located in the first hemisphere 306 and the counterpart first region 316 can include at least a portion of the intracranial inner carotid artery and a proximal portion of the M1 segment of the middle cerebral artery located in the second hemisphere 308. In additional illustrative examples, the second region 318 can include middle to distal portions of the M1 segment of the middle cerebral artery located in the first hemisphere 306 and the counterpart second region 320 can include middle to distal portions of the M1 segment of the middle cerebral artery located in the second hemisphere 308. In further illustrative examples, the third region 322 can include at least portions of one or more of the M2 segments of the middle cerebral artery located in the first hemisphere 306 and the counterpart third region 324 can include at least portions of one or more of the M2 segments of the middle cerebral artery located in the second hemisphere 308. In various example implementations, the third region 322 can include at least portions of one or more of the M3 segments of the middle cerebral artery located in the first hemisphere 306 and the counterpart third region 324 can include at least portions of one or more of the M3 segments of the middle cerebral artery located in the second hemisphere 308.

Comparing density values of blood vessels between hemispheres of the brain 304 can include determining a density value for individual blood vessels and/or for segments of blood vessels in both hemispheres 306, 308 of the brain 304. For example, a density can be determined for a first blood vessel 326 and a density can be determined for a counterpart first blood vessel 328. Additionally, a density can be determined for a second blood vessel 330 and a density can be determined for a counterpart second blood vessel 332. In further illustrative examples, a density can be determined for a third blood vessel 334 and a density can be determined for a counterpart third blood vessel 336. In still additional illustrative examples, a density can be determined for a fourth blood vessel 338 and a density can be determined for a counterpart fourth blood vessel 340. Also, a density can be determined for a fifth blood vessel 342 and a density can be determined for a counterpart fifth blood vessel 344.

After the density values are determined for the blood vessels 326, 330, 334, 338, 342 and the counterpart blood vessels 328, 332, 336, 340, 344 then the density values can be compared. To illustrate, the density value of the first blood vessel 326 can be compared to the density value of the counterpart first blood vessel 328. Also, the density value of the second blood vessel 330 can be compared to the density value of the counterpart second blood vessel 332. In addition, the density value of the third blood vessel 334 can be compared to the density value of the counterpart third blood vessel 336. Furthermore, the density value of the fourth blood vessel 338 can be compared to the density value of the counterpart fourth blood vessel 340. The density value of the fifth blood vessel 342 can also be compared to the density value of the counterpart fifth blood vessel 344.

In various implementations, a sum of the density values of individual blood vessels located in a region of the brain 304 can be determined and compared to a sum of blood vessel densities in a counterpart region. For example, a sum of the densities of the blood vessels located in the second region 318 can be determined by adding a density of the second blood vessel 330 to the density of the third blood vessel 332 and to the density of the fifth blood vessel 342. Additionally, a sum of the densities of the blood vessels located in the counterpart second region 320 can be determined by adding a density of the counterpart second blood vessel 332 to the density of the counterpart third blood vessel 336 and to the density of the counterpart fifth blood vessel 344. The sum of the blood vessel densities for the second region 318 can then be compared to the sum of the blood vessel densities for the counterpart second region 320.

The framework 300 can also include, at operation 346, determining measures indicating differences between density values of the blood vessels in different hemispheres 306, 308 of the brain 304. In various implementations, the measures indicating the differences between density values of the blood vessels between the hemispheres 306, 308 can include ratios based on the blood vessel density of at least one blood vessel located in a region in the first hemisphere 306 with respect to the blood vessel density of at least one blood vessel located in a counterpart region of the second hemisphere 308. In an illustrative example, a ratio can be determined using a value of the density of the first blood vessel 326 and the value of the density of the counterpart first blood vessel 328. In example implementations, differences between blood vessel densities across the hemispheres 306, 308 can be expressed as a percentage difference. To illustrate, a percentage of difference in the density of at least one blood vessel located in a region of the first hemisphere 306 can be determined with respect to the density of at least one blood vessel located in a counterpart region of the second hemisphere 308. In implementations, a percentage of reduction in density of one or more blood vessels located in one of the hemispheres 306, 308 can be determined with respect to one or more counterpart blood vessels located in the other one of the hemispheres 306, 308. For example, a measure can be determined indicating that the density of the counterpart second blood vessel 332 is 70% of the density of the second blood vessel 330. In another example, a measure can be determined indicating that a sum of densities of the counterpart second blood vessel 332 and the counterpart third blood vessel 336 is 65% of the sum of the densities of the second blood vessel 330 and the third blood vessel 334.

At 348, the framework 300 can include evaluating the measures based on one or more criteria, such as criteria 350. For example, the measures determined at operation 346 can be compared against one or more threshold values. In implementations, the threshold values can indicate a probability of an abnormality with respect to blood vessels of the brain 304. Additionally, the threshold values can indicate a severity of an abnormality with respect to blood vessels of the brain 304. In various implementations, the greater a reduction in density between one or more blood vessels located in one hemisphere 306, 308 with respect to density of one or more counterpart blood vessels located in the other hemisphere 306 308 can indicate at least one of a higher probability of an abnormality being present with respect to blood vessels associated with the brain 304 or a higher severity of an abnormality of blood vessels associated with the brain 304. In illustrative examples, a reduction in density between one or more pairs of counterpart blood vessels located in different hemispheres 306, 308 that is between at least about 45% and no greater than about 60% can indicate at least one of a greater probability of an abnormality of one or more blood vessels being present in the brain 304 or a greater severity of an abnormality of one or more blood vessels associated with the brain 304 than a reduction in density between pairs of counterpart blood vessels located in different hemispheres 306, 308 that is between at least about 75% and no greater than about 80%.

Additionally, priorities for blood vessels related to different regions of the brain 304 can be used to evaluate the measures indicating differences between density values of the blood vessels located in the respective regions. In illustrative examples, measures indicating differences between density values for blood vessels located in the second region 318 and the counterpart second region 320 may not be evaluated unless the differences between density values for blood vessels located in the first region 314 and the counterpart first region 316 satisfy one or more threshold criteria. Further, measures indicating differences between density values for blood vessels located in the third region 322 and the counterpart third region 324 may not be evaluated unless the differences between density values for blood vessels located in the second region 318 and the counterpart second region 320 satisfy one or more threshold criteria. In various implementations, the region priorities can indicate regions of the brain 304 in which blood vessel density differences indicate relatively higher probabilities of an abnormality with respect to blood vessels of the brain than blood vessel density differences in other regions of the brain 304. The region priorities can also indicate regions of the brain 304 in which blood vessel density differences indicate a greater severity of an abnormality in the blood vessels of a region than blood vessel density differences in another region of the brain 304.

Figure 4:
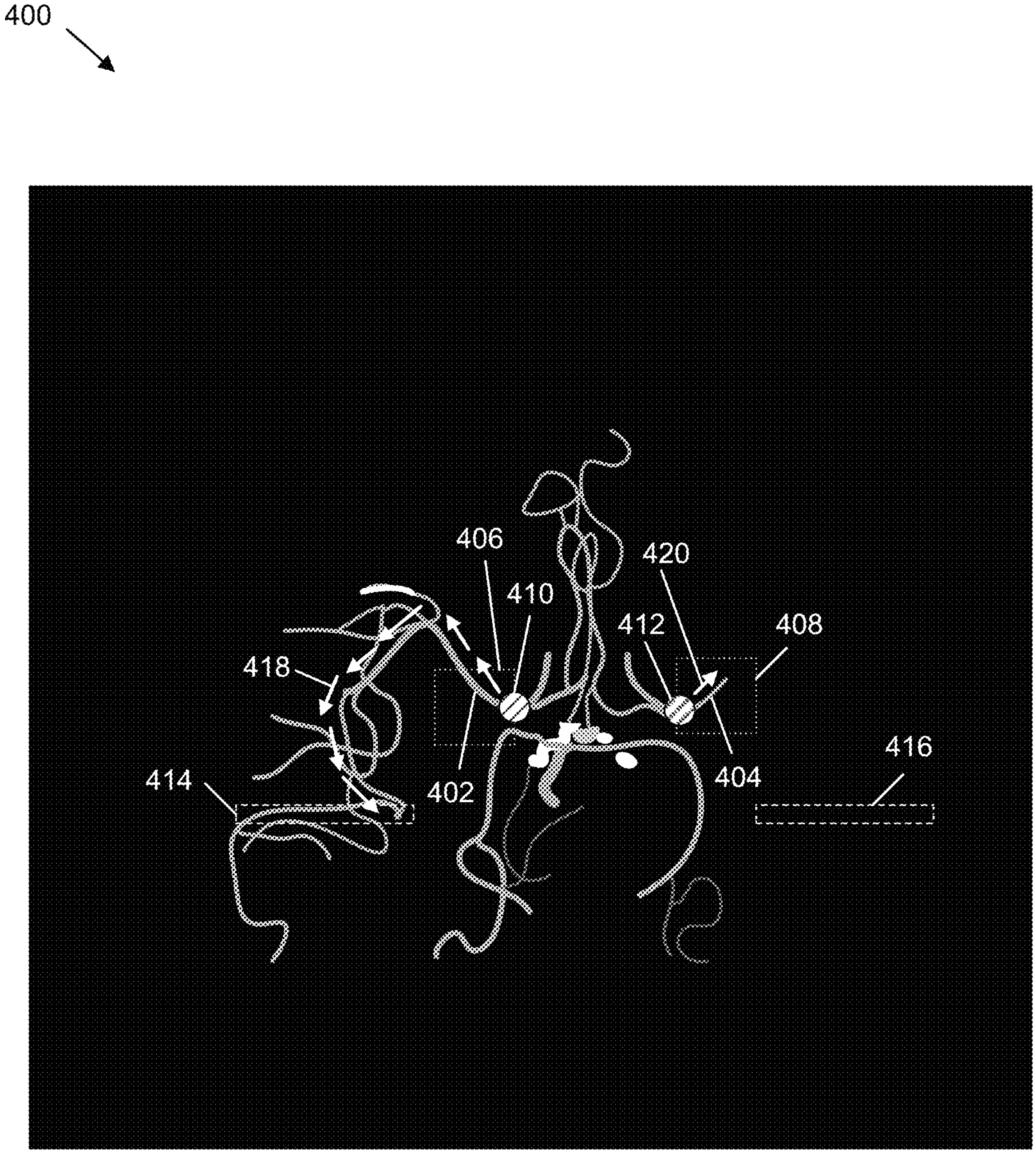
FIG. 4 is a diagram illustrating an example depiction 400 of a process to analyze blood vessels located in the brain of an individual by tracing a path of the vessels, in accordance with one or more example implementations.

FIG. 4 is a diagram illustrating an example depiction 400 of a process to analyze blood vessels located in the brain of an individual by tracing a path of the vessels, in accordance with one or more example implementations. The depiction 400 can indicate blood vessels of the brain by contrast to other portions of the brain. For a contrast agent, such as iodine, can be injected into an individual and imaging techniques, such as CTA, can be performed that indicate the location of the contrast agent within blood vessels of the brain. In one or more implementations, the presence of a blood vessel within the brain can be traced by measuring an amount of contrast between locations in the brain within which contrast agent is found and locations in the brain where contrast agent is absent or is present in amounts that are less than one or more threshold amounts. In various examples, the techniques described with respect to FIG. 4 may be performed in situations when a comparative analysis of blood vessel densities for symmetrically located blood vessels is unable to be performed.

The depiction 400 indicates a number of blood vessels including a first blood vessel 402 and a second blood vessel 404. A path along the blood vessels shown in FIG. 4 can be traced to determine whether or not the path terminates before an expected endpoint. The path of a blood vessel can be traced beginning in a portion of the MCA. In the illustrative example of FIG. 4, the depiction 400 indicates a first MCA region 406 located in a first hemisphere of the brain and a second MCA region located in a second hemisphere of the brain. The first MCA region 406 can located in a proximal end of the MCA in one hemisphere of the brain and the second MCA region 408 can be located in a proximal end of the MCA in a second hemisphere of the brain. Additionally, a first starting point 410 can be located in the first MCA region 406 and can indicate a beginning location by which to trace the first blood vessel 402. Additionally, a second starting point 412 can be located in the second MCA region 408 and can indicate a beginning location by which to trace the second blood vessel 404. The first starting point 410 can be identified by determining a voxel within the first MCA region 406 that has a greatest vesselness value in relation to additional voxels located within the first MCA region 406. As used here, a "vesselness value" can correspond to a probability that a given voxel includes at least a portion of a blood vessel. In addition, the second starting point 412 can be identified by determining a voxel within the second MCA region 408 that has a greatest vesselness value in relation to additional voxels located within the second MCA region 408. The vesselness values for voxels included in at least one of the first MCA region 406 or the second MCA region 408 can indicate an amount of brightness in relative HU with respect to background. In one or more illustrative examples, the vesselness values for voxels included in at least one of the first MCA region 406 or the second MCA region 408 can be determined by calculating eigenvalues of a Hessian filter matrix. The eigenvalues of the Hessian filter matrix can correspond to the change in contrast along the principal eigenvector dimensions computed in the Hessian filter.

An endpoint can also be determined for each blood vessel for which a path is to be tracked. The depiction 400 can include a first endpoint 414 that corresponds to the first blood vessel 402 and a second endpoint 416 that correspond the second blood vessel 404. The first endpoint 414 and the second endpoint 416 can correspond to respective regions of the brain that the MCA distal end passes through to reach distal parts of the brain. In one or more implementations, the depiction 400 indicates a first path 418 along the first blood vessel 402 that terminates at the first endpoint 414. The depiction 400 also indicates a second path 420 along the second blood vessel 404 that terminates before reaching the second endpoint 416.

The first path 418 and the second path 420 can be determined by identifying a least costly path along voxels that begin at the first starting point 410 and the second starting point 412. In one or more examples, the first path 418 can begin at the first starting point 410 and continue by evaluating all possible paths from the first starting point 410 and moving along the path having the current lowest cost. The second path 420 can begin at the second starting point 412 and continue by evaluating all possible paths from the second starting point and moving along the path having the current lowest cost. In various examples, the first path 418 and the second path 420 can be determined by performing a recursive search of the least costly path along the first blood vessel 402 and the second blood vessel 404. Voxels having relatively high vesselness values correspond to locations within the depiction 400 that have a relatively higher amount of contrast with respect to the background and correspond to blood vessels for which the flow of blood is unimpeded. In one or more examples, the cost of moving to a voxel having a vesselness value that is relatively high is less than moving to a voxel having a vesselness value that is relatively low. In various examples, the cost to pass through a voxel that has a vesselness value that is less than a threshold value or a vesselness value that includes or approaches zero can have a very high or infinite cost to pass through.

The search can be terminated when a voxel is reached that is located with an endpoint, such as the first endpoint 414 or the second endpoint 416. In one or more implementations, at least one voxel located in the first endpoint 414 and at least one voxel located in the second endpoint 416 can be labeled as being within the first endpoint 414 or the second endpoint. In these scenarios, detection of a voxel having a label that corresponds to being located in the first endpoint 414 or the second endpoint 416 can terminate the search for the least costly path along the first blood vessel 402 or the second blood vessel 404. Additionally, the search can terminate in response to determining that there are no remaining voxels to move to from a current voxel. For example, the voxels that correspond to the first blood vessel 402 or the second blood vessel 404 that have a finite cost have already been visited and no additional voxels remain for which a finite cost exists. In these situations, the path may terminate before reaching a voxel labeled as being located in an endpoint. In further examples, the search can be terminated in response to determining that a total cost of a current least costly path corresponds to a predefined maximum cost. In at least some situations where the predefined maximum cost is reached, the path may also terminate prior to reaching a voxel labeled as being located in an endpoint. An interruption in blood flow within a blood vessel or more than a threshold amount of narrowing of a blood vessel can be indicated by the termination of a path along a blood vessel before reaching an endpoint for the blood vessel. In these situations, the possible LVO can be indicated on an image of the brain of the patient.

In one or more implementations, the locations of the blood vessels can be determined using one or more templates. To illustrate, the location of the first blood vessel 402 and the location of the second blood vessel 404 can be determined using one or more templates that indicate locations of blood vessels located within the brain. The analysis of the HU values can be performed with respect to the locations of the blood vessels as specified by the one or more templates. In one or more examples, the HU values can be determined within a tolerance range, such as about ±5%, ±10%, ±15%, ±20%, or ±25%, of the location of the blood vessels specified by the one or more templates.

In the illustrative example of FIG. 4, the depiction 400 indicates that the first path 418 starts at the first starting point 410 and moves to a location within the first endpoint 414. Thus, in this situation, the likelihood of an obstruction within the first blood vessel 402 from the first starring point 410 to the first endpoint 414 is relatively low. The depiction 400 also indicates that the second path 420 begins at the second starting point 412 and terminates before reaching the second endpoint 416. Accordingly, in this scenario, the likelihood of an obstruction within the second blood vessel 404 between the second starting point 412 and the second endpoint 416 is relatively high. The techniques described with respect to FIG. 4 can be used to determine abnormalities in blood vessels that may be symmetrically arranged in the hemispheres of the brain, such as the ICA and various portions of the MCA. Further, the techniques described with respect to FIG. 4 may also be used to determine abnormalities in single vessels without symmetry, such as the basilar artery or if occlusions occur over a relatively short segment with reconstitution of blood flow distal/after the clot.

Figure 5:
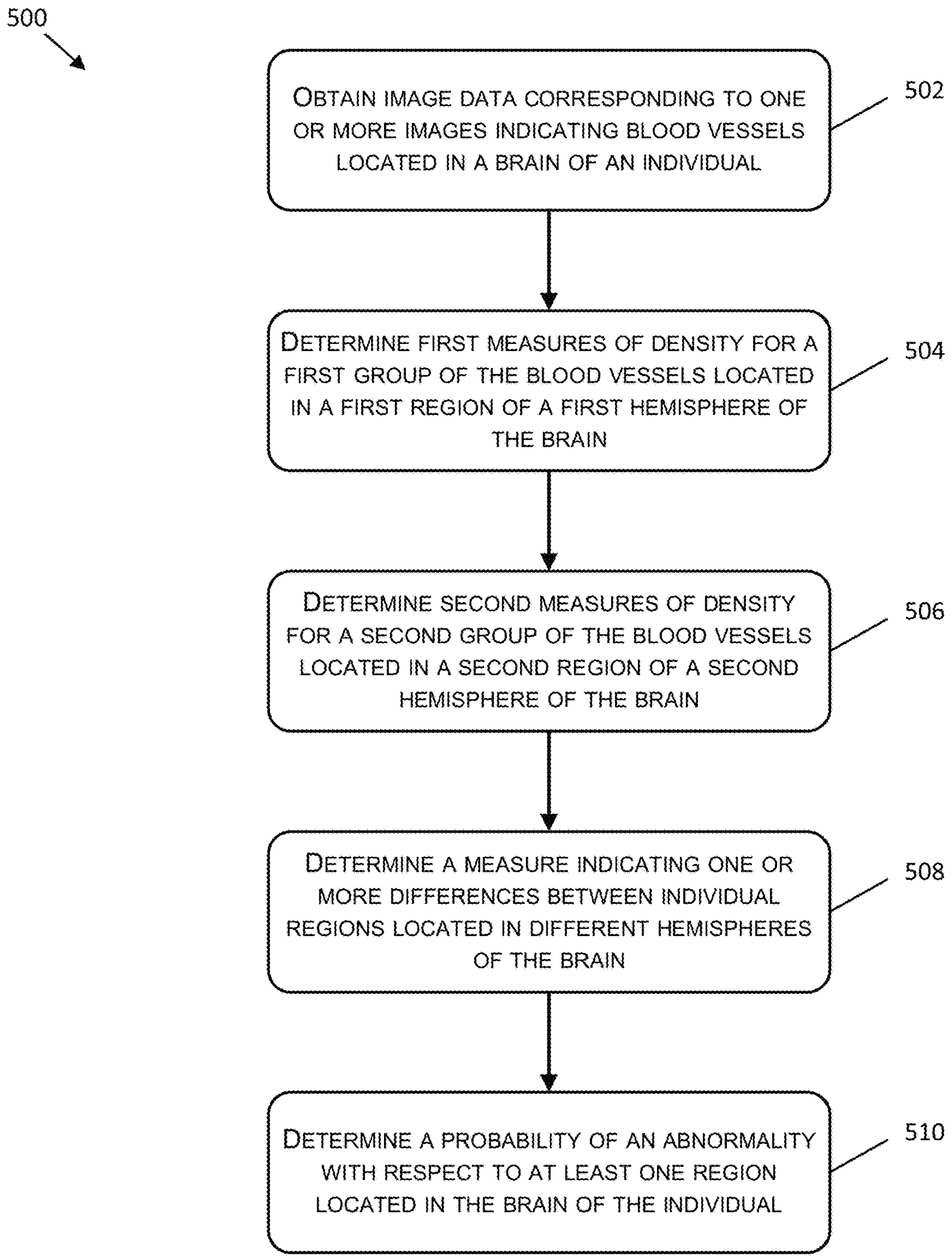
FIG. 5 is a flow diagram of an example process to determine a probability that there is a threshold amount of blockage of a blood vessel in the brain of an individual, in accordance with one or more example implementations.

FIG. 5 is a flow diagram of an example process 500 to determine a probability that there is an abnormality with respect to a blood vessel located in the brain of an individual, in accordance with one or more example implementations. At operation 502, the process 500 can include obtaining image data corresponding to one or more images indicating blood vessels located in a brain of an individual. The image data can be generated by an imaging device, such as a computed tomography (CT) imaging device or a magnetic resonance imaging (MRI) device. In various implementations, the image data can represent the features included in the one or more images as voxels. The voxels can have a location with respect to one another in a three-dimensional space. Additionally, the individual voxels can be associated with an intensity value.

In illustrative examples, a computed tomography imaging device can include a number of X-ray detectors and emit X-rays at various angles that are detected by the X-ray detectors. The image data can be generated by the CT imaging device capturing data in slices at a specified interval. The slices can have thicknesses from at least about 0.5 mm to no greater than about 5 mm and be captured at increments from at least about 0.5 mm to no greater than about 5 mm. The intensity of the X-ray detected at a given detector can be represented in images according to a gray scale. The intensity of a portion of an image can correspond to a density of the material included in the portion of the image. In illustrative examples, the density of the material can be expressed in Hounsfield units and the Hounsfield density of a material can correspond to the physical density of the material. As per convention, materials that are relatively denser can appear as relatively whiter colors in CT images and materials that are relatively less dense can appear as relatively darker colors in CT images. The intensities detected by the CT imaging device can also correspond to an opacity of a material being imaged. In various illustrative examples, the imaging device can include a CT angiography (CTA) imaging device.

In addition, at operation 504, the process 500 can include determining first measures of density for a first group of the blood vessels located in a first region of a first hemisphere of the brain. In illustrative examples, the first region can include at least a portion of the intracranial internal carotid artery and at least a portion of the M1 segment of the middle cerebral artery located in the first hemisphere. The first measures of density for the first group of blood vessels can be based on intensity values included in the image data. The density for an individual blood vessel included in the first group can be determined by adding the intensity values associated with the voxels that correspond to the individual blood vessel. In example implementations, the individual measures of density for the blood vessels included in the first group can be added to produce a sum of the first measures.

The process 500 can include, at 506, determining second measures of density for a second group of the blood vessels located in a second region of a second hemisphere of the brain. The second region can be a counterpart region to the first region. In various implementations, the second region can be located substantially symmetrical with respect to the first region. In illustrative examples, the second region can include at least a portion of the intracranial internal carotid artery and at least a portion of the M1 segment of the middle cerebral artery located in the second hemisphere. The second measures of density for the second group of blood vessels can be based on intensity values included in the image data. The density for an individual blood vessel included in the second group can be determined by adding the intensity values associated with the voxels that correspond to the individual blood vessel. In example implementations, the individual measures of density for the blood vessels included in the second group can be added to produce a sum of the second measures.

At operation 508, the process 500 can include determining a measure indicating one or more differences between individual regions located in different hemispheres of the brain. The measure can indicate differences between the first measures of density and the second measures of density. In various implementations, a difference between density values of individual blood vessels located in the first hemisphere and the second hemisphere can be determined. For example, a difference between a measure of density of the intracranial internal carotid artery located in the first hemisphere and a measure of density of the intracranial internal carotid artery located in the second hemisphere can be determined. In an additional example, a difference between a measure of density of the M1 segment of the middle cerebral artery located in the first hemisphere and a measure of density of the M1 segment of the middle cerebral artery located in the second hemisphere can be determined. In various implementations, a difference between a sum of the first measures of density for the first group of blood vessels and a sum of the second measures of density for the second group of blood vessels can be determined. In example implementations, one or more ratios can be determined to indicate one or more differences between the first measures of density and the second measures of density. To illustrate, ratios corresponding to individual measures of density of the first group of blood vessels with respect to individual measures of density of the second group of blood vessels can be determined. Further, a ratio corresponding to a sum of the first measures of density with respect to a sum of the second measures of density can be determined.

Further, at operation 510, a probability can be determined of an abnormality with respect to at least region located in the brain of the individual. In various implementations, the abnormality can include an occlusion of at least one blood vessel located in the region of the brain of the individual. In illustrative examples, the occlusion can be a large vessel occlusion. Additionally, an occlusion of the at least one blood vessel located in the brain of the individual can be indicative of the individual suffering a stroke.

In implementations, the probability of an abnormality being present with respect to a blood vessel can correspond to differences between densities of blood vessels located in different hemispheres of the brain of an individual. The measure of the amount of difference between vessel densities in the different hemispheres can correspond to the mean vessel signal densities in one hemisphere (e.g., ipsilateral hemisphere) in relation to the mean vessel signal densities in another hemisphere (e.g., contralateral hemisphere). In various implementations, a reduction in the density of a blood vessel can indicate an abnormality with respect to the blood vessel. The reduction in the density of the blood vessel can be identified by comparing the density of the blood vessel with its counterpart blood vessel in the opposing hemisphere. In situations where the density of a first blood vessel located in the first hemisphere of the brain of the individual is at least a threshold amount less than the density of a counterpart blood vessel in the second hemisphere of the brain, the probability that an abnormality may be present in the first blood vessel can be greater than a threshold probability. Additionally, an amount of reduction in the density of a group of blood vessels located in a region of the brain can indicate a probability of an abnormality in at least one of the blood vessels included in the group. To illustrate, an amount of reduction in the sum of density values for a first group of blood vessels included in a region of the first hemisphere of the brain with respect to the sum of density values for a second group of blood vessels included in a counterpart region of the second hemisphere of the brain can indicate a probability of an abnormality being present with respect to at least one blood vessel included in the first group of blood vessels.

In one or more examples, the threshold probability metric can correspond to the vessel density ratio between ipsilateral and contralateral regions of the brain, where a first region can include the ICA, a second region can include the M1-MCA, and the third region can include M2-MCA and further distal MCA branches. In these situations, a vessel density ratio of 1.0 can correspond to equal density between blood vessels of both hemispheres. The threshold for determining an abnormality can be set lower to be less sensitive to an occlusion, but have greater specificity. To illustrate, a relatively low threshold (e.g. 0.3) can mean that the ipsilateral vessel density needs to be severely reduced (i.e. down to 30%) relative to the normal contralateral vessel density in this region. If the vessel density drops by a relatively large amount, the probability of identifying an LVO is relatively high and the likelihood of false detection is relatively low (i.e. high specificity). In these situations, since only those LVOs with severe vessel density reduction will meet the criteria some may be missed. Hence such threshold leads to low sensitivity. Conversely, if the threshold is set to 0.8, a vessel density difference of 80% can be used to identify an LVO. This leads to high sensitivity with this threshold. However, natural hemispheric differences or LVO mimics can also cause a similar blood vessel density change and may lead to false alerts that can reduce specificity for detecting LVOs.

In various implementations, a user interface can be generated that indicates the probability of the abnormality with respect to the at least one blood vessel included in the brain of the individual. In illustrative examples, the user interface can include a maximum intensity projection (MIP) image of the blood vessels of the brain of the individual. The user interface can also highlight one or more regions of the brain of the individual that have the highest probabilities of abnormalities being present in at least one blood vessel. In example implementations, a color of the highlighted region or regions can be indicative of the probability of an abnormality with respect to a blood vessel in a given region. To illustrate, a red highlighted region can have a higher probability of an abnormality being present with respect to a blood vessel located in that region than a blood vessel located in a yellow highlighted region. In addition, a yellow highlighted region can have a higher probability of an abnormality being present with respect to a blood vessel located in that region than a blood vessel located in a green highlighted region. Further, a green highlighted region can have a higher probability of an abnormality being present with respect to a blood vessel located in that region than a blood vessel located in a blue highlighted region. Regions included in the user interface where no highlighting is present can indicate regions that have less than a threshold probability of a blood vessel being associated with an abnormality.

Figure 6:
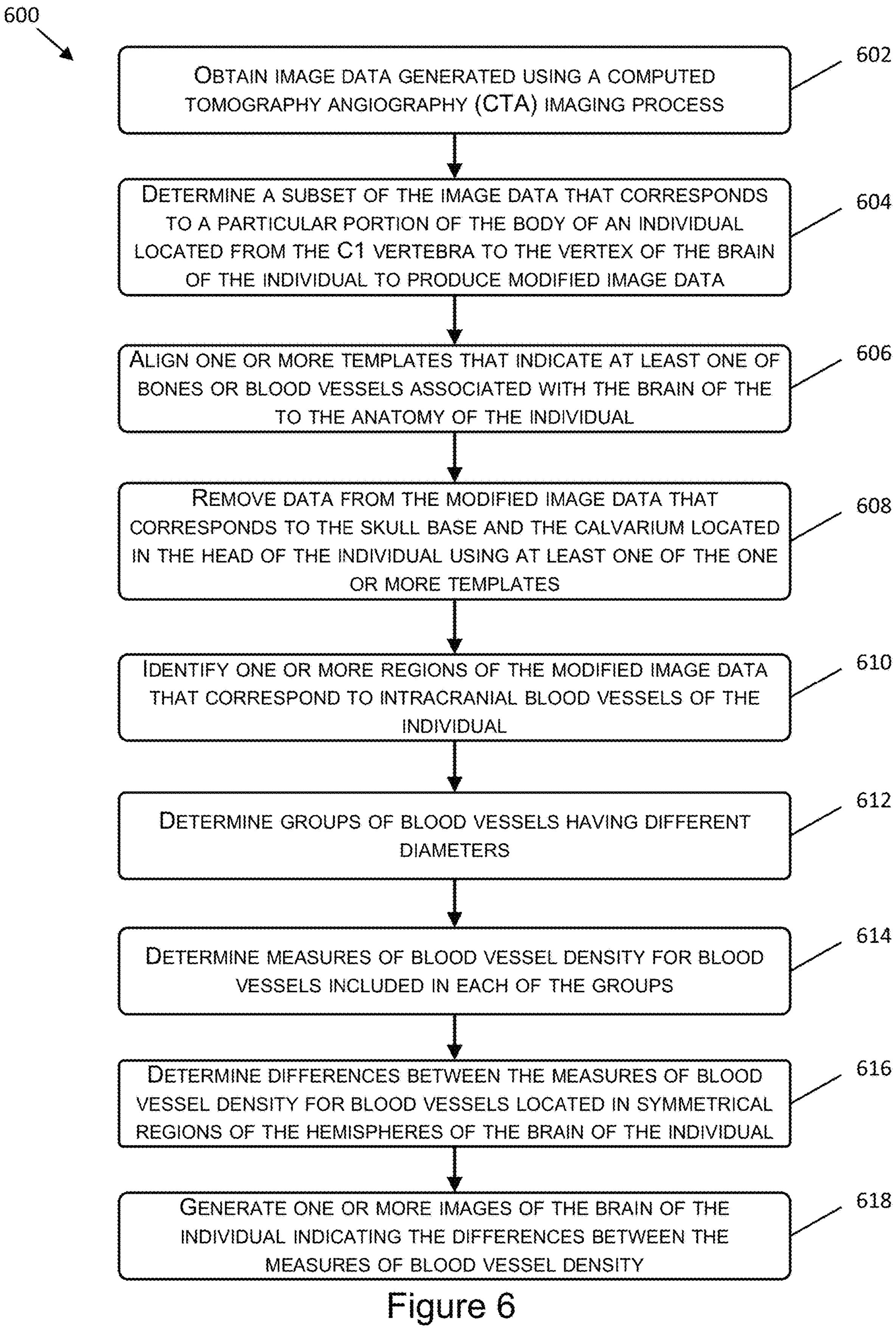
FIG. 6 is a flow diagram of an example process to generate one or more images of the brain of an individual that indicate possible blood vessel blockages, in accordance with one or more example implementations.

FIG. 6 is a flow diagram of an example process 600 to generate one or more images of the brain of an individual that indicate possible blood vessel blockages, in accordance with one or more example implementations. At operation 602, the process 600 can include obtaining image data generated using a computer tomography angiography (CTA) imaging process. The image data can correspond to features of an individual. To illustrate, the image data can correspond to features related to a head of an individual, a neck of an individual, a shoulder of an individual, a chest of the individual, an abdomen of an individual, combinations thereof, and the like. In implementations, the image data can be obtained directly from a CTA imaging device via one or more networks, such as a wired network or a wireless network. In various implementations, the image data can be obtained from a CTA imaging device via a local wireless network. The image data can also be accessible via a cloud computing storage system. For example, the image data can be sent by a CTA imaging device to a cloud computing storage system and a computing device can access the image data stored by the cloud computing storage system. In various implementations, the image data can be accessible after security credentials or other authentication information is provided.

The process 600 can include, at operation 604, determining a subset of the image data that corresponds to a portion of a body of an individual located from the C1 vertebra to the vertex of the brain of the individual. In example implementations, the additional portions of the image data that do not correspond to the portion of the body can be removed from the image data. In this way, modified image data can be produced. The removal of the additional portions of the image data can include at least one of deleting the additional portions or creating a data file that includes the modified image data without the additional portions of the image data.

At operation 606, the process 600 can include aligning one or more templates that indicate at least one of bones or blood vessels associated with the brain to the anatomy of the individual. The one or more templates can be produced by aggregating images from a number of individuals and determining locations of bones and/or blood vessels associated with the brains of the number of individuals. The one or more templates can be used to identify features related to the brain of the individual by performing a registration process of features of the individual included in the image data with features included in the one or more templates. The registration process can include analyzing the image data and/or the modified image data to determine features included in the image data and/or the modified image data that have characteristics that correspond to characteristics of features included in the one or more templates. In illustrative examples, the characteristics used to identify features of the image data and/or the modified image data that correspond to features included in the one or more templates can include at least one of locations of voxels of the features included in the image data and/or modified image data in relation to locations of voxels of the one or more templates or intensity information of the voxels included in the image data and/or modified image data with respect to intensity information of voxels of the one or more templates. The registration process can also include aligning features included in the image data and/or the modified image data with corresponding features included in the one or more templates.

In addition, at operation 608, the process 600 can include removing data from the modified image data that corresponds to the skull base and the calvarium located in the head of the individual using at least one of the one or more templates. In this way, features located in the head of the individual that correspond to bone can be removed from the modified image data using a template that indicates bone features. In addition, the process 600 can include, at operation 610, identifying one or more regions of the modified image data that correspond to intracranial blood vessels of the individual. In various implementations, the intracranial blood vessels can be identified after the data corresponding to bone features included in the head of the individual are removed. In example implementations, the data corresponding to the intracranial blood vessels can be identified using a template of the one or more templates that indicates locations of intracranial blood vessels. Further, the data corresponding to the intracranial blood vessels can be identified based on characteristics of the data, such as intensity values of voxels included in the modified image data.

Further, the process 600 can include, at operation 612, determining groups of blood vessels having different diameters. For example, a first group of blood vessels can be determined that has diameter values in a first range of values and a second group of blood vessels can be determined that has diameter values in a second range of values that is at least partially different from the first range of values. In some situations, the first range of values and the second range of values can overlap, while in other scenarios, the first range of values and the second range of values are not overlapping. In illustrative examples, the first group of blood vessels can include blood vessels having diameters of at least about 0.1 mm, at least about 0.5 mm, at least about 0.8 mm, at least about 1 mm, at least about 1.3 mm, at least about 1.5 mm, at least about 1.8 mm, or at least about 2 mm. Additionally, the first group of blood vessels can include blood vessels having diameters of no greater than about 4 mm, no greater than about 3.8 mm, no greater than about 3.5 mm, no greater than about 3.2 mm, no greater than about 3 mm, no greater than about 2.8 mm, no greater than about 2.5 mm, or no greater than about 2.2 mm. In various examples, the first range of values can be bounded by any of the illustrative examples described in this paragraph, such as from at least about 0.1 mm to no greater than about 4 mm, from at least about 0.1 mm to no greater than about 3 mm, from at least about 0.5 mm to no greater than about 3 mm, and so forth.

The second group of blood vessels can include blood vessels having diameters of at least about 3 mm, at least about 3.2 mm, at least about 3.5 mm, at least about 3.8 mm, at least about 4 mm, at least about 4.2 mm, at least about 4.5 mm, at least about 4.5 mm, at least about 4.8 mm, or at least about 5 mm. In addition, the second group of blood vessels can include blood vessels having diameters no greater than about 12 mm, no greater than about 11.5 mm, no greater than about 11 mm, no greater than about 10.5 mm, no greater than about 10 mm, no greater than about 9.8 mm, no greater than about 9.5 mm, no greater than about 9.2 mm, no greater than about 9 mm, no greater than about 8.8 mm, no greater than about 8.5 mm, no greater than about 8.2 mm, or no greater than about 8 mm. In various examples, the second range of values can be bounded by any of the illustrative examples described in this paragraph, such as from at least about 3 mm to no greater than about 12 mm, from at least about 3 mm to no greater than about 11 mm, from at least about 3 mm to no greater than about 10 mm, from at least about 3.2 mm to no greater than about 10 mm, and so forth.

In various examples, determining groups of blood vessels having different diameters can include identifying groups of blood vessels having a threshold amount of difference between the diameters of the respective blood vessels of each group. In one or more examples, operation 612 can include determining one or more blood vessels having one or more respective diameters that are at least 1.25 times larger than one or more additional diameters of one or more additional blood vessels. Additionally, operation 612 can include determining one or more blood vessels having one or more respective diameters that are at least 1.5 times larger than one or more additional diameters of one or more additional blood vessels. Further, operation 612 can include determining one or more blood vessels having one or more respective diameters that are at least 1.75 times larger than one or more additional diameters of one or more additional blood vessels. In still other examples, operation 612 can include determining one or more blood vessels having one or more respective diameters that are at least 2 times larger than one or more additional diameters of one or more additional blood vessels. In still additional examples, operation 612 can include determining one or more blood vessels having one or more respective diameters that are at least 2.5 times larger than one or more additional diameters of one or more additional blood vessels. In one or more other examples, operation 612 can include determining one or more blood vessels having one or more respective diameters that are at least 3 times larger than one or more additional diameters of one or more additional blood vessels.

At operation 614, the process 600 can include determining measures and/or metrics of blood vessel density of blood vessels included in each of the groups. In example implementations, the measures of blood vessel density can correspond to intensity values included in the modified image data that are associated with the blood vessels. For example, a measure of blood vessel density for the intracranial segment of the internal carotid artery can correspond to the intensity values of the voxels included in the modified image data that are related to the intracranial segment of the internal carotid artery. In another example, a measure of the blood vessel density for the M1 segment of the middle cerebral artery can correspond to the intensity values of the voxels included in the modified image data that are related to the M1 segment of the middle cerebral artery. In an additional example, a measure of the blood vessel density for the M2 segment of the middle cerebral artery can correspond to the intensity values of the voxels included in the modified image data that are related to the M2 segment of the middle cerebral artery. In various implementations, a measure of density for a blood vessel located in the head of the individual can correspond to a sum of the intensity values of voxels associated with the blood vessel included in the modified image data.

The process 600 can also, at operation 616, include determining differences between the measures of blood vessel density for blood vessels located in symmetrically arranged regions of the hemispheres of the brain of the individual. In implementations, the brain of the individual can be divided into one or more regions in each hemisphere of the brain of the individual. In illustrative examples, the brain of the individual can be divided in three regions in each hemisphere of the brain of the individual. In these scenarios, the six total regions can be grouped into three sets of pairs with each pair being disposed substantially symmetrical with respect to each other. In additional illustrative examples, a pair of regions can include a first region that includes an intracranial segment of the internal carotid artery and a proximal portion of the M1 segment of the middle cerebral artery located in a first hemisphere of the brain of the individual and a second region that includes an intracranial segment of the internal carotid artery and a proximal portion of the M1 segment of the middle cerebral artery located in a second hemisphere of the brain of the individual. Additionally, a second pair of regions can include a third region that includes middle to distal portions of the M1 segment of the middle cerebral artery located in the first hemisphere of the brain of the individual and a fourth region that includes middle to distal portions of the M1 segment of the middle cerebral artery located in the second hemisphere of the brain of the individual. Further, a third pair of regions can include a fifth region that includes at least an M2 segment of the middle cerebral artery located in the first hemisphere of the brain of the individual and a sixth region that includes at least an M2 segment of the middle cerebral artery located in the second hemisphere of the brain of the individual.

In various implementations, at least one difference can be determined between one or more blood vessels located in the first region of the first hemisphere of the brain of the individual and one or more blood vessels located in the second region of the second hemisphere of the brain of the individual. Additionally, at least one difference can be determined between one or more blood vessels located in the third region of the first hemisphere of the brain of the individual and one or more blood vessels located in the fourth region of the second hemisphere of the brain of the individual. Further, at least one difference can be determined between one or more blood vessels located in the fifth region of the first hemisphere of the brain of the individual and one or more blood vessels located in the sixth region of the second hemisphere of the brain of the individual. In example implementations, ratios can be determined corresponding to the differences between the densities of blood vessels located in the different hemispheres of the brain.

Differences between densities of blood vessels located in different hemispheres of the brain can indicate a probability and/or a severity of an abnormality related to the blood vessels located in the brain. In various implementations, the abnormality can be related to occlusion of one or more blood vessels located in the brain of an individual. In example implementations, the abnormality can be related to an individual suffering from a stroke. In implementations, an amount of reduction in density between blood vessels located in different hemispheres of the brain can be indicative of an abnormality with respect to the blood vessels that have the reduced density. For example, an amount of reduction between a density of a blood vessel located in one region of a first hemisphere of the brain of the individual with respect to a density of a counterpart region of a second hemisphere of the brain of the individual can indicate an abnormality with respect to the blood vessel. A number of ranges of reduction in blood vessel density can be utilized to determine a probability and/or a severity of an abnormality with respect to blood vessels located in the brain of the individual. To illustrate, a first range of values corresponding to amounts of reduction in density between blood vessels located in different hemispheres of the brain of the individual can indicate a first number of probabilities and/or severities of an abnormality with respect to the blood vessels, while a second range of values corresponding to amounts of reduction in density between blood vessels located in different hemispheres of the brain of the individual can indicate a second number of probabilities and/or severities of an abnormality with respect to the blood vessels.

In addition to determining differences between measures of blood vessel density, ratios of metrics and/or measures of blood vessel density can be determined. For example, a ratio between one or more measure and/or metrics of blood vessel density for one or more first blood vessels located in a region of a first hemisphere of the brain and one or more measures and/or metrics of blood vessel density for one or more second blood vessels located in a counterpart region of a second hemisphere of the brain may be determined. In various examples, the ratios can be used to determine a probability of an abnormality with respect one or more blood vessels located in at least one region of the brain of the individual.

At operation 618, the process 600 can include generating one or more images of the brain of the individual indicating the differences between the measures of the blood vessel density. The images can indicate blood vessels included in the brain of the individual and can also indicate regions of the brain of the individual and/or blood vessels that can be associated with at least a threshold probability and/or a threshold severity of an abnormality. In various implementations, the probabilities and/or seventies related to abnormalities of blood vessels located in the brain of an individual can be displayed using different colors in the one or more images. For example, a first range of probabilities of an abnormality and/or levels of severity of an abnormality with respect to blood vessels included in a brain of an individual can be shown as a first color in the one or more images and a second range of probabilities of an abnormality and/or levels of severity of an abnormality with respect to blood vessels included in a brain of an individual can be shown as a second color in the one or more images. In example implementations, the one or more images can be displayed on a display device that is accessible to a clinician. Further, the one or more images can highlight locations within the brain of the individual where an occlusion may be located by displaying an arrow, circle, box, or other arbitrarily shaped outline.

Figure 7:
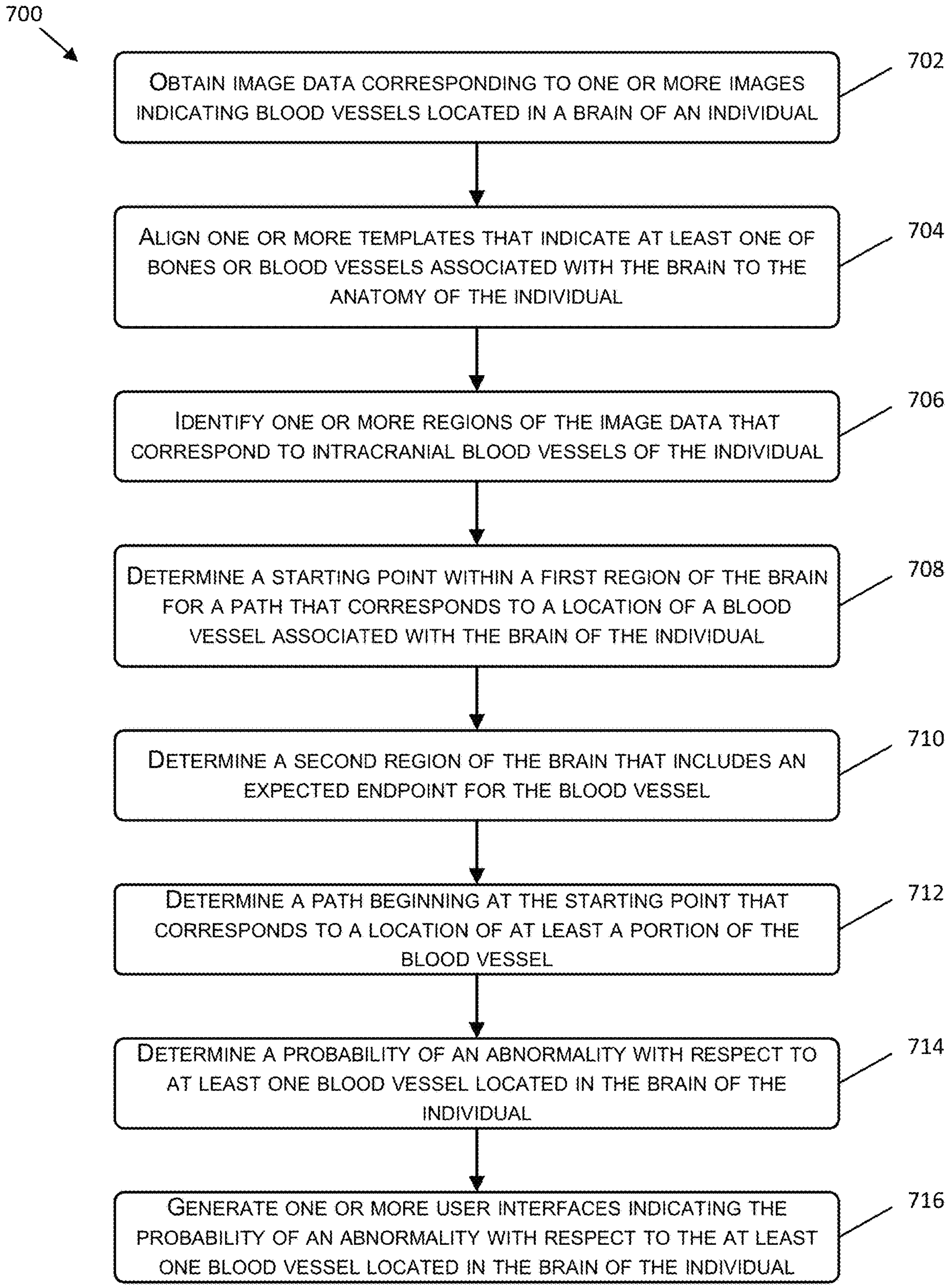
FIG. 7 is a flow diagram of an example process 700 to determine possible blood vessel blockages by tracking a path of one or more blood vessels in the brain, in accordance with one or more example implementations.

FIG. 7 is a flow diagram of an example process 700 to determine possible blood vessel blockages by tracking a path of one or more blood vessels in the brain, in accordance with one or more example implementations. At operation 702, the process 700 can include obtaining image data corresponding to one or more images indicating blood vessels located in a brain of an individual. The one or more images can be generated using a computer tomography angiography (CTA) imaging process. The image data can correspond to features of an individual. To illustrate, the image data can correspond to features related to a head of an individual, a neck of an individual, combinations thereof, and the like. In various implementations, the image data can be modified by removing portions of the data corresponding to portions of the body of the individual that do not include the brain, such as bones of the skull, neck, and/or face.

The process 700 can include, at operation 704, aligning one or more templates that indicate at least one of bones or blood vessels associated with the brain of the individual. The one or more templates can be produced by aggregating images from a number of individuals and determining locations of bones and/or blood vessels associated with the brains of the number of individuals. The one or more templates can be used to identify features related to the brain of the individual by performing a registration process of features of the individual included in the image data with features included in the one or more templates. The registration process can include analyzing the image data and/or the modified image data to determine features included in the image data and/or the modified image data that have characteristics that correspond to characteristics of features included in the one or more templates. In illustrative examples, the characteristics used to identify features of the image data and/or the modified image data that correspond to features included in the one or more templates can include at least one of locations of voxels of the features included in the image data and/or modified image data in relation to locations of voxels of the one or more templates or intensity information of the voxels included in the image data and/or modified image data with respect to intensity information of voxels of the one or more templates. The registration process can also include aligning features included in the image data and/or the modified image data with corresponding features included in the one or more templates.

In addition, at operation 706, the process 700 can include identifying one or more portions of the modified image data that correspond to intracranial blood vessels of the individual. In various implementations, the intracranial blood vessels can be identified after the data corresponding to bone features included in the head of the individual are removed. In example implementations, the data corresponding to the intracranial blood vessels can be identified using a template of the one or more templates that indicates locations of intracranial blood vessels. Further, the data corresponding to the intracranial blood vessels can be identified based on characteristics of the data, such as intensity values of voxels included in the modified image data.

Further, the process 700 can include, at operation 708, determining a starting point within a first region of the brain to begin determining one or more potential paths of a blood vessel associated with the brain. At least a portion of the one or more potential paths can correspond to a location of the blood vessel within the brain of the individual. The starting location can be determined by identifying a region of the brain that is proximal with respect to the midline of the brain. In one or more implementations, the region of the brain can be identified based on a template that indicates the region and that is aligned with the anatomy of the individual based on image data of the brain of the individual. In one or more examples, the region can include a proximal portion of the middle cerebral artery. The starting point can also be identified by determining vesselness values for individual voxels of the image data included in the region. The respective vesselness values can indicate a probability that a given voxel corresponds to a location of a blood vessel of the brain of the individual. A vesselness value can correspond to an amount of contrast between a voxel and a background. In one or more illustrative examples, the vesselness values for voxels can be determined by calculating eigenvalues of a Hessian filter matrix. The eigenvalues of the Hessian filter matrix can correspond to the change in contrast along the principal eigenvector dimensions computed in the Hessian filter. In various examples, the output of the Hessian filter can correspond to brightness of a voxel and a size of the voxel, where the brightness can correspond to a relative HU different against surroundings.

Also, at operation 710, the process 700 can include determining a second region of the brain that includes an expected endpoint of the blood vessel. The second region can be determined based on a template that indicates one or more possible locations of the endpoint of the blood vessel. In situations where the blood vessel is the middle cerebral artery, the second region can include distal portions of the middle cerebral artery. In one or more examples, the second region can include one or more locations that a distal portion of the blood vessel passes to reach distal parts of the brain.

The process 700 can include, at operation 712, determining a path beginning at the starting point. The path can correspond to a location of at least a portion of the blood vessel. The path can include a least costly path of an evaluated graph that includes nodes corresponding to voxels of the one or more images. In one or more illustrative examples, the least costly path can be determined using concepts derived from Prim, R. C. (November 1957), "Shortest connection networks and some generalizations", Bell System Technical Journal, 36 (6): 1389-1401 and Dijkstra, E. W. (1959). A note on two problems in connexion with graphs". Numerische Mathematik. 1: 269-271. In various examples, the cost of moving between nodes of the path can be determined according to:

$$\text{cost}=100/(\text{vesselness}-\text{vesselness}_{mn\_threshold}+1).$$

Thus, in situations where the vesselness value of a voxel is less than a defined threshold, the cost can be infinite. The $\text{vesselness}_{mn\_threshold}$ value can be determined by performing an analysis of a number of datasets including images, such as CTA images. In various examples, the analysis can determine a threshold vesselness value that corresponds to noise of the images and objects included in the images. In some examples, the $\text{vesselness}_{mn\_threshold}$ can be a value between 6.0 HU and 12.0 HU. In CTA images, blood vessels can have opacification values from about 25 HU to about 400 HU and noise can be suppressed by the Hessian filter to values close to zero. In one or more examples, the path can be traversed from one voxel to another voxel having a lowest cost in relation to neighboring voxels.

In one or more implementations, the path can be terminated for a number of reasons. For example, the path can be terminated in response to the path reaching a voxel that has been labeled as being included in the second region that includes the endpoint. In additional examples, the path can be terminated in response to the determining that each voxel that has a finite cost to pass through have already been visited. In these situations, the path is terminated before the second region is reached. Further, the path can be terminated in response to a path of the cost being above a specified maximum cost.

At operation 714, the process 700 can include determining a probability of an abnormality with respect to at least one blood vessel located in the brain of the individual. In various examples, the probability of an abnormality existing in the brain of the individual may depend on the path reaching the second region. In situations where the path reaches the second region, the probability of an abnormality being present with respect to at least one blood vessel located in the brain of the individual can be zero or relatively low. Additionally, in situations where the path does not reach the second region, the probability of an abnormality being present with respect to at least one blood vessel located in the brain of the individual may be relatively high.

Additionally, the process 700 can include, at operation 716 generating one or more user interfaces indicating the probability of an abnormality with respect to the at least one blood vessel located in the brain of the individual. In various examples, the one or more user interface may include one or more colors indicating a probability of an abnormality being present, such as red for relatively high probabilities, yellow for moderate probabilities, and green for relatively low probabilities.

Figure 8:
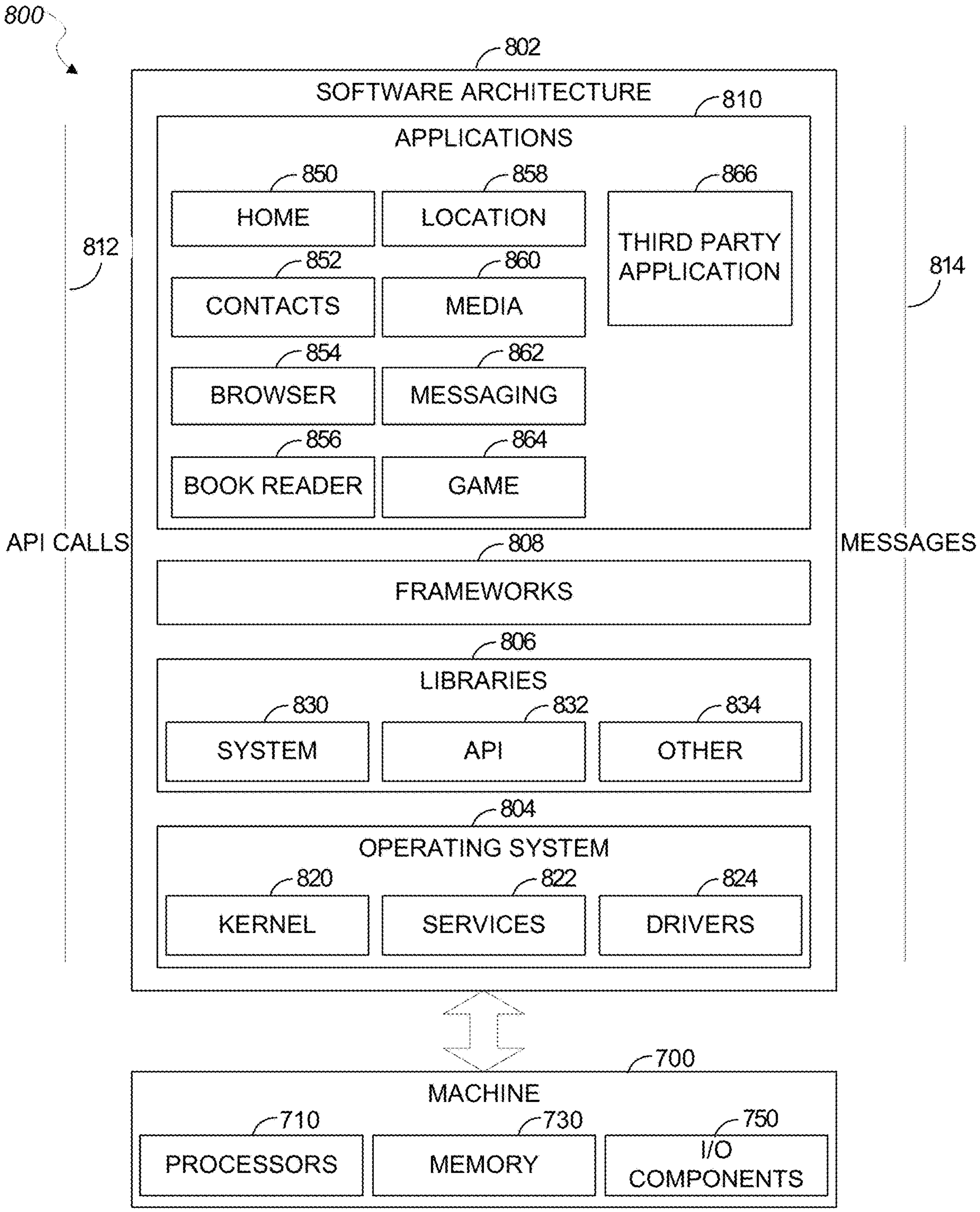
FIG. 8 is a block diagram illustrating an example architecture of software, which can be installed on any one or more of the devices described herein, in accordance with one or more example implementations.

FIG. 8 is a block diagram 800 illustrating an architecture of software 802, which can be installed on any one or more of the devices described above. In implementations, at least a portion of the operations described with respect to the frameworks 100, 300, and 400 and the processes 200, 500, and 600 can be executed using the software 802. FIG. 8 is merely a non-limiting example of a software architecture, and it will be appreciated that many other architectures can be implemented to facilitate the functionality described herein. In various scenarios, the software 802 is implemented by hardware such as a machine 900 of FIG. 9 that includes processors 910, memory 930, and input/output (I/O) components 950. In this example architecture, the software 802 can be conceptualized as a stack of layers where each layer may provide a specified functionality. For example, the software 802 includes layers such as an operating system 804, libraries 806, frameworks 808, and applications 810. Operationally, the applications 810 invoke application programming interface (API) calls 812 through the software stack and receive messages 814 in response to the API calls 812, consistent with some implementations.

In various implementations, the operating system 804 manages hardware resources and provides common services. The operating system 804 includes, for example, a kernel 820, services 822, and drivers 824. The kernel 820 acts as an abstraction layer between the hardware and the other software layers, consistent with some embodiments. For example, the kernel 820 provides memory management, processor management (e.g., scheduling), component management, networking, and security settings, among other functionality. The services 822 can provide other common services for the other software layers. The drivers 824 are responsible for controlling or interfacing with the underlying hardware, according to some embodiments. For instance, the drivers 824 can include display drivers, camera drivers, BLUETOOTH® or BLUETOOTH® Low-Energy drivers, flash memory drivers, serial communication drivers (e.g., Universal Serial Bus (USB) drivers), Wi-Fi® drivers, audio drivers, power management drivers, and so forth.

In some embodiments, the libraries 806 provide a low-level common infrastructure utilized by the applications 810. The libraries 806 can include system libraries 830 (e.g., C standard library) that can provide functions such as memory allocation functions, string manipulation functions, mathematic functions, and the like. In addition, the libraries 806 can include API libraries 832 such as media libraries (e.g., libraries to support presentation and manipulation of various media formats such as Moving Picture Experts Group-4 (MPEG4). Advanced Video Coding (H.264 or AVC), Moving Picture Experts Group Layer-3 (MP3), Advanced Audio Coding (AAC), Adaptive Multi-Rate (AMR) audio codec, Joint Photographic Experts Group (JPEG or JPG), or Portable Network Graphics (PNG)), graphics libraries (e.g., an OpenGL framework used to render in 2D and 3D in a graphic context on a display), database libraries (e.g., SQLite to provide various relational database functions), web libraries (e.g., WebKit to provide web browsing functionality), and the like. The libraries 806 can also include a wide variety of other libraries 834 to provide many other APIs to the applications 810.

The frameworks 808 provide a high-level common infrastructure that can be utilized by the applications 810, according to some implementations. For example, the frameworks 808 provide various graphical user interface (GUI) functions, high-level resource management, high-level location services, and so forth. The frameworks 808 can provide a broad spectrum of other APIs that can be utilized by the applications 810, some of which may be specific to an operating system 804 or platform.

In example implementations, the applications 810 include a home application 850, a contacts application 852, a browser application 854, a book reader application 856, a location application 858, a media application 860, a messaging application 862, a game application 864, and a broad assortment of other applications, such as a third-party application 866. According to some embodiments, the applications 810 are programs that execute functions defined in the programs. Various programming languages can be employed to create one or more of the applications 810, structured in a variety of manners, such as object-oriented programming languages (e.g., Objective-C, Java, or C++) or procedural programming languages (e.g., C or assembly language). In a specific example, the third-party application 866 (e.g., an application developed using the ANDROID™ or IOS™ software development kit (SDK) by an entity other than the vendor of the platform) may be mobile software running on a mobile operating system such as IOS™, ANDROID™, WINDOWS® Phone, or another mobile operating system. In this example, the third-party application 866 can invoke the API calls 812 provided by the operating system 804 to facilitate functionality described herein.

Figure 9:
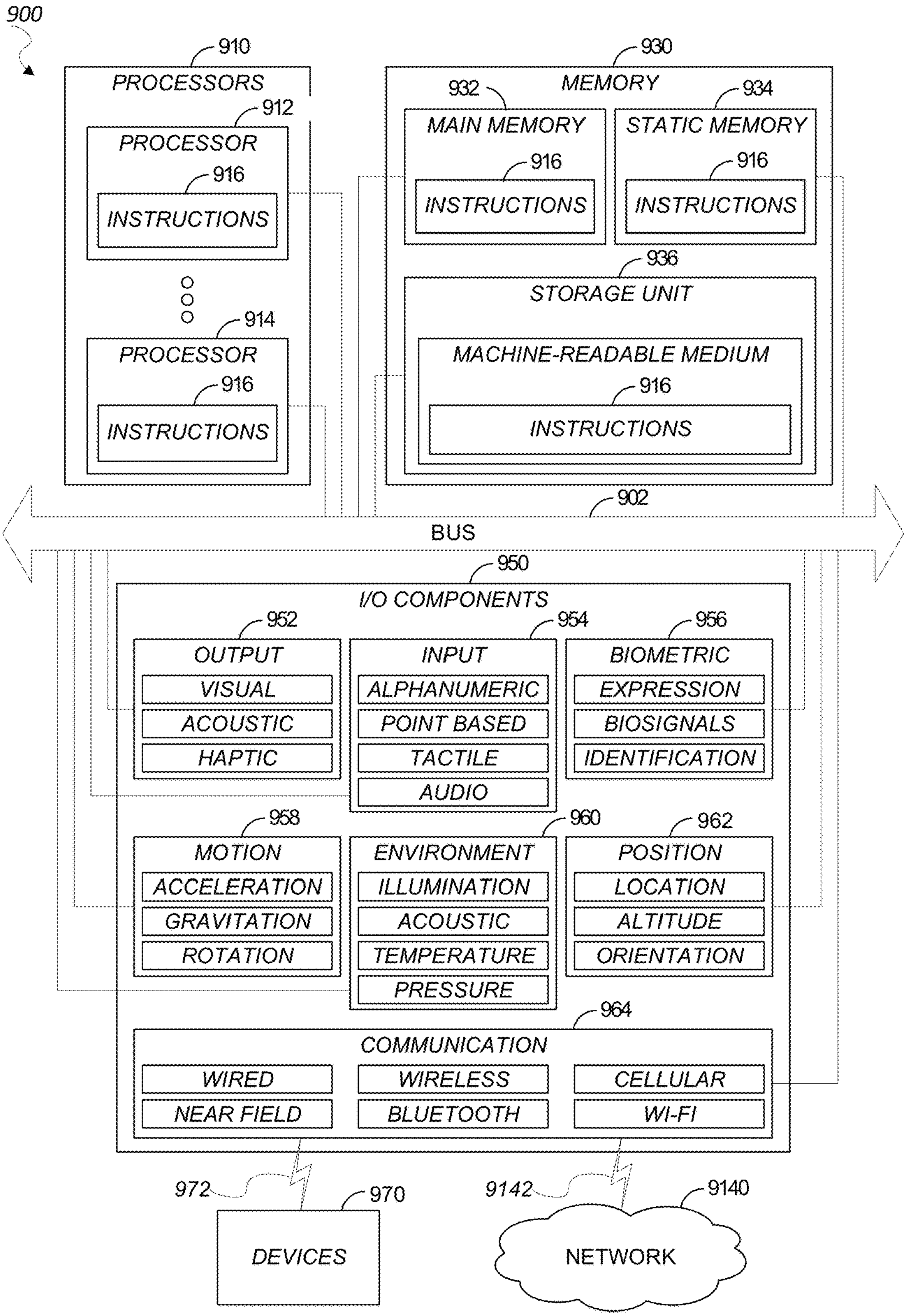
FIG. 9 illustrates a diagrammatic representation of an example machine in the form of a computer system within which a set of instructions may be executed for causing the machine to perform any one or more of the methodologies discussed herein, in accordance with one or more example implementations.

FIG. 9 illustrates a diagrammatic representation of an example machine 900 in the form of a computer system within which a set of instructions may be executed for causing the machine 900 to perform any one or more of the methodologies discussed herein, in accordance with one or more example implementations. Specifically. FIG. 9 shows a diagrammatic representation of the machine 900 in the example form of a computer system, within which instructions 916 (e.g., software, a program, an application, an applet, an app, or other executable code) for causing the machine 900 to perform any one or more of the methodologies discussed herein may be executed. For example, the instructions 916 may cause the machine 900 to execute the process 200 of FIG. 2, the process 500 of FIG. 5, and/or the process 600 of FIG. 6. The machine 900 can also execute operations described with respect to the framework 100 of FIG. 1, the framework 300 of FIG. 3, and the framework 400 of FIG. 4. In various implementations, at least a portion of the operations performed by the brain image analysis system 102 can be performed by the machine 900. The instructions 916 transform the general, non-programmed machine 900 into a specific machine 900 programmed to carry out the described and illustrated functions in the manner described. In alternative embodiments, the machine 900 operates as a standalone device or may be coupled (e.g., networked) to other machines. In a networked deployment, the machine 900 may operate in the capacity of a server machine or a client machine in a server-client network environment, or as a peer machine in a peer-to-peer (or distributed) network environment. The machine 900 may comprise, but not be limited to, a server computer, a client computer, a personal computer (PC), a tablet computer, a laptop computer, a netbook, a set-top box (STB), a personal digital assistant (PDA), an entertainment media system, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 916, sequentially or otherwise, that specify actions to be taken by the machine 900. Further, while only a single machine 900 is illustrated, the term "machine" shall also be taken to include a collection of machines 900 that individually or jointly execute the instructions 916 to perform any one or more of the methodologies discussed herein.

The machine 900 may include processors 910, memory 930, and I/O components 950, which may be configured to communicate with each other such as via a bus 902. In an example implementation, the processors 910 (e.g., a central processing unit (CPU), a reduced instruction set computing (RISC) processor, a complex instruction set computing (CISC) processor, a graphics processing unit (GPU), a digital signal processor (DSP), an application-specific integrated circuit (ASIC), a radio-frequency integrated circuit (RFIC), another processor, or any suitable combination thereof) may include, for example, a processor 912 and a processor 914 that may execute the instructions 916. The term "processor" is intended to include multi-core processors that may comprise two or more independent processors (sometimes referred to as "cores") that may execute instructions 916 contemporaneously. Although FIG. 8 shows multiple processors 910, the machine 900 may include a single processor 912 with a single core, a single processor 912 with multiple cores (e.g., a multi-core processor 912), multiple processors 912, 914 with a single core, multiple processors 912, 914 with multiple cores, or any combination thereof.

The memory 930 may include a main memory 932, a static memory 934, and a storage unit 936, each accessible to the processors 910 such as via the bus 902. The main memory 932, the static memory 934, and the storage unit 936 store the instructions 916 embodying any one or more of the methodologies or functions described herein. The instructions 916 may also reside, completely or partially, within the main memory 932, within the static memory 934, within the storage unit 936, within at least one of the processors 910 (e.g., within the processor's cache memory), or any suitable combination thereof, during execution thereof by the machine 900.

The I/O components 950 may include a wide variety of components to receive input, provide output, produce output, transmit information, exchange information, capture measurements, and so on. The specific V/O components 950 that are included in a specified machine 900 will depend on the type of machine. For example, portable machines such as mobile phones will likely include a touch input device or other such input mechanisms, while a headless server machine will likely not include such a touch input device. It will be appreciated that the I/O components 950 may include many other components that are not shown in FIG. 8. The I/O components 950 are grouped according to functionality merely for simplifying the following discussion, and the grouping is in no way limiting. In various example embodiments, the I/O components 950 may include output components 952 and input components 954. The output components 952 may include visual components (e.g., a display such as a plasma display panel (PDP), a light-emitting diode (LED) display, an organic light-emitting diode (OLED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 954 may include alphanumeric input components (e.g., a keyboard, a touch screen configured to receive alphanumeric input, a photo-optical keyboard, or other alphanumeric input components), point-based input components (e.g., a mouse, a touchpad, a trackball, a joystick, a motion sensor, or another pointing instrument), tactile input components (e.g., a physical button, a touch screen that provides location and/or force of touches or touch gestures, or other tactile input components), audio input components (e.g., a microphone), and the like.

In further example embodiments, the I/O components 950 may include biometric components 956, motion components 958, environmental components 960, or position components 962, among a wide array of other components. For example, the biometric components 956 may include components to detect expressions (e.g., hand expressions, facial expressions, vocal expressions, body gestures, or eye tracking), measure biosignals (e.g., blood pressure, heart rate, body temperature, perspiration, or brain waves), identify a person (e.g., voice identification, retinal identification, facial identification, fingerprint identification, or electroencephalogram-based identification), and the like. The motion components 958 may include acceleration sensor components (e.g., accelerometer), gravitation sensor components, rotation sensor components (e.g., gyroscope), and so forth. The environmental components 960 may include, for example, illumination sensor components (e.g., photometer), temperature sensor components (e.g., one or more thermometers that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detect concentrations of hazardous gases for safety or to measure pollutants in the atmosphere), or other components that may provide indications, measurements, or signals corresponding to a surrounding physical environment. The position components 962 may include location sensor components (e.g., a Global Positioning System (GPS) receiver component), altitude sensor components (e.g., altimeters or barometers that detect air pressure from which altitude may be derived), orientation sensor components (e.g., magnetometers), and the like.

Communication may be implemented using a wide variety of technologies. The I/O components 950 may include communication components 964 operable to couple the machine 900 to a network 9140 or devices 970 via a coupling 9142 and a coupling 972, respectively. For example, the communication components 964 may include a network interface component or another suitable device to interface with the network 9140. In further examples, the communication components 964 may include wired communication components, wireless communication components, cellular communication components, near field communication (NFC) components, Bluetooth® components (e.g., Bluetooth® Low Energy), Wi-Fi® components, and other communication components to provide communication via other modalities. The devices 970 may be another machine or any of a wide variety of peripheral devices (e.g., coupled via a USB).

Moreover, the communication components 964 may detect identifiers or include components operable to detect identifiers. For example, the communication components 964 may include radio-frequency identification (RFID) tag reader components, NFC smart tag detection components, optical reader components (e.g., an optical sensor to detect one-dimensional bar codes such as Universal Product Code (UPC) bar code, multi-dimensional bar codes such as QR code, Aztec code, Data Matrix, Dataglyph, MaxiCode, PDF417, Ultra Code. UCC RSS-2D bar code, and other optical codes), or acoustic detection components (e.g., microphones to identify tagged audio signals). In addition, a variety of information may be derived via the communication components 964, such as location via Internet Protocol (IP) geolocation, location via Wi-Fi® signal triangulation, location via detecting an NFC beacon signal that may indicate a given location, and so forth.

The various memories (i.e., 930, 932, 934, and/or memory of the processor(s) 910) and/or the storage unit 936 may store one or more sets of instructions 916 and data structures (e.g., software) embodying or utilized by any one or more of the methodologies or functions described herein. These instructions (e.g., the instructions 916), when executed by the processor(s) 910, cause various operations to implement the disclosed embodiments.

As used herein, the terms "machine-storage medium," "device-storage medium," and "computer-storage medium" mean the same thing and may be used interchangeably. The terms refer to a single or multiple storage devices and/or media (e.g., a centralized or distributed database, and/or associated caches and servers) that store executable instructions 916 and/or data. The terms shall accordingly be taken to include, but not be limited to, solid-state memories, and optical and magnetic media, including memory internal or external to processors 910. Specific examples of machine-storage media, computer-storage media, and/or device-storage media include non-volatile memory, including by way of example semiconductor memory devices, e.g., erasable programmable read-only memory (EPROM), electrically erasable programmable read-only memory (EEPROM), field-programmable gate array (FPGA), and flash memory devices; magnetic disks such as internal hard disks and removable disks; magneto-optical disks; and CD-ROM and DVD-ROM disks. The terms "machine-storage media." "computer-storage media," and "device-storage media" specifically exclude carrier waves, modulated data signals, and other such media, at least some of which are covered under the term "signal medium" discussed below.

In various example embodiments, one or more portions of the network 9140 may be an ad hoc network, an intranet, an extranet, a virtual private network (VPN), a local-area network (LAN), a wireless LAN (WLAN), a wide-area network (WAN), a wireless WAN (WWAN), a metropolitan-area network (MAN), the Internet, a portion of the Internet, a portion of the public switched telephone network (PSTN), a plain old telephone service (POTS) network, a cellular telephone network, a wireless network, a Wi-Fi® network, another type of network, or a combination of two or more such networks. For example, the network 9140 or a portion of the network 9140 may include a wireless or cellular network, and the coupling 9142 may be a Code Division Multiple Access (CDMA) connection, a Global System for Mobile communications (GSM) connection, or another type of cellular or wireless coupling. In this example, the coupling 9142 may implement any of a variety of types of data transfer technology, such as Single Carrier Radio Transmission Technology (1×RTT), Evolution-Data Optimized (EVDO) technology, General Packet Radio Service (GPRS) technology, Enhanced Data rates for GSM Evolution (EDGE) technology, third Generation Partnership Project (3GPP) including 3G, fourth generation wireless (4G) networks, Universal Mobile Telecommunications System (UMTS). High-Speed Packet Access (HSPA), Worldwide Interoperability for Microwave Access (WiMAX), Long-Term Evolution (LTE) standard, others defined by various standard-setting organizations, other long-range protocols, or other data transfer technology.

The instructions 916 may be transmitted or received over the network 9140 using a transmission medium via a network interface device (e.g., a network interface component included in the communication components 964) and utilizing any one of a number of well-known transfer protocols (e.g., Hypertext Transfer Protocol (HTTP)). Similarly, the instructions 916 may be transmitted or received using a transmission medium via the coupling 972 (e.g., a peer-to-peer coupling) to the devices 970. The terms "transmission medium" and "signal medium" mean the same thing and may be used interchangeably in this disclosure. The terms "transmission medium" and "signal medium" shall be taken to include any intangible medium that is capable of storing, encoding, or carrying the instructions 916 for execution by the machine 900, and include digital or analog communications signals or other intangible media to facilitate communication of such software. Hence, the terms "transmission medium" and "signal medium" shall be taken to include any form of modulated data signal, carrier wave, and so forth. The term "modulated data signal" means a signal that has one or more of its characteristics set or changed in such a manner as to encode information in the signal.

The terms "machine-readable medium," "computer-readable medium," and "device-readable medium" mean the same thing and may be used interchangeably in this disclosure. The terms are defined to include both machine-storage media and transmission media. Thus, the terms include both storage devices/media and carrier waves/modulated data signals.

EXAMPLES

Example 1

Methods

Consecutive patients who underwent multimodal CT with thin-slice CTA between Jan. 1, 2017 and Dec. 31, 2018 for a suspected acute ischemic stroke within 24 hours of onset were retrospectively identified. These multimodal CTs were assessed by two neuroradiologists in consensus for the presence and site of an anterior circulation LVO or M2-segment middle cerebral artery (M2-MCA) occlusion (the reference standard). The patients' CTAs were then processed using the automated LVO-detection algorithm (RAPID CTA). Receiver-operating characteristic analysis was used to determine sensitivity, specificity and NPV of the algorithm for detection of a) an LVO and b) either an LVO or M2-MCA occlusion.

Results

CTAs from 477 patients were analyzed (271 men and 206 women: median age 71, interquartile range 60-80). Median processing time was 158 seconds (Inter-quartile range 150-167 seconds). 78 patients had anterior circulation LVOs and 28 had isolated M2-MCA occlusions. The sensitivity, negative predictive value (NPV) and specificity were 0.94, 0.98 and 0.76 respectively for detection of intracranial LVOs and 0.92, 0.97 and 0.81 respectively for detection of either an intracranial LVO or M2-MCA occlusion.

Materials and Methods

Consecutive patients who presented to our institution between Jan. 1, 2017 and 31 Dec. 2018, underwent multimodal brain CT for a suspected acute ischemic stroke, and met the following inclusion criteria were retrospectively identified using our Picture Archiving and Communication System and electronic medical records. The inclusion criteria were: a) patient older than 18 years, and b) multimodal "stroke protocol" CT performed within 24 hours of symptom onset or last seen well. Exclusion criteria were: a) technically inadequate CTA (poor contrast bolus or substantial motion or metal artifact that precluded accurate assessment of the intracranial arteries to the level of the distal M2 segments of the middle cerebral arteries by an experienced neuroradiologist) and b) thin slice CTA images unavailable. The justification for these exclusion criteria were: a) the CTA had to be of sufficient quality for accurate interpretation by an experienced human reader, since this was the criterion standard against which the LVO-detection algorithm was assessed; and b) thin slice images acquired using a 512×512 image matrix were necessary for processing by the algorithm.

CT Image Acquisition and Reconstruction Technique

All patients were scanned on a 256-slice multi-detector CT (iCT 256, Philips Healthcare, Cleveland, OH, USA). Our institution's routine multimodal "stroke CT protocol" consisted of unenhanced CT followed by CT perfusion (CTP) and CT angiography.

Unenhanced CT was acquired in the helical mode with the following parameters: 0.625 mm slice collimation, spiral pitch factor of 0.283, tube voltage of 120 kV and image matrix 512×512. Images were reconstructed using a UB kernel at 1 mm overlapping sections, with axial, coronal and sagittal multiplanar reconstructions performed at 4 mm slice thickness.

50 mL of non-ionic contrast agent (350 mg iodine/mL, iohexol Omnipaque 350, GE Healthcare, Wisconsin, USA) was injected intravenously for CTP.

For the subsequent CTA, 80 mL of the same non-ionic contrast agent was injected intravenously at a rate of 5 mL/s followed by a 40 mL saline flush at 6 mL/s. Contrast bolus triggering was performed in the aortic arch. Parameters for the helical acquisition were as follows: craniocaudal coverage from the aortic arch to vertex, 100 kV tube voltage with dose modulation, slice collimation width 0.625 mm, image matrix 512×512, and spiral pitch factor 0.618. The following reconstruction parameters were used: iterative reconstruction (iDose) factor of 5 and convolution kernel B. Axial images were reconstructed at 0.8 mm overlapping sections. Axial, coronal and sagittal multiplanar reconstructions were performed at 4 mm slice thickness. Axial maximum intensity projections were reconstructed at 10-mm thickness.

LVO Definitions

With respect to example 1, the term intracranial "LVO" was used specifically to describe anterior circulation occlusions, involving the M1-MCA and the intracranial ICA (from the petrous segment to the ICA bifurcation). "Supraclinoid ICA" refers to the ophthalmic and communicating segments of the ICA.

The M1-MCA was defined functionally as the segment from the ICA bifurcation to the MCA bifurcation or trifurcation. When there was early division of the MCA, proximal to its genu, the short proximal trunk was called the M1 segment and the branches distal to division were defined as M2 segments.

The M2 segments were defined as those immediately distal to the MCA bifurcation/trifurcation that ascend vertically within the Sylvian fissure (assessed on coronal images). Proximal M2 occlusions were defined as being located inferior to a transverse plane drawn through the mid-point of the Sylvian cistern on coronal images. The dominance of an M2 segment was assessed based on its size relative to the other M2 segment(s) and the extent of the perfusion abnormality it produced.

Image Analysis

Two diagnostic neuroradiologists (with 8 and 9 years of post-fellowship experience, respectively) reviewed each patient's complete multimodal CT: the unenhanced CT, CTP, and CTA.

Details of the patient's clinical presentation were provided. The findings were then verified by an interventional neuroradiologist with 7 years' experience. These neuroradiologist reads served as the criterion-standard against which the performance of the automated LVO detection tool was assessed.

For each patient, the technical adequacy of the CTA was assessed. The following features were then recorded in consensus.

1. The presence, side and site of an intracranial LVO or cervical ICA occlusion:
2. The presence, side, site (proximal versus distal) and dominance of a M2-MCA occlusion.

For tandem lesions, each site of occlusion was recorded. For M1-MCA occlusions, the specific sub-site of occlusion (proximal two-third versus distal third of the M1 segment) and the length of the non-opacified vessel segment were recorded.

LVO Detection Using Automated Software

An automated tool (RAPID CTA, RAPID 4.9, iSchemaView, Menlo Park, CA) was used to analyze each patient's CTA raw data for the presence and side of an LVO.

The RAPID CTA algorithm performs the following operations: (1) imports the CTA raw data in Digital Imaging and Communications in Medicine format: (2) motion and tilt corrects the images; (3) trims the CTA data craniocaudally to restrict coverage from the C1 vertebra to the vertex; (4) elastically aligns an anatomic template of the human head with the CTA data; (5) warps templates of relevant anatomic structures (e.g., bones and blood vessels) onto the CTA to create masks; (6) removes the skull base and calvarium using the bone mask; (7) identifies intracranial vessels and dichotomizes them into small and large diameter groups; (8) determines the vessel density by assessing the length of large caliber vessels in the suprasellar cistern (supraclinoid ICA) and proximal Sylvian cistern (M1-MCA) as well as the sum of density values (in Hounsfield units) of the voxels constituting these vessels; (9) determines vessel density for small caliber vessels (distal M1, M2, and M3 segments) further distally in and adjacent to the Sylvian cisterns, (10) performs left-right comparison to determine the relative vessel density ratio, first within the suprasellar and proximal Sylvian cistern, then progressing further distally; (11) creates axial, coronal, and sagittal maximum-intensity projections of the intracranial vasculature from the bone-masked CTA: (12) highlights the areas of reduced relative interhemispheric vessel density on these MIPs applying the following color-coded thresholds: 75% to 80% (blue), 60% to 74% (green), 45% to 59% (yellow), and <45% (red); and (13) sends these MIPs as de-identified output maps to the picture archiving and communication system. Application of the 4 different thresholds is simultaneous and fully automated.

The processing time taken to complete these steps was recorded for each patient. No further training of the algorithm occurred during the study period.

Statistical Analysis

All statistical analyses were performed using a software package (MedCalc Version 17.2, MedCalc Software bvba, Ostend, Belgium, 2017).

Receiver operating characteristic (ROC) analysis was performed to determine the sensitivity, specificity, positive predictive value (PPV), negative predictive value (NPV) and area-under-the ROC curve (AUC) of the algorithm for detection of:

1. An intracranial LVO; and
2. Either an intracranial LVO or M2 segment occlusion.

A vessel density threshold of <75% (inclusive of the 60%-75, 45%-59%, and <45% thresholds) was used in this study for LVO detection, as this was recommended by the software developers based on their prerelease testing.

Confidence intervals were calculated using a bootstrap procedure with 10000 samples with replacement.

Results 501 consecutive patients meeting the inclusion criteria had undergone a multimodal CT with CTA and CTP between Jan. 1, 2017 and 31 Dec. 2018. 8 were excluded due to a technically inadequate CTA (poor contrast bolus in 5 and severe motion degradation in 3). 16 (including two with an LVO) were excluded because thin-slice CTA was unavailable on PACS.

CTAs from 477 patients were analyzed: 271 male (median age70, IQR 59.5-79) and 206 female (median age 71.5, IQR 60-83). Patients' baseline characteristics and the details of vessel occlusions are shown in Tables 1 and 2 respectively.

TABLE 1

Patient Characteristics

| | Number | Age, y | NIHSS Median (Interquartile Range) | Male | Intravenous TPA Given | Thrombectomy Performed |
|---|---|---|---|---|---|---|
| All Patients | 477 | 71 (60-80) | 6 (2-9) | 271 (56.8%) | 68 | 57 |
| Intracranial anterior circulation large vessel occlusion | 78 | 74 (65-82) | 14 (10-18) | 46 (59.0%) | 39 | 52 |
| M2 segment middle cerebral artery occlusion | 28 | 78 (70-88) | 7 (5-11) | 12 (42.9%) | 2 | 2 |
| No intracranial anterior circulation large vessel or M2 occlusion (controls) | 371 | 70 (58-80) | u | 213 (57.4%) | 27 | 0 |

TABLE 2

Patient Characteristics

| | | Number |
|---|---|---|
| LVO | | 76 |
| | M1 segment middle cerebral artery only | 46 |
| | Intracranial internal carotid artery only | 21 |
| | Supraclinoid, including terminus | 14 |
| | Supraclinoid, proximal to terminus | 3 |
| | Petrous-Clinoid segments | 4 |
| | Tandem M1-middle cerebral artery and intracranial internal carotid artery | 11 |
| M2 segment of middle cerebral artery occlusions | | 28 |
| Location | Proximal | 24 |
| | Distal | 4 |
| Division | Both | 4 |
| | Dominant | 13 |
| | Co-dominant | 4 |
| | Nondominant | 7 |

LVO indicates large vessel occlusion.

All cases were processed in under 5 minutes. The mean processing time was 158 seconds (IQR 150-167 seconds).

1. Intracranial LVO Detection

The results of ROC analysis for LVO detection are given in Table 3.

TABLE 3

Results of Receiver Operating Characteristic Analysis for LVO Detection at the Optimal Threshold (<75%)

| Site of Occlusion | Sensitivity* | Specificity* | PPV* | NPV* | Youden* | AUC* |
|---|---|---|---|---|---|---|
| Intracranial large vessel (n = 78) | 0.94 (0.86-0.98) | 0.76 (0.72-0.80) | 0.43 (0.39-0.48) | 0.98 (0.96-0.99) | 0.70 (0.62-0.76) | 0.85 (0.81-0.88) |
| M2-segment middle cerebral artery (n = 28) | 0.86 (0.67-0.96) | 0.68† (0.63-0.72) | 0.14† (0.12-0.17) | 0.99† (0.97-1.00) | 0.54 (0.36-0.64) | 0.77 (0.70-0.84) |
| Intracranial large vessel or M2 segment middle cerebral artery (n = 106) | 0.92 (0.85-0.96) | 0.81 (0.77-0.85) | 0.58 (0.52-0.63) | 0.97 (0.95-0.98) | 0.72 (0.65-0.79) | 0.86 (0.83-0.90) |

AUC indicates area-under-the ROC curve; NPV, negative predictive value; LVO, large vessel occlusion; and PPV, positive predictive value.
*Values within parentheses represent the 95% CI.
†With LVOs included. Sensitivity, specificity, PPV, and NPV were 0.86, 0.81, 0.25, and 0.99, respectively when the 78 patients with LVOs were excluded from analysis.

Figure 13A:
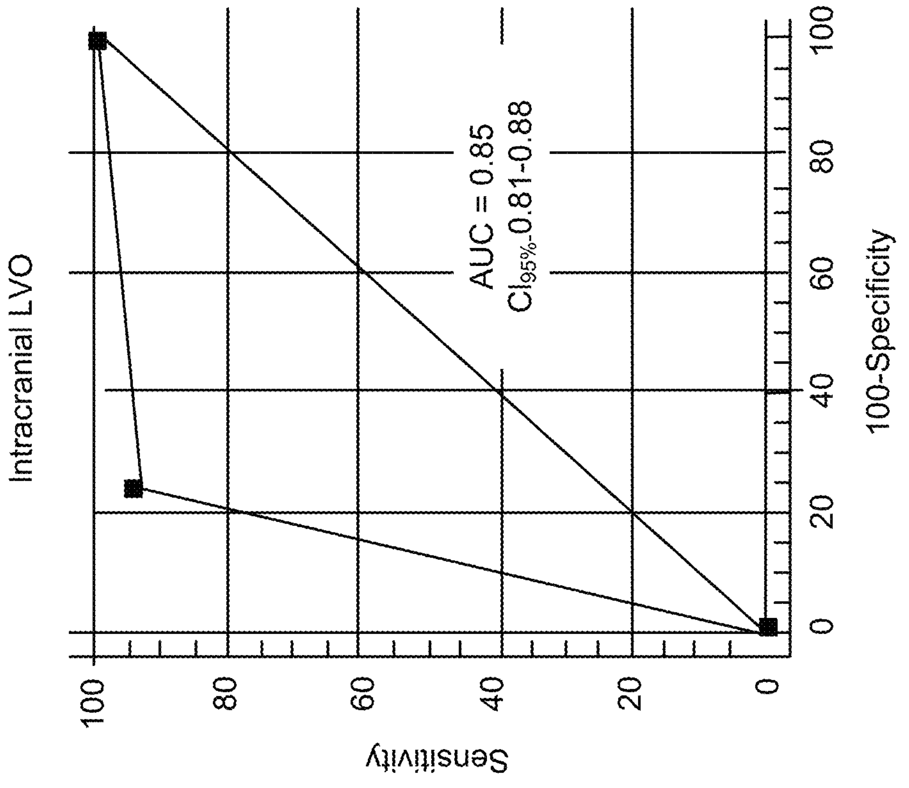
FIG. 13A shows ROC curves for detection of intracranial LVOs and FIG. 13B shows ROC curves for detection of either an intracranial LVO or M2-MCA occlusion.

Of the 78 patients with an LVO in the study population, 73 (93.6%) were correctly identified by the algorithm, yielding a sensitivity of 0.94 ($CI_{95\%}$0.86-0.98) and a specificity of 0.76 ($CI_{95\%}$0.72-0.80). The negative predictive value was very high (0.98, $CI_{95\%}$0.96-0.99). The ROC curve is shown in FIG. 13A.

On post hoc analysis, the algorithm did not miss any LVO associated with poor collateral status (as indicated by lack of opacification of the M2 and M3 segments distal to the LVO).

A.) ICA Occlusions

An LVO was correctly identified in 31/32 (96.9%) patients with an intracranial ICA occlusion. There were 11 patients with tandem ICA and M1-MCA occlusions and 14 patients with isolated supraclinoid ICA occlusions that involved the ICA terminus (including one with incomplete occlusion). These were all correctly identified using the <45% threshold (example shown in FIG. 10, Upper Left and Right).

In 3 patients with supraclinoid ICA occlusions that spared the ICA terminus, the ICA terminus and M1-MCA were opacified by cross-flow via the patent anterior communicating segment. In these patients, the proximal part of the supraclinoid ICA was not opacified, resulting in reduction in the vessel density ratio that allowed detection by the algorithm, albeit using a higher threshold of <60%.

The algorithm correctly identified 3 out of 4 petrous-cavernous segment ICA occlusions using the <45% threshold. In these patients, the caliber and luminal density of the supraclinoid ICA was sufficiently reduced compared with the contralateral side (FIG. 11) to allow detection. In the remaining patient with a petrous segment ICA occlusion, which was missed by the algorithm, the supraclinoid ICA was well opacified, with no reduction in caliber or luminal density because of collateral supply from the external carotid artery via the ophthalmic artery.

B.) M1 Occlusions

Of the 46 patients with an isolated M1-MCA occlusion, 42 (91.3%) were correctly identified by the algorithm, 33 were identified using the <45% (red) threshold, while 5 were identified using the <60% (yellow) threshold and 4 were identified using the <75% (green) threshold.

Of the 9 patients who were identified using the green or yellow thresholds, 6 had short segment occlusions (measuring <8 mm in length). These patients had good opacification of the M2 segments distal to the occlusion (therefore a smaller relative vessel density reduction), indicating good collateral status.

Figure 10:
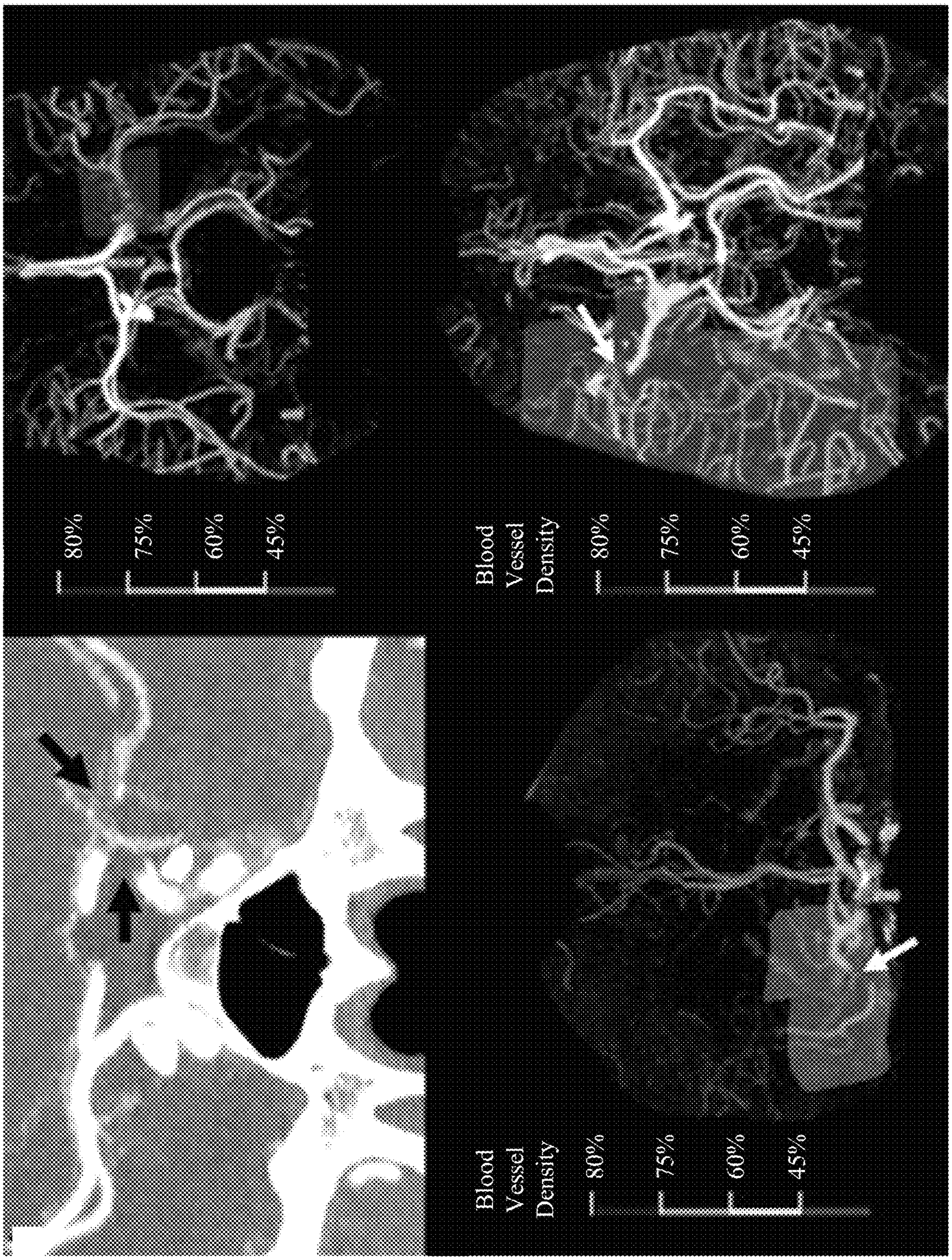
FIG. 10 shows images of blood vessels of the brain where large vessel occlusion detection was performed according to one or more implementations described herein.

Two examples are shown in FIG. 10, Lower Left and Right. The remaining 3 patients also had good collaterals as indicated by reconstitution of the proximal M2 segments.

Four M1-MCA occlusions were missed: one incomplete, one short segment (5 mm length), and the other 15 mm long with reconstitution of the proximal M2 segments via collaterals. The remaining case was a long-segment proximal M1-MCA occlusion with reconstitution of the anterior temporal branch and proximal M2 segments, again indicating good collateral status. ***

2. LVO and M2-MCA Occlusion

Figure 13B:
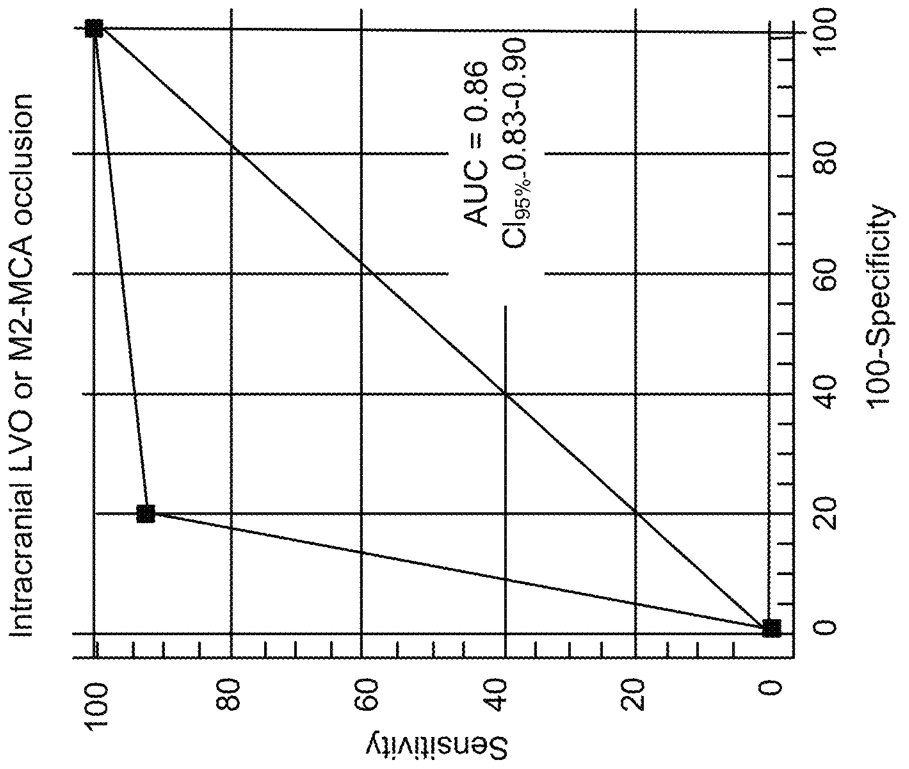

The results of ROC analysis for detection of either an LVOs or an M2-MCA occlusion are given in Table 3 (the ROC curve is shown in FIG. 13(B)). The sensitivity of 0.92 (95% CI, 0.86-0.96) was lower than for purely LVO detection but the specificity of 0.81 (95% CI, 0.77-0.85) was higher. The NPV was 0.97 (95% CI, 0.95-0.98).

Of the 28 M2-MCA occlusions, 4 were not detected: 2 short-segment proximal occlusions with good collaterals (indicated by opacification of the M2 segment further distally), a small nondominant M2 segment occlusion and a distal nondominant M2 occlusion.

3. False Positives

There were 71 false positives. A cause of asymmetrical vascular density in the supraclinoid and Sylvian cisterns was identified in 64 of these patients. Ipsilateral decreased vascular density was caused by: chronic M1-MCA stenosis (n=5); high-grade supraclinoid ICA stenosis (n=1); cervical ICA occlusion with decreased density and caliber of the supraclinoid ICA (n=1); old ipsilateral MCA territory infarction with attenuation of the M1 or M2 segments (n=4); and early bifurcation of the MCA (n=12).

False positives also resulted from the following causes of contralateral increased vascular density (FIG. 12); a large anterior temporal branch (n=7); asymmetrically large or unilateral posterior communicating segment (n=15); hyperperfusion (n=3; 2 patients with hypervascular tumors and 1 with seizures); large MCA aneurysm (n=1); large supraclinoid ICA supplying both anterior cerebral arteries (n=2); and opacified venous structures (n=13).

Cervical ICA Occlusions

There were 8 patients who had an isolated cervical ICA occlusion. The algorithm diagnosed an intracranial LVO in one of these patients whose supraclinoid ICA was decreased in density (15%) and caliber (50%) compared with its contralateral counterpart. The ipsilateral supraclinoid ICA had only mildly decreased density and caliber in the remaining 7 patients.

Discussion

This study retrospectively evaluated the performance of an automated LVO detection tool in a cohort of consecutive patients who underwent multimodal CT for a suspected acute ischemic stroke at a large regional hospital. Our results demonstrate that a fully automated software algorithm can detect intracranial anterior circulation LVOs with high diagnostic sensitivity (0.94) and negative predictive value (0.98), and moderately high specificity (0.76). The study also shows that this can be achieved in very short computing times, under 3 minutes, making this tool ideally suited to the emergent clinical setting.

The sensitivity of the algorithm falls within the range previously reported for neuroradiologists of varying levels of experience (0.94-1.0). The specificity is, however, much lower than 0.95 to 0.98 achieved by experienced human readers. Vascular asymmetry, which caused most false positives, can be easily distinguished from an LVO by radiologists and neurologists. We therefore do not advocate replacing experienced human readers with the automated LVO detection tool. Instead, given its high NPV, we propose using this software as a clinical decision support tool to screen the multimodal CTs of stroke patients.

It can alert the treating neurologist and reporting radiologist of a potential LVO and expedite diagnosis by prompting evaluation of the patient's imaging as a high priority. Such a tool would be particularly valuable in regional and peripheral centers such as ours, which do not have the resources and experienced staff to provide around-the-clock on-site multimodal stroke CT interpretation. While all CTAs are ultimately read by a radiologist, they are not always assigned the highest priority, especially after-hours where resources are limited. Often, there is only one on-call radiologist or resident at smaller centers and in countries where subspecialist radiology is not practiced. In this setting, other emergent scans such as trauma may be prioritized ahead of a stroke patient's multimodal CT, resulting in delayed diagnosis. The authors have encountered this issue repeatedly in clinical practice. The algorithm fully automates LVO detection and generates an output within 3 minutes in 75% of cases (and 5 minutes in all cases). This ensures that the positive findings are brought to the reporting radiologist, teleradiologist, or resident's attention within 5 minutes of scanning, which in turn expedites diagnosis. Currently, assessment is often delayed until CTA reformats are completed and the study posted to the radiologist worklist by the CT technologist.

An added benefit of the algorithm for hospitals such as ours that do not have an on-site thrombectomy service is notification of the nearest thrombectomy center. This in turn expedites mobilization of the clot retrieval team and treatment of eligible patients, thereby ensuring the best possible outcomes. Notification is currently reliant upon the local neurologist or emergency physician contacting the thrombectomy center, which can add to delay.

The algorithm may also be a valuable diagnostic support tool. While experienced neuroradiologists have a high sensitivity for detection of LVOs, reported to be 75% to 98%, the diagnostic performance of neurologists and trainees may be considerably lower (63% in 1 study). At many centers around the world, such as ours, the acute review of multimodal stroke CTAs is performed by trainee radiologists and neurologists, and these studies are second read by a radiologist (often a generalist) at a later time. Also, even experienced radiologists do miss LVOs. The tool can prompt a second look in these cases, potentially averting a clinically significant miss and consequent harm. While the cost of the software is low, that of a missed or delayed diagnosis of an LVO, where the patient misses out on beneficial treatment and suffers significant neurological disability, is high. Therefore, while we have not performed a specific intervention to assess whether or not the use of the LVO detection software is cost effective, our experience with delayed and missed diagnosis of LVOs suggests that it is.

To our knowledge, there is no previously published complete study that has evaluated the diagnostic performance of an automated LVO-detection algorithm. Two abstracts are available for evaluation of another LVO-detection software: the sensitivity of 0.85 to 0.97 reported in these abstracts is comparable to ours, while the reported specificity had a wide range (0.52-0.83). The cohort of patients in those investigations was randomly selected from acute ischemic stroke patients at a number of comprehensive stroke centers and enriched with LVOs. Our study cohort consisted of consecutive patients presenting to a regional hospital with a suspected acute ischemic stroke and is therefore likely to be more heterogenous, with a lower prevalence of LVOs because clinical triage is less refined than at a comprehensive stroke center. By using a noncurated dataset, we have tested our algorithm and determined its diagnostic performance in a real-world context. Our study cohort is also felt to be more representative of the target population for LVO-detection tools.

The LVO detection algorithm evaluated in this study detects hemispheric differences in vessel density within the suprasellar and Sylvian cisterns. Vessel density is affected by the length, caliber, and number (spatial density) of opacified vessels as well as the density of luminal opacification (measured in Hounsfield units). An LVO results in vessel non-opacification, which in turn reduces ipsilateral vessel density. The resultant asymmetry is detected by the algorithm. For example, supraclinoid ICA occlusions involving the ICA terminus were all detected by the algorithm, using the <45% threshold. In these patients, nonopacification of the supraclinoid ICA and at least the proximal part of the M1-MCA resulted in severe vessel density reduction. Similarly, patients with tandem M1-MCA and intracranial ICA occlusions, who had extensive arterial nonopacification, were detected using the <45% threshold. Patients with an ICA occlusion that spared the terminus, who also had a patent anterior communicating segment, displayed milder vessel density reduction because cross-flow opacified the distal supraclinoid ICA. The vessel density reduction was sufficient for the algorithm to detect an LVO but required use of a higher threshold in these patients.

False negatives for LVO detection could be explained by insufficient relative vessel density reduction to allow detection by the algorithm. This occurred with short-segment (Figure VI) and incomplete M1-MCA occlusions, and in patients with good collaterals where there was M1 or M2 segment opacification distal to the occlusion. High collateral grade, with vessel opacification distal to the occlusion (therefore a smaller reduction in relative vessel density), also accounted for the nine M1-MCA occlusions that were not detected using the lowest (<45%) threshold. These patients with robust collaterals are more likely to be slow progressors whose infarct growth is less time sensitive. Expediting detection may therefore be less critical in this group. None of the patients in whom the algorithm missed an LVO had a poor collateral grade. Poor collaterals are associated with fast progression: therefore, this is the group in which fast diagnosis is most important since rapid reperfusion is necessary for tissue salvage.

The only other false negative was a petrous ICA occlusion, which highlights an important limitation of the algorithm. Petrous-clinoid ICA occlusions cannot be directly detected because of poor performance of the bone mask at the skull base. The supraclinoid ICA was normally opacified in this patient, precluding detection by the algorithm. While the number of patients (4) with skull-base ICA occlusions in this study was too small for meaningful analysis of the accuracy of the LVO-detection tool in this group, it is also reflective of the low prevalence of petrous-clinoid ICA occlusions in the acute ischemic stroke population. Cervical ICA occlusions also pose a challenge for the algorithm because the neck vessels are not interrogated, and these occlusions do not necessarily result in reduced density or caliber of the supraclinoid ICA. Current guidelines do not indicate thrombectomy for patients with isolated cervical ICA occlusions, therefore identifying these using the LVO-detection tool is perhaps less critical at present. It is important that radiologists and neurologists are cognizant of the presence and causes of false negatives and remain vigilant in their interpretation of CTAs even when the algorithm gives a negative result.

The algorithm was able to detect most M2-MCA occlusions. While sensitivity decreased slightly to 0.92, specificity increased to 0.81 and NPV remained approximately stable when M2-MCA occlusions were included. There is evidence of improved functional outcomes with thrombectomy compared with standard medical management in patients with M2-MCA occlusions. Current guidelines therefore state that endovascular thrombectomy can be considered in carefully selected patients with M2-MCA occlusions. In particular, thrombectomy may be justified to achieve rapid reperfusion in patients with severe neurological deficits and ischemia of highly eloquent brain regions. In addition, in patients with M2-MCA occlusions who are ineligible for intravenous thrombolysis (e.g., because of presentation beyond the 4.5 hours window), thrombectomy is the only available reperfusion therapy. It could therefore be argued that an LVO-detection tool should also identify M2-MCA occlusions.

False positives were caused by vascular asymmetry related to developmental variants (e.g., early unilateral bifurcation of the ipsilateral MCA, which produces asymmetry in vessel caliber, and a unilateral or large contralateral posterior communicating segment), chronic steno-occlusive disease, and contralateral hyperperfusion (e.g., because of hypervascular tumors). Since the algorithm does not differentiate between venous and arterial structures, asymmetry in venous structures such as the deep and superficial middle cerebral veins can cause false positives. This can be avoided by measures that prevent venous contamination of the CTA such as rapid contrast bolus injection and performing CTA before CTP.

A limitation of this study is that it is a single-center experience. Further investigation of the utility of the tool in a multicenter study that involves multiple regional spoke hospitals and a clot retrieval hub is planned.

Conclusions

The algorithm evaluated in this study had high sensitivity and NPV for LVO detection in a cohort of patients who underwent multimodal CT for a clinically suspected stroke. M2-MCA occlusions were also reliably detected, which is important since these patients can be considered for thrombectomy. While sensitivity is in the range previously reported for neuroradiologists, the specificity is much lower than that of experienced human readers. The algorithm should therefore be used as a screening tool to expedite diagnosis rather than a surrogate for an experienced human reader. Fast processing times make its use feasible in the emergent clinical setting.

Figures

Figure 14:
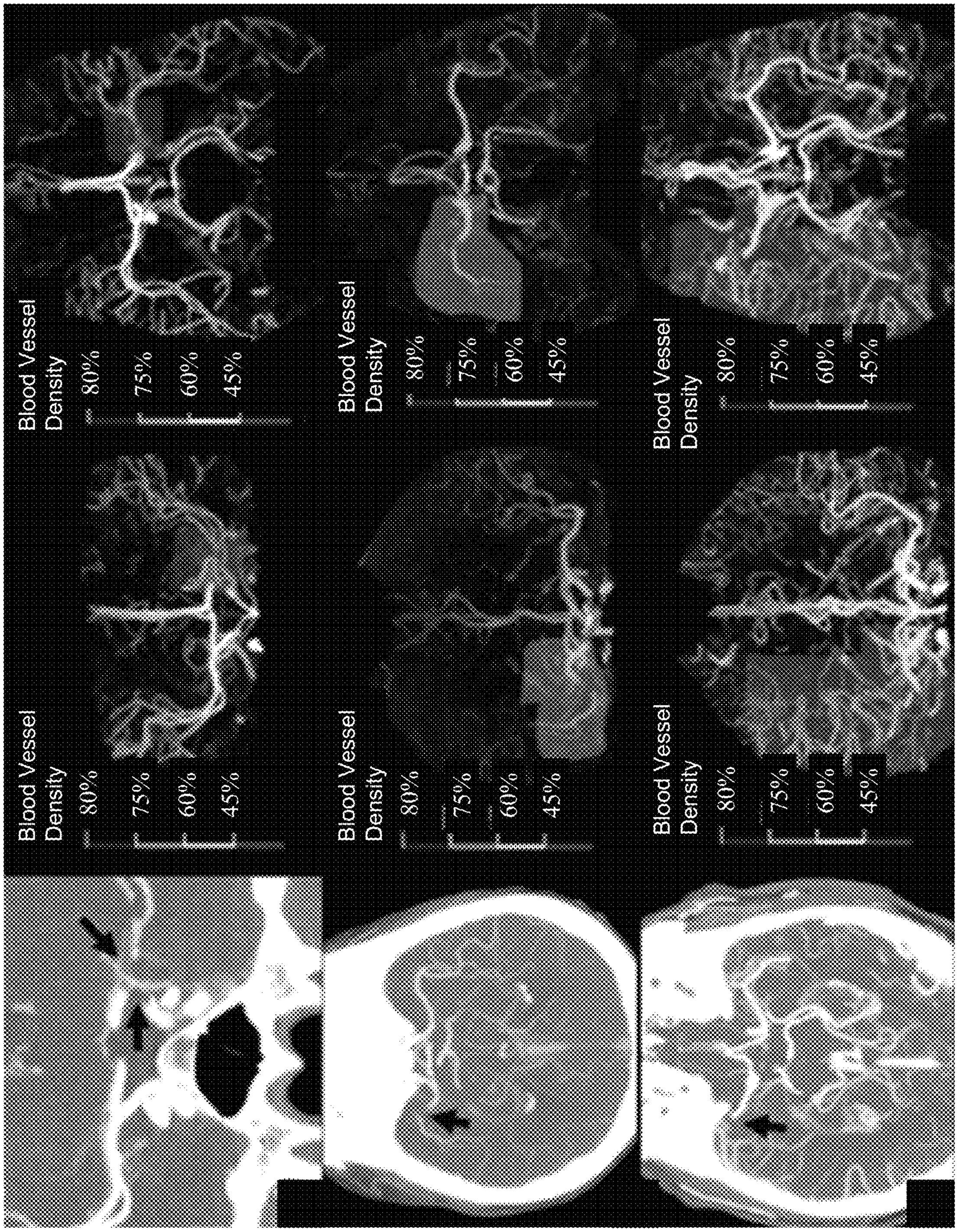
FIG. 14 shows images of blood vessels of the brain where large vessel occlusion detection was performed according to one or more implementations described herein.

FIG. 10. Examples of large vessel occlusion detection by the algorithm (an expanded version is shown in FIG. 14). Upper Left, Coronal computed tomography angiography maximum intensity projection (MIP) shows terminal internal carotid artery and proximal M1 segment of the middle cerebral artery (M1-MCA) occlusion (arrows) in a 44 y-old woman who presented with sudden onset right-sided weakness and dysphasia. Upper Right, The resulting severe vessel density reduction (to <45% contralateral) in the suprasellar cistern allowed the algorithm to detect a large vessel occlusion. Software output of an axial bone-masked MIP with the area of vessel density reduction highlighted in red. Lower Left, Eighty-eight-year-old woman who presented with sudden onset left-sided weakness. Software output of a coronal MIP showing short-segment distal right MCA-M1 occlusion (arrow) with the area of vessel density reduction highlighted in yellow (<60% contralateral). One of the M2 segments was opacified distal to the occlusion, therefore the vessel density reduction was less than in the previous case necessitating use of a higher threshold. Lower Right, Sixty-one-year-old man presenting with sudden onset left-sided weakness. Software output showing a short-segment distal right M1-MCA occlusion (arrow) with the area of vessel density reduction highlighted in green (<75% contralateral). Sampling of a larger region was required to identify vessel density reduction, which was less marked than in the previous examples due to good opacification of the M2 and M3 segments distal to the short segment occlusion (indicating good collaterals). The pseudocontrast because of color overlays make the vessels seem more conspicuous than on corresponding conventional MIPs.

Figure 11:
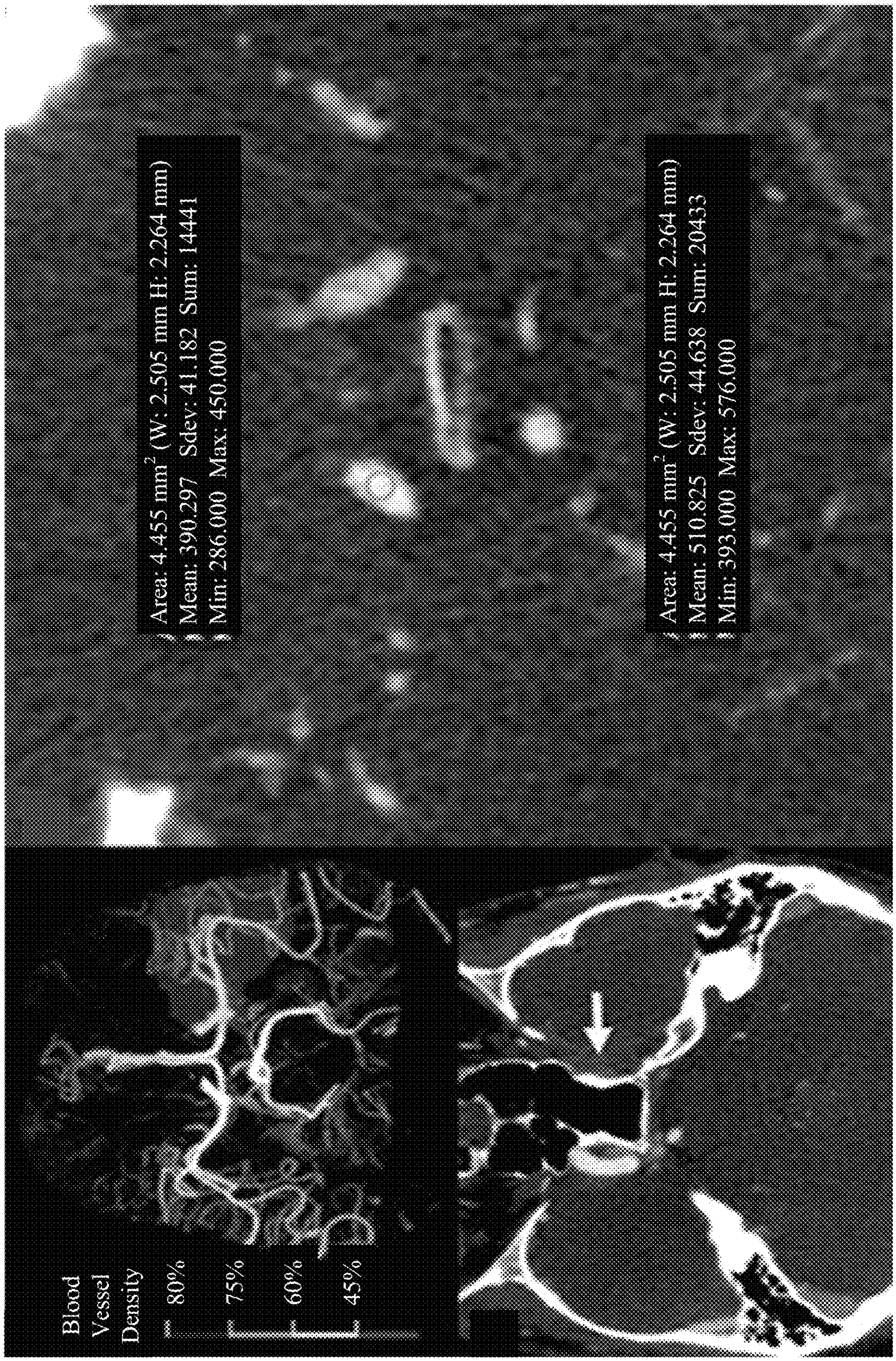
FIG. 11 shows images of a brain of a fifty-nine-year-old man with a left petrous internal carotid artery (ICA) occlusion secondary to dissection.

FIG. 11. Fifty-nine-year-old man with a left petrous internal carotid artery (ICA) occlusion secondary to dissection. Upper Left, Software output with an axial bone-subtracted maximum intensity projection (MIP). Vessels in the suprasellar and Sylvian cisterns are highlighted in red, indicating severe density reduction compared with the contralateral side despite the normal appearance on the MIP. Lower Left, Axial 0.8 mm computed tomography angiography showing nonopacification of the left cavernous ICA (arrow). Right, The left supraclinoid ICA had a lower luminal density (mean density 390 Hounsfield units, top text box) than the right (mean density 510 Hounsfield units, bottom text box), which allowed the algorithm to detect the large vessel occlusion (LVO).

Figure 12:
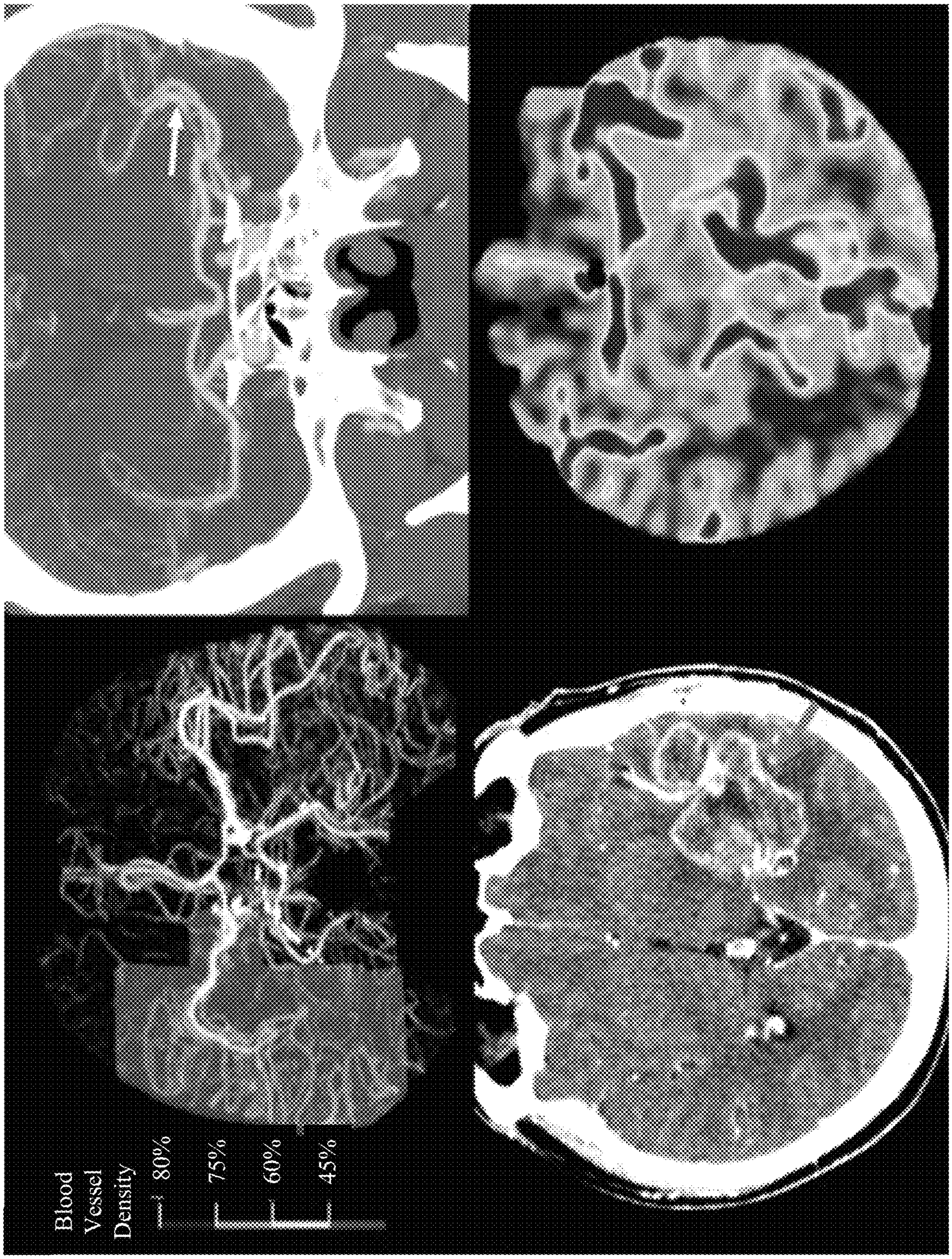
FIG. 12 shows images of a brain of an individual where a false positive determination was made in a 50-y-old man presenting with dysphasia and right-sided weakness.

FIG. 12. Example of a false positive in a 50-y-old man presenting with dysphasia and right-sided weakness. Upper Left, Software output showing right-sided vessel density reduction to <60% contralateral when vessels in the suprasellar and Sylvian cistern are interrogated. Upper Right, Coronal computed tomography angiography maximum intensity projection (MIP) (20 mm) showing an increase in vessels in the left Sylvian cistern. Lower Left, Contrast-enhanced computed tomography axial image showing the causative hypervascular tumor (glioblastoma, arrowed) in the left temporal lobe and insula Lower Right, Elevated relative cerebral blood flow and engorgement of the ipsilateral middle cerebral artery are seen on the blood flow map.

Supplemental Material

CT Technique

For CTP, 50 mL of non-ionic contrast agent (350 mg iodine/mL, iohexol Omnipaque 350, GE Healthcare, Wisconsin, USA) was injected intravenously, followed by a 50 mL saline flush at 5 mL/s. Perfusion CT data was acquired using an axial approach consisting of 35 consecutive scans of the brain with the following parameters: 80 kV tube voltage, 160 mA tube current, 2.05 s mean temporal resolution, 500 ms gantry rotation time, 80 mm z-axis coverage, 1.5 mm slice collimation and 512×512 acquisition matrix. Images were reconstructed using an iterative reconstruction (iDose) factor of 4 at 10 mm slice thickness and processed using a commercially available software (RAPID, iSchemaView, Menlo Park, California).

FIG. 13. ROC curves for A, detection of intracranial LVOs and B, detection of either an intracranial LVO or M2-MCA occlusion. The sensitivity decreases slightly but the AUC increases due to improved specificity when M2-MCA occlusions are included.

FIG. 14: Examples of large vessel occlusion detection by the algorithm. Upper Left, Middle, Right: 44-year-old woman who presented with sudden onset right sided weakness and dysphasia. Upper Left, Coronal CTA MIP shows terminal ICA and proximal M1-MCA occlusion (arrows). The resulting severe vessel density reduction (to <45% contralateral) in the suprasellar cistern allowed the algorithm to detect an LVO. Upper Middle and Upper Right, The software output of axial and coronal bonemasked MIPs, with the areas with vessel density reduction highlighted in red. Middle Left, Center, Right: 88-year-old woman presenting with sudden onset left sided weakness Middle Left, Axial CTA MIP showing a short segment distal right MCA-M1 occlusion (arrow). One of the M2 segments is filled but attenuated. Middle Center and Middle Right, Software output highlighting the areas of vessel density reduction (to <60% contralateral). Lower Left, Middle, Right: 61-year-old man presenting with sudden onset left sided weakness. Lower Left, Axial CTA MIP showing short-segment distal right M1-MCA occlusion (arrow). Lower Middle and Lower Right, Software output highlighting an extensive area in green, within which vessel density was reduced to <75% contralateral. Sampling of a larger region was required to identify vessel density reduction, which was less than in the previous examples due to opacification of the M2 and M3 segments distal to the short segment of the occlusion (indicating good collaterals). The pseudocontrast due to color overlays make the vessels appear more conspicuous than on corresponding conventional MIPs.

Figure 15:
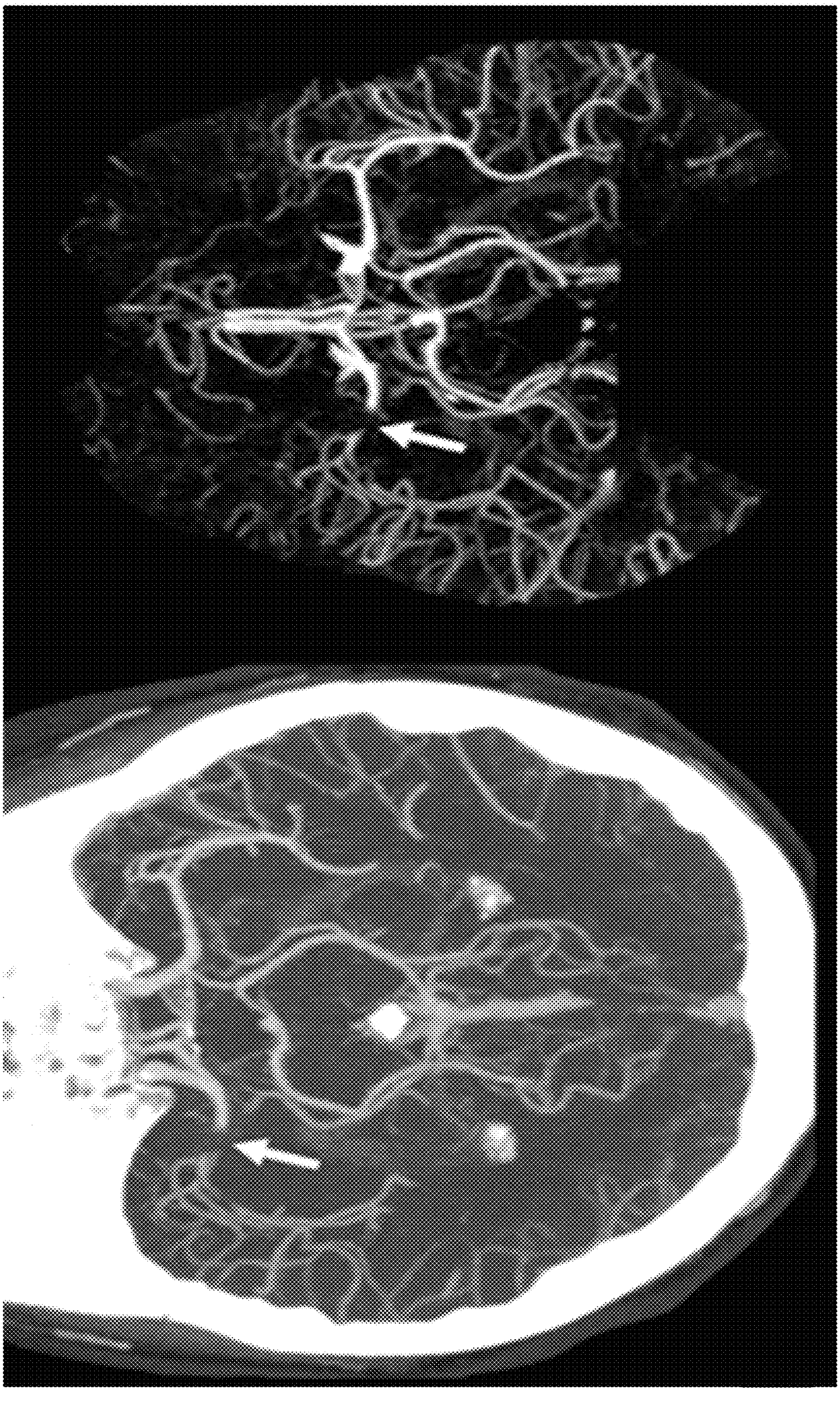
FIG. 15 shows images of blood vessels where a false negative determination was made.

FIG. 15 false negative. Left. Axial CTA MIP image showing a short segment right distal M1-MCA occlusion with reconstitution of the proximal M2 segments via leptomeningeal collaterals. Right. The algorithm failed to detect this LVO.

Example 2

Methods

For this retrospective study, data were pooled from: two stroke trials, DEFUSE 2 (n=62: July 2008-September 2011) and 3 (n=213; May 2017-May 2018); a cohort of ECR candidates (n=82; Aug. 2, 2014-Aug. 30, 2015) and normals (n=111: Jun. 6, 2017-Jan. 28, 2019) from a single quaternary center; and 'code stroke'-patients (n=501: Jan. 1, 2017-Dec. 31, 2018) from a single regional hospital. All CTAs were assessed by the automated algorithm. Consensus reads by two neuroradiologists served as the reference standard. ROC analysis was used to assess diagnostic performance of the algorithm for detection of: 1.) anterior circulation LVOs involving the intracranial internal carotid artery (ICA) or M1 segment middle cerebral artery (M1-MCA); 2.) anterior circulation LVOs and proximal M2 segment middle cerebral artery (M2-MCA) occlusions and; 3.) individual segment occlusions.

Results

CTAs from 926 patients (median age 70 years IQR: 58-80; 422 females) were analyzed. 395 patients had an anterior circulation occlusion LVO or M2-MCA occlusion (NIHSS 14 [median], IQR. 9-19). Sensitivity and specificity were 97% and 74%, respectively, for LVO detection, and 95% and 79%, respectively, when M2 occlusions were included. On analysis by occlusion site, sensitivities were 90% (M2-MCA), 97% (M1-MCA), and 97% (intracranial ICA) with corresponding area under the ROC curves of 0.874 (M2), 0.962, (M1), and 0.997 (intracranial ICA).

Conclusions

Intracranial anterior circulation LVOs and proximal M2 occlusions can be rapidly and reliably detected by an automated detection tool, which may facilitate intra and inter-institutional work-flows and emergent imaging triage in the care of stroke patients.

Materials and Methods

This retrospective study was approved by the IRBs of the participating regional and quaternary hospitals, who waived the requirement for informed consent.

a. Patient Selection

A total of 969 patients were included in this retrospective study. The patient population comprised 5 individual cohorts which constituted a well-represented sample of scanner models from all major CT vendors and typical variants of CTA protocols seen at hospitals: Two hundred seventy-five patients pooled from DEFUSE 2 (Diffusion and Perfusion Imaging Evaluation for Understanding Stroke Evolution: n=62: July 2008-September 2011) and DEFUSE 3 (n=213; May 2017-May 2018), 2 large multi-center stroke trials; 193 patients came from a single quaternary center of which 82 were patients who had been imaged as potential ECR candidates (Aug. 2, 2014-Aug. 30, 2015), and 111 were imaged for nonstroke related indications (Jun. 6, 2017-Jan. 28, 2019) with normal anterior circulation. The fifth cohort was a consecutive series of 501 patients who had CTA as part of a code stroke work up at a regional hospital that is a primary stroke center (Jan. 1, 2017-Dec. 31, 2018). Note that for DEFUSE 2 and 3, only the subset of consented patients who had undergone acute CTA were used. Data from the patients in the fifth cohort were used for follow-on study which has already been published.

Forty-three patients (4.4%) were excluded due to (1) screen failures (n=4, from DEFUSE 2); (2) CTA not being included in the acute CT protocol (n=7); (3) inadequate data format (thin slice CTA raw data unavailable); and (4) the CTA being deemed by an experienced neuroradiologist (S.A.) to be technically inadequate therefore of insufficient quality to allow accurate interpretation by a human reader (n=15 with severe motion in 3, poor/no contrast bolus in 8 and incomplete coverage of the intracranial arteries in 4).

The remaining 926 patients (age 70 [median; interquartile range (IQR)], 58-80 years) were analyzed, of which 504 were female (age 69 IQR, 58-78) and 422 male (age 71.

IQR, 59-82). Five hundred thirty-one of these patients, who were imaged for a diagnostic workup of their cervico-cerebral vasculature, had either no evidence of an anterior circulation vessel occlusion or distal (M3/M4 segments) occlusions only, and for this study were considered controls. Based on CTA expert reads, the remaining 395 patients had an occlusion in the anterior circulation at the following location:

I. Single site (n=241): cervical ICA (n=15); intracranial ICA (n=16); M1-MCA (n=161); M2-MCA (n=37); and distal MCA (n=12).

II. Tandem lesions (n=154): Any ICA+M1 (n=124); Any ICA+M2 (n=8); M1+M2 (n=5); cervical ICA+intracranial ICA (n=9); and M2+distal MCA (n=8).

Of those 395 patients with occluded vessels, 15 patients had isolated cervical ICA occlusions, and 60 had M2-MCA occlusions without any intracranial LVOs. Of the remaining 320 patients with intracranial LVOs, 16 had isolated intracranial ICA, 161 had isolated M1-MCA occlusions, and 143 had tandem/multiple occlusions: M1+M2 (n=5); cervical ICA+M1 (n=21); intracranial ICA+M1 (n=103); intracranial ICA+M2 (n=5); and intracranial and cervical ICA (n=9).

b. Reference Standard

For patients enrolled in DEFUSE 2 and 3, the presence and exact location of an occlusive lesion had been previously determined by the investigators and was verified by a neuroradiologist with 8 years post-fellowship experience. For the remaining patients, 2 neuroradiologists, with 9 years post-fellowship experience, evaluated the multimodal CTs including CTA for the presence and site of an occlusive lesion, in consensus, with all clinical and imaging data (including perfusion imaging) available for review. Any disagreements were resolved by review of all available imaging for the patient, including perfusion. These neuroradiologist reads served as the reference standard against which the diagnostic performance of the algorithm was assessed.

c. Algorithm Description

The underlying concept of the LVO detection presented here relies on software that performs elastic registration of 3 prespecified anatomic assessment regions (R1, R2, and R3) onto and then tubular filtering of CTAs to detect reduced opacification of anterior intracranial vessels relative to the contralateral hemisphere. This algorithm was implemented into RAPID 4.9.1 (iSchemaView, Menlo Park, CA) and ran on a conventional computer environment (2× Intel Xeon E5-2680 2.7 GHz CPUs with 8 cores and hyperthreading each, 64 GB RAM, CentOS 7 Linux). The algorithm used in this study has received Conformité Européenne labeling and has been cleared by the US Food and Drug Administration. It was used as provided by the vendor, without any modification or any further pre- or postprocessing. Relative vessel density thresholds for LVO detection can be chosen arbitrarily by the user, but for this study the software's default values were used: <80% to 75% (BLUE), <75% to 60% (GREEN), <60% to 45% (YELLOW), and <45% (RED).

Statistical Analysis

The primary outcome was the diagnostic performance of the algorithm for detecting intracranial LVOs. Sensitivity and specificity for detecting an intracranial LVO were assessed using ROC analysis. Specifically, the algorithm's ability to detect the presence of CT angiographic signs of an LVO—as indicated by absence or severe reduction of arterial opacification—was assessed for the intracranial ICA and the M1-MCA. The assessment of diagnostic performance was then repeated with proximal M2-MCA occlusions added to the LVO group.

Bootstrap analysis (1000 repeats) was used to compute 95% CIs for all parameters. The area-under-the-ROC-curve (AUC) was used in conjunction with the DeLong algorithm for calculating the SE of the AUC. As the software is primarily intended to be used as a screening tool, a diagnostic sensitivity of ≥95% was made a requirement.

Secondary outcomes were diagnostic performance of the algorithm for detecting LVOs in specific vessel segments and the processing speed. The algorithm's diagnostic performance was evaluated for detecting occlusions at the following subsites: (1) intracranial ICA (including terminal ICA); (2) M1-MCA; and (3) proximal M2-MCA. For analysis of each occlusion site, occlusions at the other 2 subsites were excluded.

All statistical testing was performed using MedCalc (MedCalc Version 17.2, MedCalc Software. Ostend, Belgium, 2017). An a level of 0.05 was used to indicate significance for all tests.

Results

Figure 16:
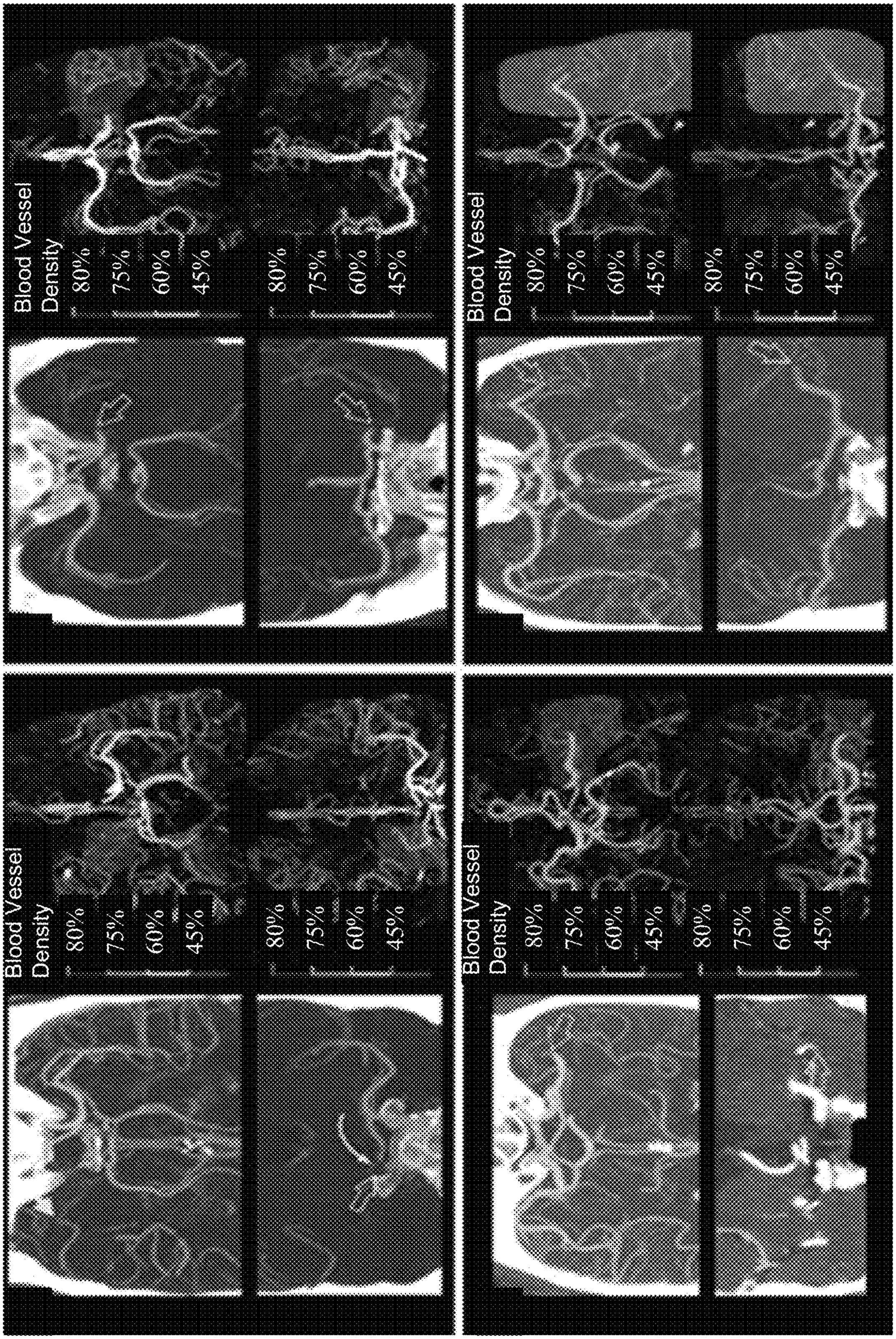
FIG. 16 shows example images related to results for automatic large vessel occlusion (LVO) detection.

Representative examples of automatic lesion detection in 4 patients with intracranial LVOs are shown in FIG. 16. For the 926 cases that were processed, the median turn-around time, that is, from start of data transmission to receipt of results, was 158 seconds (IQR: 140-176 seconds) of which the elastic registration was the most time-consuming step (≈130 seconds).

FIG. 16. Example results for automatic large vessel occlusion (LVO) detection. Upper Left, 65-yo male with distal internal carotid artery (ICA) occlusion (open arrows) and occlusion of A 1-ACA segment (curved arrow) with partial reconstitution of through collaterals (arrow). The area of severe vascular density reduction as determined by the algorithm is shown in red. Upper Right, 72-yo female with a left proximal M1-middle cerebral artery (MCA) occlusion (open arrows). The area of abnormal density found by the software is highlighted in red. Lower Left, 84-yo male with a distal M1 occlusion on the left (open arrows) and the area of abnormal vessel density in red. Lower Right, 55-yo male with occlusion of the proximal left superior M2 division (open arrows) and corresponding region picked by the software. The degree of vessel density reduction was less than in the other 3 patients.

Figure 17A:
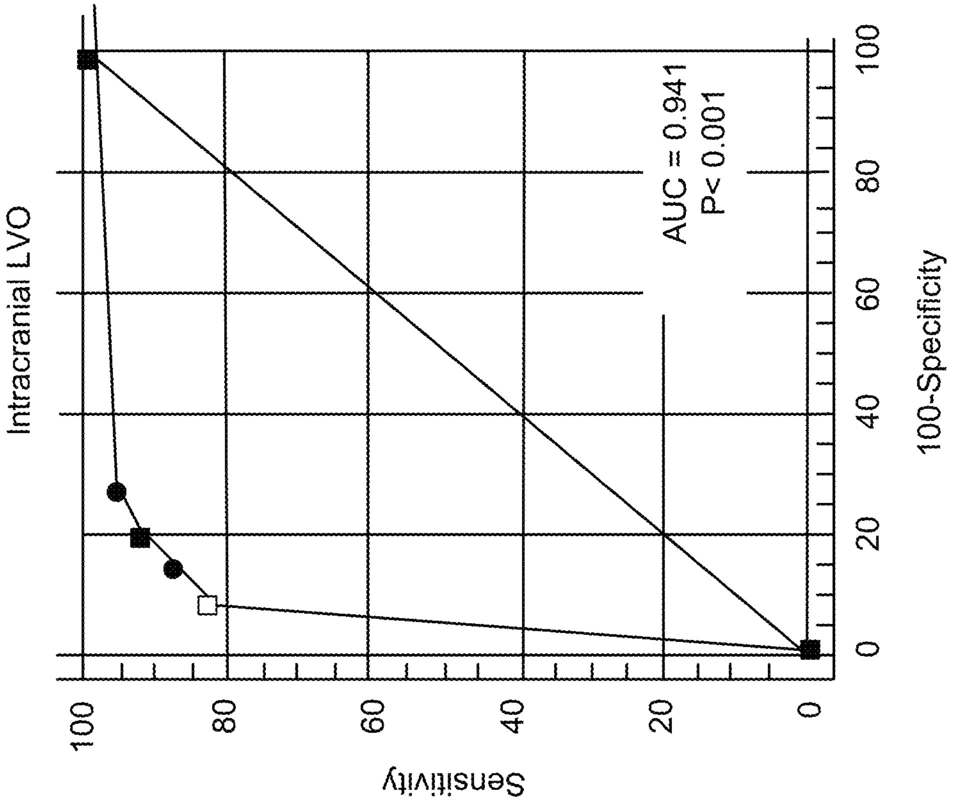
FIGS. 17A and B show ROC curves for detection of intracranial large vessel occlusions (LVOs).

Intracranial LVOs:

Three hundred-twenty patients had an intracranial anterior circulation LVO, while the remaining 588 did not (Table 1). The automatic algorithm yielded an AUC of 0.941 (95% CI. 0.926-0.957). The sensitivity target of ≥95% was achieved at a <75% to 60% (GREEN) threshold, yielding a sensitivity of 96.87% (310/320 [95% CI, 94.3%-98.51%]) and specificity of 74.32% (437/588 [95% CI. 70.6%-77.81%]; FIG. 17(A)).

TABLE 1

Algorithm's Diagnostic Performance for Intracranial LVOs

| | N(%) | AUC* (95% Cl) | Target Sens (%; 95% Cl in %) | Target Spec (%; 95% Cl in %) | Threshold (Range, Color Code) | $J_{max}$ Sensitivity (%, 95% Cl in %) | $J_{max}$ Specificity (%, 95% Cl in %) | $J_{max}$ (95% Cl) threshold (Range, Color Code) |
|---|---|---|---|---|---|---|---|---|
| Intracranial LVOs | 320 (25.24) | 0.941 (0.926-0.957) | 310/320 (96.87) 94.3-98.5 | 437/588 (74.32) 70.6-77.8 | <75%-60% GREEN | 264/320 (82.50) 77.9-86.5 | 560/588 (95.24) 93.2-96.8 | 0.7774 (0.7352-0.8160) <45% RED |
| No LVO | 588 (64.76) | | | | | | | |
| Intracranial LVOs incl isolated M2s | 368 (40.40) | 0.947 (0.933-0.962) | 351/368 (95.38) 92.7-97.3 | 431/543 (79.37) 75.7-82.7 | <75%-60% GREEN | 334/369 (90.76) 87.3-93.5 | 469/543 (86.37) 83.2-89.1 | 0,7713 (0.7322-0.8117) <60%-45% YELLOW |
| No LVO | 543 (59.60) | | | | | | | |

Target sens is associated with threshold that yields ≥95% sensitivity at the highest specificity (Target Spec). $J_{max}$ is the maximum Youden index (sensitivity + specificity − 1) across all threshold. $J_{max}$ provides an optimality criterion with equal weighting for sensitivity and specificity and serves as a secondary reference point. AUC indicates area under the curve; and LVO, large vessel occlusion.

*The DeLong algorithm was used to compute the SE of the AUC.

FIG. 17. ROC analysis. ROC curves for detection of all intracranial (large vessel occlusion [LVOs], A) and all intracranial LVOs and proximal M2-middle cerebral artery (MCA) segment occlusions (B). Dots on the ROC curve indicate individual threshold levels, the one with the lowest sensitivity and highest specificity is the <45% threshold whereas the highest sensitivity and lowest specificity were at the <80% to 75% threshold. The open circle indicates the maximum Youden index. The asterisks indicate the threshold at with the 295% sensitivity target was reached with the highest specificity. The significance level in the legend indicates the P value of the z-statistic derived from the DeLong algorithm. AUC indicates area under the curve.

Figure 17B:
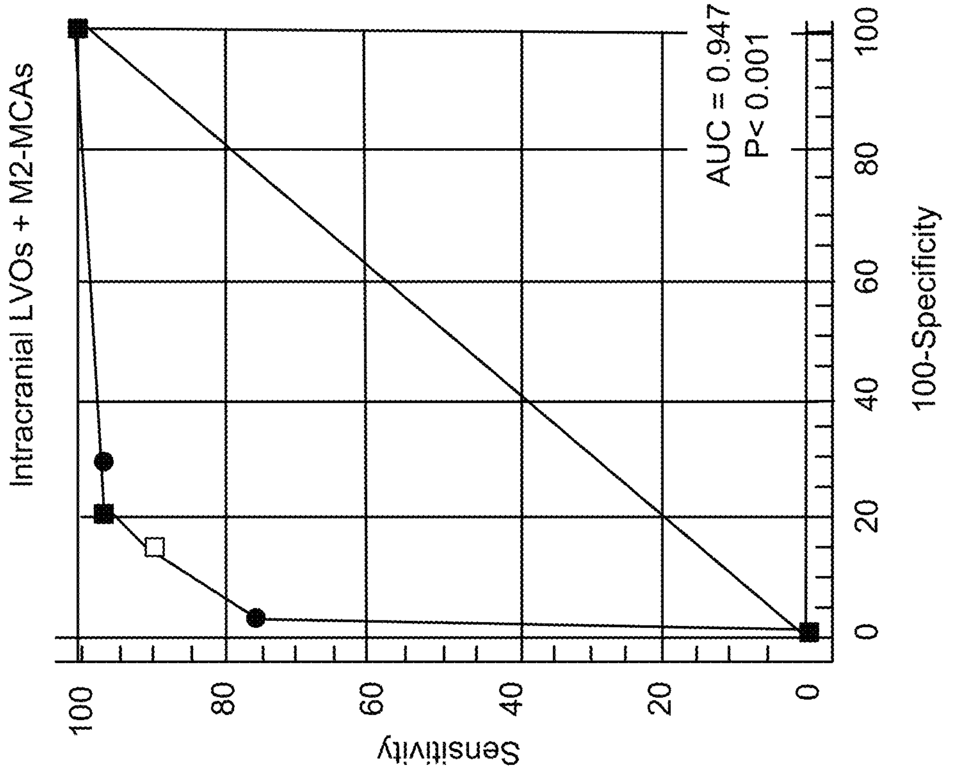

Intracranial LVOs+M2-MCA Occlusions:

Three hundred sixty-eight patients had an anterior circulation LVO or a proximal M2-MCA occlusion, while 543 patients did not. The target sensitivity of ≥95% was met at the <75% to 60% (GREEN) threshold, which yielded a sensitivity of (351/368) 95.38% (95% CI. 92.7%-97.3%) and specificity of (431/543) 79.37% (95% CI, 75.7%-82.7%). The overall diagnostic performance—as measured by an AUC of 0.947 (95% CI, 0.933-0.962)—improved slightly by adding M2 segments: this was due primarily to improved specificity with only a minor (1.49%) drop in sensitivity (FIG. 17B).

b. Individual Vessel Segments

For this sub-analysis, the 531 patients who had no LVO or M2-MCA occlusion served as controls.

Intracranial ICA (Including ICA Terminus):

One hundred thirty-three patients had an intracranial ICA occlusion. The algorithm yielded an AUC of 0.977 (95% CI, 0.965-0.989). The ≥95% sensitivity target was achieved with the <60% to 45% (YELLOW) threshold that yielded a very high sensitivity of 96.99% (129/133 [95% CI, 92.5%-99.2%]) at a specificity of 86.44% (459/531 [95% CI, 83.2%-89.2%]: Table 2).

TABLE 2

Algorithm's Diagnostic Performance for Individual Vessel Segments

| | No. Occlusions (%) No. Controls | AUC* (95% Cl) | Target Sens (%; 95% Cl in %) | Target Spec (%; 95% Cl in %) | Threshold (Range) COLOR | $J_{max}$ Sensitivity (%, 95% Cl in %) | $J_{max}$ Specificity (%, 95% Cl in %) | $J_{max}$ (95% Cl); threshold (Range, Color Code) |
|---|---|---|---|---|---|---|---|---|
| Intracranial ICA incl. terminal ICA | 133 (20.03) 531 | 0.977 (0.965-0.989) | 129/133 (96.99) (92.5-99.2) | 459/531 (86.44) (83.2-89.2) | <60%-45% YELLOW | 118/133 (88.72) (82.1-93.5) | 521/531 (98.12) 96.6-99.1 | 0.8664 (0.8174-0.9153) <45% RED |
| M1-MCA | 290 (36.32) 531 | 0.962 (0.948-0.976) | 281/290 (96.90) (94.2-98.6) | 423/531 (79.66) (6.0-83.0) | <75%-60% GREEN | 243/290 (83.79) (79.0-87.8) | 521/531 (98.12) 96.6-99.1 | 0.8191 (0.7724-0.8494) <45% RED |
| M2-MCA | 60 (10.15) 531 | 0.874 (0.826-0.921) | 54/60 (90.00)† (79.5- | 398/531 (74.95) (71.0- | <80%-75% BLUE | 52/60 (86.67) (75.4- | 423/531 (79.66) 76.0- | 0.6633 (0.5479-0.7327) |

TABLE 2-continued

Algorithm's Diagnostic Performance for Individual Vessel Segments

| No. Occlusions (%) No. Controls | AUC* (95% CI) | Target Sens (%; 95% CI in %) | Target Spec (%; 95% CI in %) | Threshold (Range) COLOR | $J_{max}$ Sensitivity (%, 95% CI in %) | $J_{max}$ Specificity (%, 95% CI in %) | $J_{max}$ (95% CI); threshold (Range, Color Code) |
|---|---|---|---|---|---|---|---|
| | | 96.2) | 78.6) | | 94.1) | 83.0 | <75%-60% GREEN |

Target sens is associated with threshold that yields ≥95% sensitivity at the highest specificity (Target Spec). $J_{max}$ is the maximum Youden index (sensitivity + specificity − 1) across all threshold.
AUC indicates area under the curve;
ICA, internal carotid artery;
and MCA middle cerebral artery
*The DeLong algorithm was used to compute the SE of the AUC.
†For M2-MCA segments ≥95% sensitivity could not be met.

M1-MCA:

Two hundred ninety patients had an M1-MCA occlusion. The algorithm yielded an AUC of 0.962 (95% CI, 0.948-0.976). Although the diagnostic performance as measured by AUCs was slightly inferior for detection of M1-MCA occlusions compared with intracranial ICA occlusions. The 95% sensitivity target was met at the <75% to 60% (GREEN) threshold, which yielded a sensitivity of 96.90% (281/290 [95% CI, 94.2-98.6]) and specificity of 79.66% (423/531 [95% CI, 76.0%-83.0%]: FIG. 18B).

M2-MCA:

Sixty patients had a proximal M2-MCA segment occlusion. The automated algorithm performed slightly worse than for detection of the M1-MCA segment occlusions, nevertheless yielding an AUC of 0.874 (95% CI, 0.826-0.921). The ≥95% sensitivity target could not be reached at any threshold but at the <80% to 75% (BLUE) threshold a sensitivity and specificity of 90.00% (54/60 [95% CI, 79.5%-96.2%]) and 74.95% (398/531 [95% CI, 71.0-78.6]), respectively was achieved (FIG. 18C).

c. False Negatives

The number of false negative, where an intracranial LVO was not detected even at the most sensitive threshold (<80%-75%; BLUE), were relatively small (n=14). 1 intracranial ICA, 8 M1-MCA occlusion and 5 proximal M2-MCA occlusions.

Figure 19:
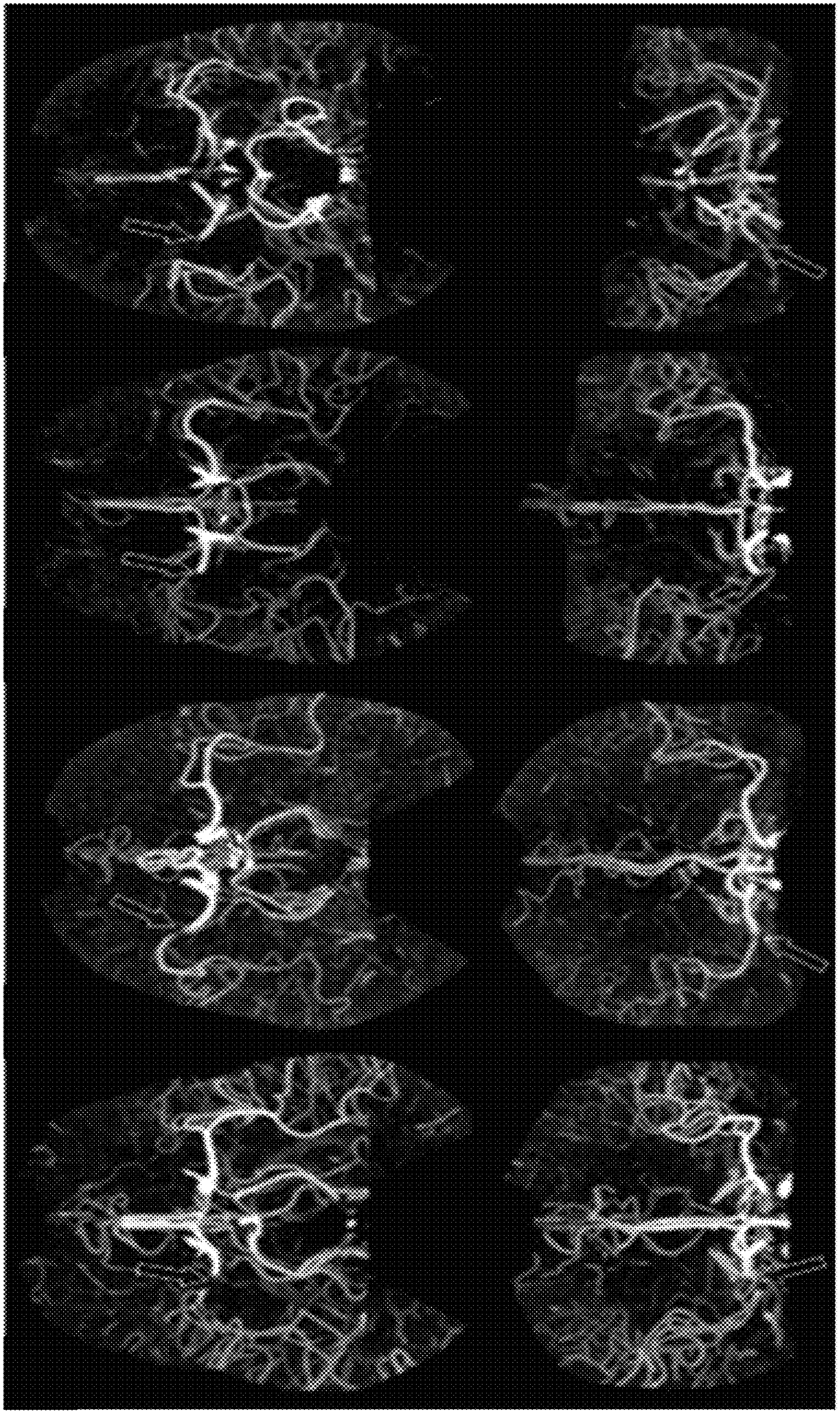
FIG. 19 shows images of false negative results.
Figure 20:
FIG. 20 shows additional images of false negative results.

For the 8 M1-MCA lesions, there were 3 short-segment or incomplete occlusions with reconstitution of flow immediately distal to the occlusion. Here, trickle flow across an incomplete occlusion or retrograde filling via leptomeningeal collaterals led to normal or increased ipsilateral vessel density. The 5 remaining were mid-to-distal M1-MCA occlusions distal to the R1 region level with robust leptomeningeal collaterals reconstituting the M2-MCA segments, resulting in normal or increased vessel density in the ipsilateral R2 and R3 regions (FIG. 19 provides examples of these false-negative cases). The only intracranial ICA occlusion that was missed was at the skullbase, with normal opacification of the supraclinoid ICA (FIG. 20, left).

Five M2-MCA occlusions were missed: one occlusion was located in the upper half of the Sylvian cistern, which was not covered by the R2 template; 2 were occluded nondominant proximal superior M2-MCA branches; 2 were short-segment proximal occlusions of their inferior M2 divisions with reconstitution immediately distal to the occlusion (FIG. 20, right), indicating robust leptomeningeal collaterals. When proximal M2-MCA occlusions were included in the group, in addition to intracranial LVOs, the total number of false negatives decreased from 14 to 9.

d. False Positives

There were 11 false positives for LVO detection at the most specific threshold (RED, where there was a marked inter-hemispheric vessel density difference of <45%). These were attributed to (1) substantial inter-hemispheric variation in MCA anatomy (n=4) or fetal-origin of the posterior cerebral artery (n=1); (2) holohemispheric subdural hematoma with mass effect resulting in 17 mm midline shift (n=1); (3) an 8 mm distal MCA aneurysm; (4) M2-MCA stenosis (n=3); and (5) incomplete recanalization (TICI 2b) after a mechanical thrombectomy attempt 24 hours before the CTA (n=1). There were an additional 17 false positives for LVOs detection when M2-MCAs were not included in the LVO group: all 17 were proximal M2-MCA occlusions.

False positives at the <80% to 75% (BLUE), <75% to 60% (GREEN), and <60% to 45% (YELLOW) thresholds were due to: anatomic variation in M1-MCA branching patterns and vessel calibers, fetal origin of the posterior cerebral arteries, and other vascular pathology, such as ipsilateral segmental flow reduction in chronic steno-occlusive disease and contralateral increase in blood flow due to reactive hyperemia (e.g., due to reperfusion of an infarct or seizures in a patient with a glioblastoma). These examples can be found in Figures VI and VII.

Discussion

This study evaluated a new algorithm for automated detection of intracranial anterior circulation LVOs and demonstrated that it has excellent diagnostic sensitivity and high specificity. The short processing time (<160 seconds) makes its application feasible in the emergent clinical setting.

Previous studies have shown that neuroradiologists can detect LVOs with 89% to 98% sensitivity and 95% to 98% specificity. Automation, which does not achieve this high specificity, cannot replace radiologists; rather, its strength and utility lie in the high sensitivity, which allows expedited diagnosis of LVOs by flagging and prioritizing these scans as requiring urgent radiologist review. A very high sensitivity is a requirement for a screening tool. The algorithm met the targeted sensitivity of 295% for the detection of any intracranial LVO. This is comparable to that of experienced neuroradiologists, whose sensitivity for detecting LVOs is high but imperfect, reported to be 90% for detection of ICA occlusions in one study. Sensitivity is lower for readers with less experience in interpreting cranial CTA, such as general radiologists and trainees, with sensitivity as low as 63% in one study.

At many centers around the world, trainees are the first to interpret multimodal stroke CTs, which are subsequently formally read by a neuroradiologist. Further, not all hospitals and healthcare services around the world have access to around-the-clock neuroradiology expertise. At some primary stroke centers and community hospitals, such as that from which cohort 5 was drawn, general radiologists interpret multimodal stroke CTs, and there is typically only one on-call radiologist or resident after-hours due to limited resources. Acute stroke scans may be overlooked in this setting when other emergent scans such as trauma are given priority. These factors can contribute to delayed and missed diagnosis of LVOs in the authors' experience. The fully automated algorithm is likely to be both a valuable diagnostic aide and screening tool in these settings. It can expedite the correct diagnosis by bringing positive findings to the reporting radiologist's or resident's attention. It can also facilitate notification of the stroke team and neurointerventionalist, allowing mobilization of the clot retrieval team which in turn would expedite treatment of eligible patients. Another important consideration is that the algorithm provides consistency, in contrast to the surprisingly poor interrater agreement between human readers.

For individual segments, an almost perfect sensitivity was achieved for occlusion of the intracranial ICA or M1-MCA: sensitivity for detection of proximal M2-MCAs was slightly lower. This was attributable to false negatives resulting from short-segment (where collaterals reconstituted the M2 segment immediately distal to the occlusion) and incomplete (with antegrade flow) occlusions, where the inter-hemispheric vessel density reduction was too small for the algorithm to detect. It is thought that robust collaterals confer a longer time-window for treatment. 0 On post hoc analysis, the algorithm did not miss an LVO in any patient with poor collaterals; these patients are likely to be fast progressors, in whom expeditious reperfusion is imperative for tissue salvage. It is important that radiologists and neurologists are cognizant of the presence and causes of false negatives, and a negative result should not dissuade thorough and careful evaluating the CTA as soon as practicable.

The algorithm's overall specificity was >74% for intracranial LVO detection and >79% when M2-MCAs were included. For individual segments, specificity was 75% for detection of M2-MCA occlusions, increasing to 80% for M1-MCA and 86% for intracranial ICA occlusions. The justification for including M2-MCA occlusions in the LVO detection algorithm is that they are now a subject of interest as a mainstream target for ECR. Thrombectomy may improve outcomes compared with standard medical management in patients with M2-MCA occlusions. Detection of M2-MCA occlusions was, however, more challenging due to the greater anatomic variability and smaller caliber of these vessels. Moreover, the version of the software used for this study constrained the region of interest, in which vessel density was determined, to cover only the proximal half of the M2 segments, to the mid-point of the Sylvian cistern; future implementations will expand the region further distally.

The LVO detection tool evaluated in this study had 3 regions, R1-R3, and 4 different thresholds for LVO detection, reflecting lesion location and increasing severity of vessel density reduction. The diagnostic sensitivity decreased while specificity increased when the threshold was changed from <80% to <45% vessel density reduction. The (<75/−60%) threshold was found to be optimal; it yielded the desired sensitivity of ≥95% with an acceptable specificity between 70% to 80%. For radiologists, this would still substantially decrease the number of scans that require emergent review. If, however, fewer false LVO alerts are desired, this can be achieved simply by moving along the ROC curve and trading the target >95% sensitivity for increased specificity.

To our knowledge, this is the first peer-reviewed publication which has introduced an automated LVO detection tool and evaluated its performance in a multicenter study that incorporates a large and diverse cohort of patients. A few conference abstracts have been published recently related to this topic yet unrelated to this algorithm. The number and mix of patients enrolled, and the results reported in these abstracts vary widely, with a sensitivity for LVO detection of 90% to 97% and a broad specificity range of 52% to 83%.

A strength of this pooled cohort study is that we included patients who were enrolled in 2 high-profile multicenter stroke trials. This provided validation of the algorithm in a preselected cohort of patients with acute ischemic stroke with an LVO who were considered thrombectomy candidates. The large number of patients with LVOs allowed robust testing of diagnostic sensitivity. The other large cohort consisted of consecutive patients presenting to a regional hospital with a suspected acute ischemic stroke. Inclusion of this cohort of all corners allowed testing of the algorithm on a broad spectrum of stroke mimics and ensures broad applicability of our findings to the population of patients in whom LVO detection tools will most likely be used. Inclusion of multiple patient cohorts from different sites in this study allowed testing and validation of the algorithm on different makes and models of CT scanners and CTA protocols.

This study has a few pertinent limitations. First, it is a retrospective study. As such, we did not have complete data sets for all patients, particularly with regard to clinical information regarding long-term outcomes and clinical scores. A prospective study that includes at least one comprehensive stroke center (hub) and several peripheral and regional/community hospital (spokes) is required to test whether the tool can be used to streamline intra- and inter-institutional workflows. Limitations related to the algorithm itself include the processing requirement for thin-slice CTA raw data and arterial opacification. Thin-slice CTA data is routinely acquired even on older generation multi-slice CT scanners, which may still be in use at some centers. The requirement for contrast opacification of the intracranial arteries also applies to the human reader. There were 15/969 (1.5%) patients in whom arterial opacification on CTA was deemed either absent or too poor to allow accurate interpretation by an experienced human reader. Eight of these cases were from cohort 5, a regional hospital. The proportion of technically inadequate studies may be higher at smaller community hospitals where the volume of CTAs performed is smaller and technologist staff are, therefore, less experienced. All cases where the arterial opacification was deemed to be sufficient to allow human interpretation were successfully processed by the algorithm.

It is noted that the algorithm does not directly detect the clot but rather the resultant loss of vessel opacification, therefore false positives result from chronic occlusions. The purpose of this software is to serve as a triage tool that alerts radiologists to a patient with a potential LVO, and in turn trigger evaluation of the patient's multimodal CT by the human reader who can then use all available information (not just the CTA) to make a judgement call. Precise localization of the occlusion site and differentiation of chronic occlusions by the algorithm is, therefore, not critical and was hence not evaluated in this study.

In summary, intracranial LVOs within the anterior circulation—inclusive of proximal M2-MCA occlusions—can be detected effectively and efficiently by an automated computerized screening tool. Future prospective studies may be warranted to determine whether this tool can be used to improve workflow and expedite treatment.

Supplemental Material

Supplemental Methods—Algorithm Description

The underlying concept of the LVO detection presented here relies on software that is able to detect reduced opacification and number of anterior intracranial vessels. It is composed of eight major steps:

1. DataImport: Native, thin-sliceCTADICOMimagesareimportedintothesoftware.
2. Pre-Processing: a. Trim CTA input data to keep only slices located between C1 vertebrae and vertex, b. Remove CT head holder from all CTA images.
3. Identify Anatomy: a. An anatomic template of a human head is elastically aligned with the patient's CTA dataset using non-rigid registration1, b. Templates of relevant anatomic structures (e.g. bones, vessels) and the three pre-specified hemispheric regions of interest (R1, R2, and R3) relevant for subsequent analysis (defined in the coordinate space of the anatomic template) are warped onto the patient's CTA using the transformation parameters determined in (a). Of note here, the R2 region covers the M2-MCA segment from its genu half-way to the top of the Sylvian cistern.
4. BoneRemoval: Using the bone mask defined in step 2, the skull base and calvarium are removed from the CTA volume.
5. Vessel Detection: Intracranial vessels are identified and categorized into large and small diameter vessel groups using tubular filtering 2.
6. Evaluate Regions: a. The total sum of voxel densities (in Hounsfield Units) within the large caliber vessels—the intracranial ICA and proximal M1-MCA segment (R1)—is assessed together with each vessel's segment length, b. For "small caliber" vessels—the mid-to-distal M1 (R2), M2, and more distal MCA segments (R3)—the total sum of voxel densities (as determined in the previous step) is measured.
7. Abnormality Detection: a. Density metrics for R1, R2, and R3 are compared between hemispheres, b. The following thresholds for relative hemispheric vessel density ratio and corresponding color schemes were used: <80/6-75% (BLUE); <75/6-60% (GREEN); <60%-45% (YELLOW); and <45% (RED). Here, the percentage indicates the fraction of signal relative to the opposite hemisphere, i.e. <45% (RED) constitutes the greatest drop in vessel density whereas <80%-75% is the most mild reduction, c. The regions are priority ranked from R1 to R3 with R1 given the highest priority. That is, the algorithm compares R1 regions in both hemispheres first and only progresses to the next regions (i.e. R2 and then R3) if the density reduction did not meet the chosen severity threshold.
8. Report Generation: a. De-tilted and rotation-corrected axial, coronal, and sagittal maximum intensity projections (MIPs) of the intracranial vasculature were rendered from the bone-masked CTA volumes, b. The regions R1, R2, or R3—depending on which are deemed abnormal (based on the aforementioned metrics)—are highlighted as color overlays on the MIP images. For simplicity of review, only the most proximal region demonstrating hemispheric abnormality is shown on the overlay, c. Annotated and unannotated MIPs are then exported as secondary capture DICOM images. Supplemental References 1. Klein S, Staring M, Murphy K. Viergever M A. Elastix: A toolbox for intensity based medical image registration. IEEE Transactions on Medical Imaging. 2010, 29:196-205.
2. Frangi A F, Niessen W J, Vincken K L, Viergever M A. Multiscale vessel enhancement filtering. Medical image computing and computer-assisted intervention—miccai'98. 1998; 1496:130-137.

Supplemental Figures

Figure 18A:
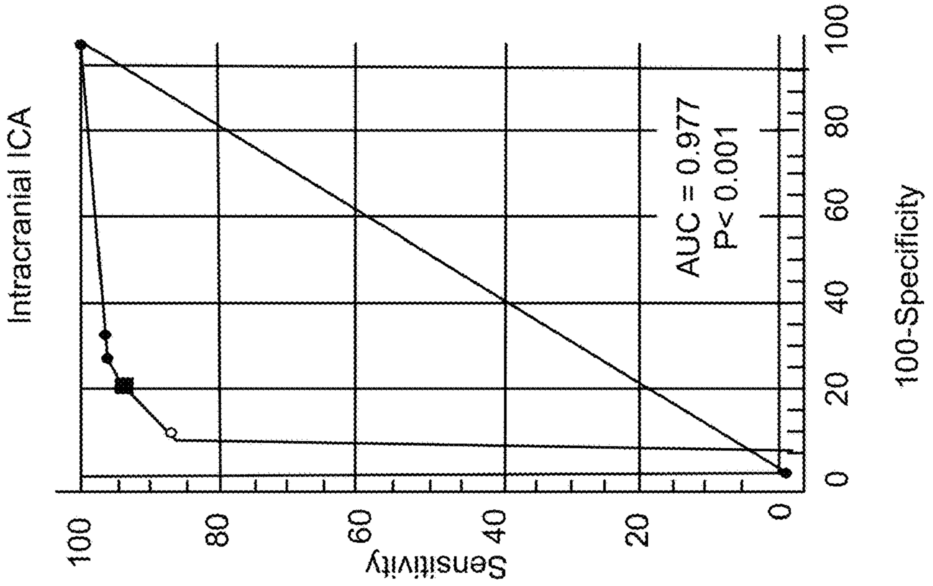
FIGS. 18A-C show ROC curves for occlusion of individual vessel segments.
Figure 18B:
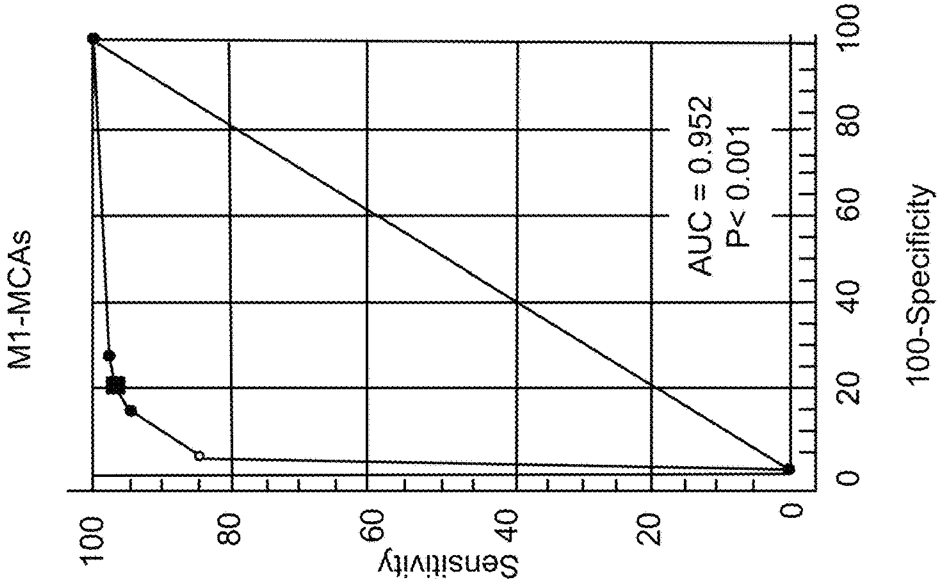
Figure 18C:
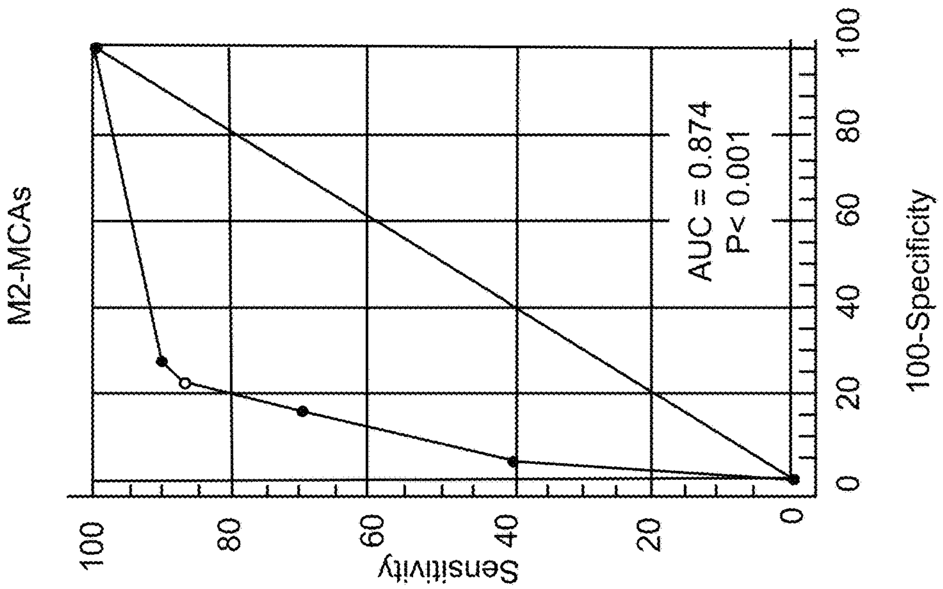

FIG. 18—ROC Analysis for occlusion of individual vessel segments. Diagnostic performance for detection of intracranial ICA occlusions (A) was almost perfect, with excellent performance also for M1-MCA occlusions (B) and good performance for M2-MCA occlusions (C). Dots on the ROC curve indicate individual threshold levels: the one with the lowest sensitivity and highest specificity is the <45% threshold whereas the highest sensitivity and lowest specificity were at the <80%-75% threshold. The open circle indicates the maximum Youden index. The asterisks indicate the threshold at with the >95% sensitivity target was reached with the highest specificity. The significance level in the legend indicates the p-value of the z-statistic derived from the DeLong algorithm.

FIG. 19—False Negative Results. (Far Left and Middle Left) show axial and coronal MIPs of patients with short-segment M1-MCA occlusions (open arrows) with good collaterals reconstituting the distal M1 segment and the M2 segments, indicated by high luminal density ("CTA signal") distal to the occlusion, albeit with reduced caliber. (Far Left) 76-yo female with a right mid M1 occlusion. (Middle Left) 61-yo male with a right distal M1 occlusion. (Middle Right to Far Right) show two patients with complete mid-M1 occlusions (open arrows). Both patients had robust collaterals, indicated by opacification of the proximal M2 segments, that led to the negative output of the algorithm.

FIG. 20—False negative examples at softest (BLUE) threshold. (Left) Skull base ICA occlusion (arrow). Opacification of the supraclinoid ICA and distal to region highlighted by the yellow arrow led to a false negative detection. (Right) One out of five false negatives with mid-to-distal M1 occlusion (arrow) with prominent collaterals (asterisk) immediately distal to occlusion.

Figure 21:
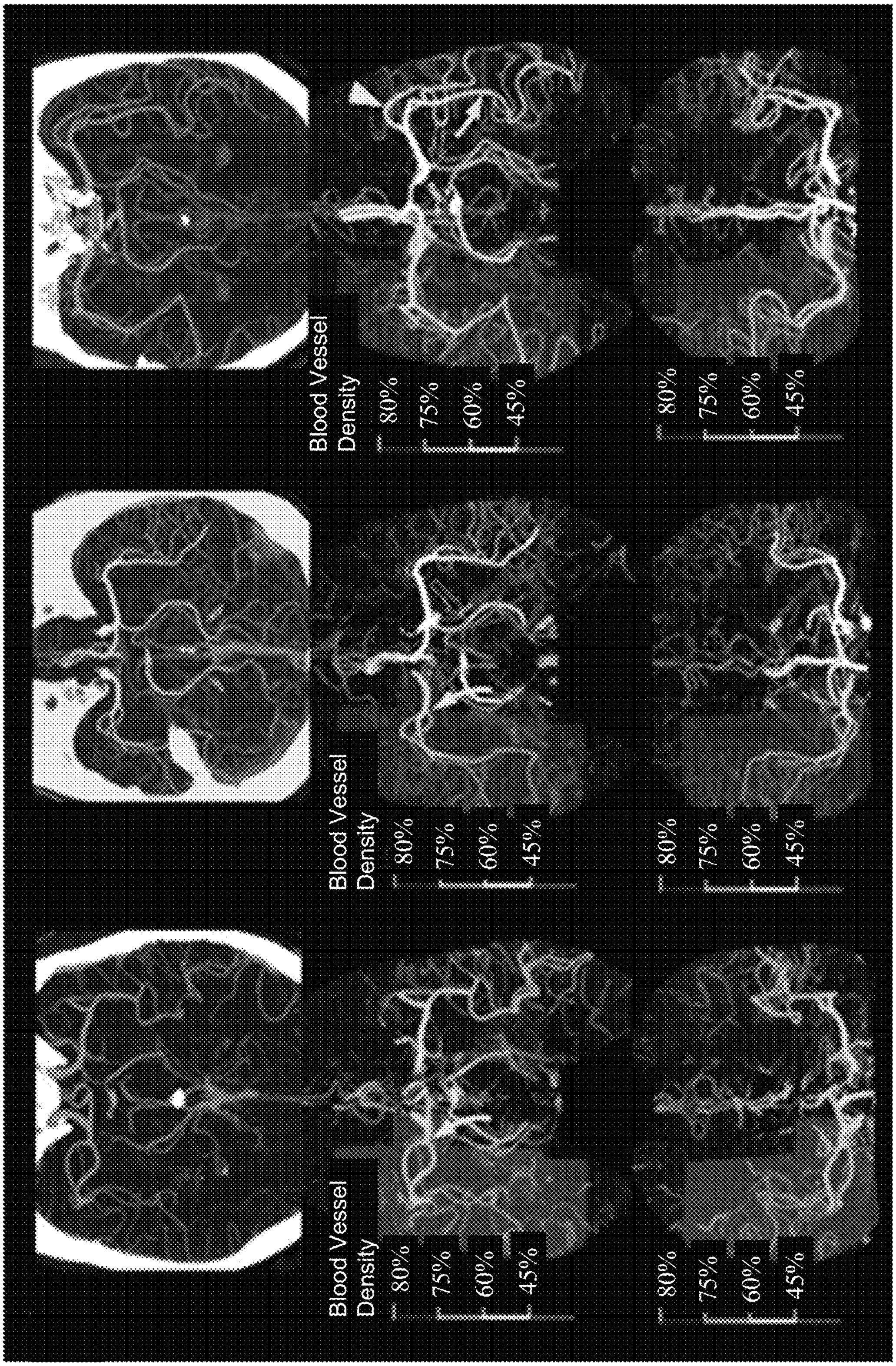
FIG. 21 shows images of false positive results related to normal variants.

FIG. 21—False Positive Results related to Normal Variants. (Left) 67-yo male with a very early bifurcation of the right M1-MCA (curved arrow) and consequently more prominent distal vessels in the left hemisphere. (Middle) 68-yo male with an early trifurcation of the right M1-MCA (curved arrow) resulting in greater prominence of the left MCA M1 segment and distal branches. A left fetal PCA (open arrow) was also present and contributed to the hemispheric asymmetry in vessel density. (Right) 71-yo male with prominent anterior (arrowhead) and posterior (curved arrow) M2 divisions relative to their contralateral counterparts. A left fetal PCA (open arrow) contributed to further hemispheric imbalance. Corresponding original thin slice MIPs (top row) are added as color overlays exaggerate vessel density which makes it harder to appreciate the reduced vessel density.

Figure 22:
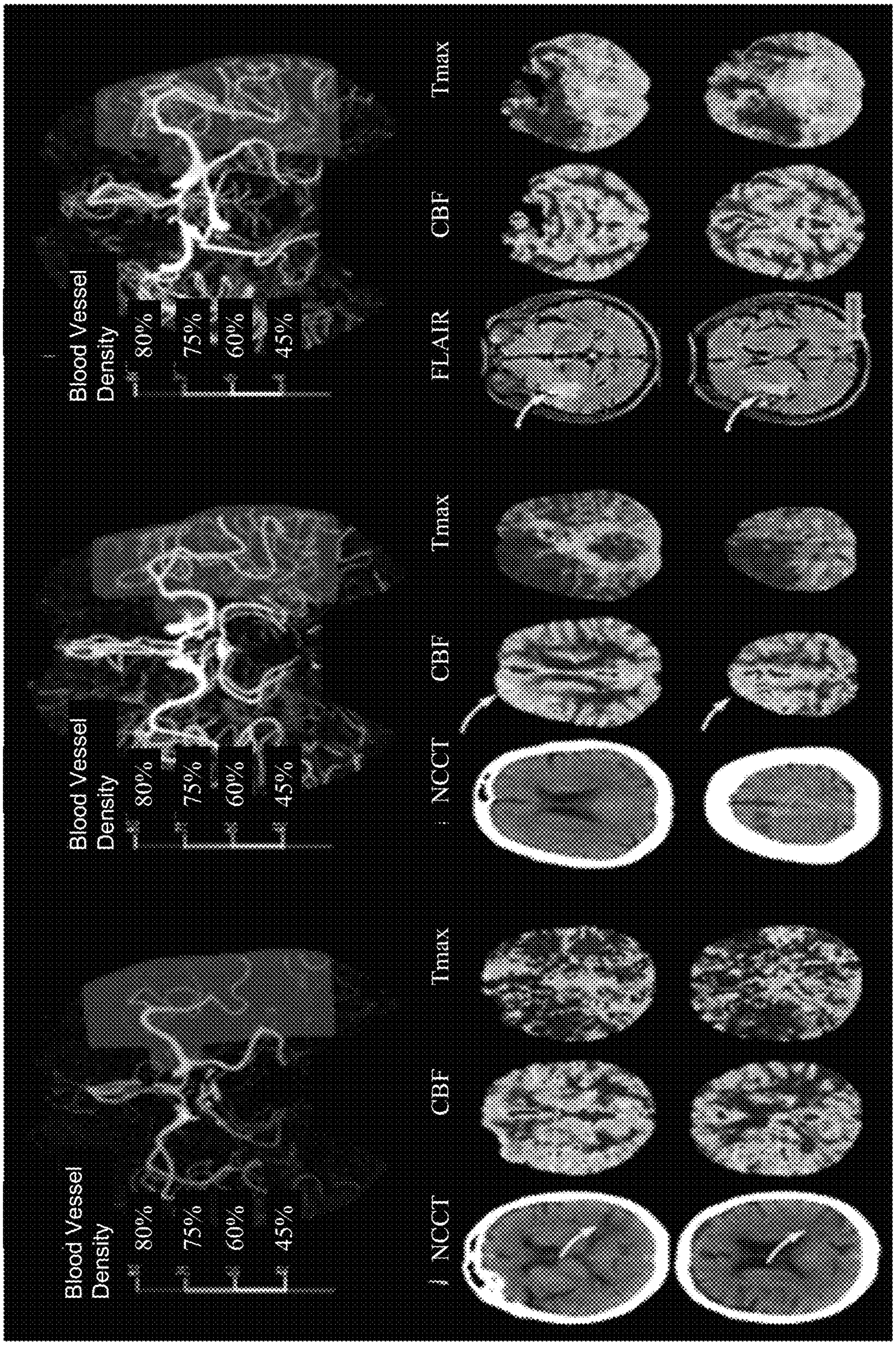
FIG. 22 shows additional images of false positive results from other pathology.

FIG. 22—False Positive Results from other pathology. (Left) 89-yo male with an old infarct (curved arrow) within the posterior aspect of the left MCA territory (distal inferior M2 subdivision). Reduced blood flow and high Tmax from CTP is also shown. There was a chronic occlusion of the distal inferior M2 division, resulting in a paucity of vessels in the infarcted region and hemispheric imbalance (green region). (Middle) 82-yo female with hyperperfusion in the right anterior MCA and ACA territory (curved arrow) and hypodensity on NCCT (open arrow), likely due to a reperfused acute infarct. The substantially higher flow within this area (seen best on perfusion parametric maps as elevated relative CBF and decreased Tmax) increased the overall vessel density, which in turn led to asymmetry which was interpreted by the algorithm as lower CTA opacification in the contralateral hemisphere. (Right) 79-yo male patient with a GBM in the right insula (curved arrow). Hypervascularity related to the tumor itself and seizure activity led to increased blood flow (best appreciated on CBF and Tmax maps) within and adjacent to the insula, which increased overall CTA opacification in this region relative to the contralateral hemisphere.

Supplemental Tables

The five tables below provide the full confusion matrices for all tests performed and will allow interested researchers to reproduce the ROC analyses performed for this study.

TABLE Ia

Diagnostic Performance for LVOs

| Threshold | 0 | 1 | 2 | 3 |
|---|---|---|---|---|
| TP | 311 | 310 | 300 | 264 |
| FP (type 1) | 180 | 151 | 106 | 28 |
| TN | 408 | 437 | 482 | 560 |
| FN (type 2) | 9 | 10 | 20 | 56 |
| 1-Spec | 30.61% | 25.68% | 18.03% | 4.76% |
| Sens | 97.19% | **96.88%** | 93.75% | *82.50%* |
| Spec | 69.39% | **74.32%** | 81.97% | *95.24%* |
| PPV | 63.34% | 67.25% | 73.89% | 90.41% |
| NPV | 97.84% | 97.76% | 96.02% | 90.91% |
| Accuracy | 79.19% | 82.27% | 86.12% | 90.75% |
| Youden J | 0.6658 | 0.7119 | 0.7572 | 0.7774 |

Bold Text - threshold that meets ≥95% sensitivity requirement at highest achievable specificity
Italicized Text - threshold that yields the maximum Youden index, $J_{max}$ TABLE Ib Diagnostic Performance for LVOs, incl. M2-MCAs

| Threshold | 0 | 1 | 2 | 3 |
|---|---|---|---|---|
| TP | 354 | 351 | 334 | 282 |
| FP (type 1) | 139 | 112 | 74 | 11 |
| TN | 404 | 431 | 469 | 532 |
| FN (type 2) | 14 | 17 | 34 | 86 |
| 1-Spec | 25.60% | 20.63% | 13.63% | 2.03% |
| Sens | 96.20% | **95.38%** | *90.76%* | 76.63% |
| Spec | 74.40% | **79.37%** | *86.37%* | 97.97% |
| PPV | 71.81% | 75.81% | 81.86% | 96.25% |
| NPV | 96.65% | 96.21% | 93.24% | 96.08% |
| Accuracy | 83.21% | 85.84% | 88.14% | 99.35% |
| Youden J | 0.7060 | 0.7485 | 0.7713 | 0.7460 |

Bold Text - threshold that meets ≥95% sensitivity requirement at highest achievable specificity
Italicized Text - threshold that yields the maximum Youden index, $J_{max}$ TABLE IIa Diagnostic Performance for Intracranial ICAs alone

| Threshold | 0 | 1 | 2 | 3 |
|---|---|---|---|---|
| TP | 132 | 132 | 129 | 118 |
| FP (type 1) | 133 | 108 | 72 | 10 |
| TN | 398 | 423 | 459 | 521 |
| FN (type 2) | 1 | 1 | 4 | 15 |
| 1-Spec | 25.05% | 20.34% | 13.56% | 1.88% |
| Sens | 99.25% | 99.25% | **96.99%** | *88.72%* |
| Spec | 74.95% | 79.66% | **86.44%** | *98.12%* |
| PPV | 49.81% | 55.00% | 64.18% | 92.19% |
| NPV | 99.75% | 99.76% | 99.14% | 97.20% |
| Accuracy | 79.82% | 83.58% | 88.55% | 96.23% |
| Youden J | 0.7420 | 0.7891 | 0.8343 | 0.8684 |

Bold Text - threshold that meets ≥95% sensitivity requirement at highest achievable specificity
Italicized Text - threshold that yields the maximum Youden index, $J_{max}$ Table 11b—Diagnostic Performance for M1-MCAs Alone
- Bold Text—threshold that meets ≥95% sensitivity requirement at highest achievable specificity
- Italicized Text—threshold that yields the maximum Youden index, $J_{max}$ TABLE IIc Diagnostic Performance for M2 - MCAs alone

| Threshold | 0 | 1 | 2 | 3 |
|---|---|---|---|---|
| TP | 282 | 281 | 274 | 243 |
| FP (type 1) | 133 | 108 | 72 | 10 |
| TN | 398 | 423 | 459 | 521 |
| FN (type 2) | 8 | 9 | 16 | 47 |
| 1-Spec | 25.05% | 20.34% | 13.56% | 1.88% |
| Sens | 97.24% | **96.90%** | 94.48% | *83.79%* |
| Spec | 74.95% | **79.66%** | 86.44% | *98.12%* |
| PPV | 67.95% | 72.24% | 79.19% | 96.05% |
| NPV | 98.03% | 97.92% | 96.63% | 91.73% |
| Accuracy | 82.83% | 85.85% | 89.28% | 93.06% |
| Youden J | 0.7219 | 0.7656 | 0.8092 | 0.8191 |

Bold Text - threshold that meets ≥95% sensitivity requirement at highest achievable specificity
Italicized Text - threshold that yields the maximum Youden index, $J_{max}$

Example 3

Methods

The LVO algorithm has a 0/1 or no LVO/LVO outcome. The outcome is determined by setting a threshold to a score determined through a decision tree:

1. If the vessel segment does not reach the distal end of the evaluation region (a hard stop is detected inside the evaluation region) then score=0.0 for vessel density ratio (VDR).
2. If the vessel-tracker is unable to track the vessel towards M2 then score=0.59 for VDR.
3. Otherwise assess the vessel density ratio (this will have a value between 0.0 and 1.0). A score of <0.6 from any analysis is considered positive for LVO detection as described below:

a. If MCA M1 proximal VDR is <0.6, report LVO
b. If MCA M1/M2 distal VDR is <0.45, report LVO
c. If hemispheric VDR <0.6, report LVO.

Based on 217 cases the ROC curve for the LVO algorithm score vs. the Reference LVO determination has an AUC=0.99 (95% bootstrap CI: 0.971, 0.999).

Figure 23:
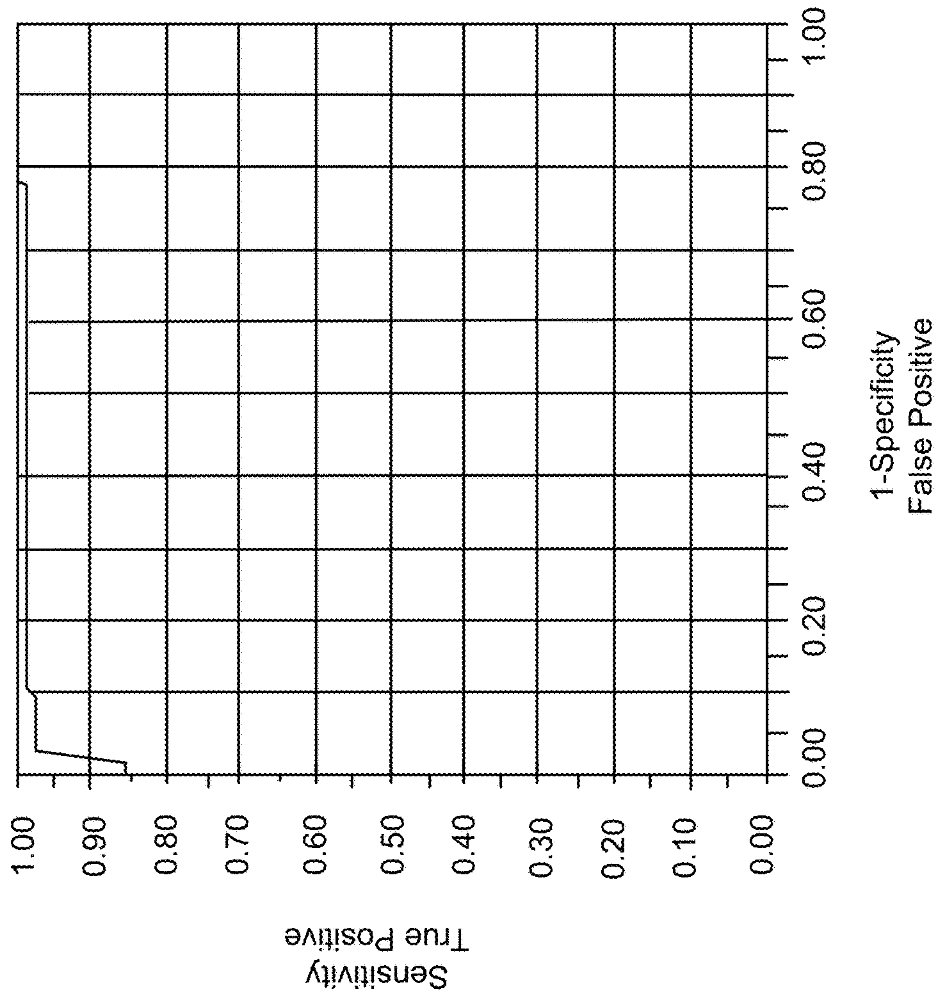
FIG. 23 shows a ROC curve for vessel density ratio scores as predictor of LVO.

FIG. 23: ROC curve for vessel density ratio scores as predictor of LVO. Performance on group of 271 patients 22-95 years old, 100 female, 116 female, 1 unknown; 109 ground-truth-positive and 108 ground-truth-negative cases.

What is claimed is:

1. A method comprising:

obtaining an image of a brain of an individual;

identifying, using the image, a blood vessel located in the brain of an individual based on a template that indicates locations of a number of blood vessels located in a human brain, the template including a composite image generated based on a number of reference images with the number of reference images being obtained from a number of individuals and including brains and other features associated with the brains of the number of individuals;

determining a starting point with respect to the blood vessel, the starting point indicating a first voxel of the image that is included in a path of the blood vessel within the brain of the individual;

determining a path along the blood vessel based on density values corresponding to the blood vessel, the density values indicating an amount of contrast between portions of the image related to the blood vessel and background portions of the image;

determining an endpoint of the blood vessel based at least partly on the template;

determining that the blood vessel terminates before the endpoint; and determining, based on the blood vessel terminating before the endpoint, a probability that an abnormality is present with respect to the blood vessel.

2. The method of claim 1, wherein the path along the blood vessel corresponds to a shortest path that is determined based on vesselness values of voxels of the image in locations that correspond to the location of the blood vessel, the vesselness values corresponding to eigenvalues of a Hessian filter.

3. The method of claim 1, wherein the starting point of the blood vessel corresponds to a voxel having a highest vesselness value, the voxel being located in a proximal portion of the blood vessel.

4. The method of claim 1, wherein the path of the blood vessel terminates based on the cost of the shortest path exceeding a threshold cost.

5. The method of claim 1, wherein the path of the blood vessel terminates in response to determining that no voxels remain along the path of the blood vessel that have a finite cost to pass through.

6. The method of claim 1, wherein the starting point is located in the proximal end of the middle cerebral artery and the endpoint is located in a distal portion of the middle cerebral artery.

7. The method of claim 1, comprising:

identifying, based on the image, one or more first additional blood vessels located in a first hemisphere of the brain;

identifying, based on the image, one or more second additional blood vessels located in a second hemisphere of the brain; and determining a measure corresponding to an amount of difference between one or more first values of one or more first densities of the one or more first additional blood vessels and one or more second values of one or more second densities of the one or more second additional blood vessels.

8. The method of claim 7, wherein the probability that the abnormality is present with respect to the blood vessel is based on the blood vessel terminating before the endpoint and the measure corresponding to the amount of difference between the one or more first values of the one or more first densities and the one or more second values of the one or more second densities.

9. A system comprising:

at least one hardware processor, a non-transitory computer-readable medium storing instructions that, when executed by the at least one hardware processor, cause the at least one hardware processor to perform operations comprising:

obtaining an image of a brain of an individual;

identifying, using the image, a blood vessel located in the brain of an individual based on a template that indicates locations of a number of blood vessels located in a human brain, the template including a composite image generated based on a number of reference images with the number of reference images being obtained from a number of individuals and including brains and other features associated with the brains of the number of individuals;

determining a starting point with respect to the blood vessel, the starting point indicating a first voxel of the image that is included in a path of the blood vessel within the brain of the individual;

determining a path along the blood vessel based on density values corresponding to the blood vessel, the density values indicating an amount of contrast between portions of the image related to the blood vessel and background portions of the image;

determining an endpoint of the blood vessel based at least partly on the template;

determining that the blood vessel terminates before the endpoint; and determining, based on the blood vessel terminating before the endpoint, a probability that an abnormality is present with respect to the blood vessel.

10. The system of claim 9, wherein the path along the blood vessel corresponds to a shortest path that is determined based on vesselness values of voxels of the image in locations that correspond to the location of the blood vessel, the vesselness values corresponding to eigenvalues of a Hessian filter.

11. The system of claim 9, wherein the starting point of the blood vessel corresponds to a voxel having a highest vesselness value, the voxel being located in a proximal portion of the blood vessel.

12. The system of claim 9, wherein the non-transitory computer-readable medium stores additional instructions that, when executed by the at least one hardware processor, cause the at least one hardware processor to perform additional operations comprising:

aligning the image of the brain of the individual with the template by performing a registration process that includes analyzing the image of the brain of the individual to determine features included in the image of the brain of the individual that correspond to additional features included in the template.

13. The system of claim 9, wherein the path of the blood vessel terminates in response to determining that no voxels remain along the path of the blood vessel that have a finite cost to pass through.

14. The system of claim 9, wherein the starting point is located in the proximal end of the middle cerebral artery and the endpoint is located in a distal portion of the middle cerebral artery.

15. One or more computer-readable storage media storing computer-readable instructions that, when executed by one or more hardware processors, cause the one or more hardware processors to perform operations comprising:

obtaining an image of a brain of an individual;

identifying, using the image, a blood vessel located in the brain of an individual based on a template that indicates locations of a number of blood vessels located in a human brain, the template including a composite image generated based on a number of reference images with the number of reference images being obtained from a number of individuals and including brains and other features associated with the brains of the number of individuals;

determining a starting point with respect to the blood vessel, the starting point indicating a first voxel of the image that is included in a path of the blood vessel within the brain of the individual;

determining a path along the blood vessel based on density values corresponding to the blood vessel, the density values indicating an amount of contrast between portions of the image related to the blood vessel and background portions of the image;

determining an endpoint of the blood vessel based at least partly on the template;

determining that the blood vessel terminates before the endpoint; and determining, based on the blood vessel terminating before the endpoint, a probability that an abnormality is present with respect to the blood vessel.

16. The one or more computer-readable storage media of claim 15, wherein the path along the blood vessel corresponds to a shortest path that is determined based on vesselness values of voxels of the image in locations that correspond to the location of the blood vessel, the vesselness values corresponding to eigenvalues of a Hessian filter.

17. The one or more computer-readable storage media of claim 15, wherein the starting point of the blood vessel corresponds to a voxel having a highest vesselness value, the voxel being located in a proximal portion of the blood vessel.

18. The one or more computer-readable storage media of claim 15, wherein the path of the blood vessel terminates based on the cost of the shortest path exceeding a threshold cost.

19. The one or more computer-readable storage media of claim 15, wherein the path of the blood vessel terminates in response to determining that no voxels remain along the path of the blood vessel that have a finite cost to pass through.

20. The one or more computer-readable storage media of claim 15, wherein the starting point is located in the proximal end of the middle cerebral artery and the endpoint is located in a distal portion of the middle cerebral artery.

* * * * *